US011795231B2

(12) United States Patent
Yamniuk et al.

(10) Patent No.: US 11,795,231 B2
(45) Date of Patent: Oct. 24, 2023

(54) ANTAGONISTIC CD40 MONOCLONAL ANTIBODIES AND USES THEREOF

(71) Applicant: Bristol-Myers Squibb Company, Princeton, NJ (US)

(72) Inventors: Aaron Yamniuk, Vancouver (CA); Mary Struthers, Edison, NJ (US); Stanley R. Krystek, Jr., Ringoes, NJ (US); Akbar Nayeem, Newtown, PA (US); Ginger Rakestraw, Somerville, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 71 days.

(21) Appl. No.: 17/670,223

(22) Filed: Feb. 11, 2022

(65) Prior Publication Data
US 2022/0169742 A1 Jun. 2, 2022

Related U.S. Application Data

(60) Division of application No. 17/080,626, filed on Oct. 26, 2020, now Pat. No. 11,254,750, which is a continuation of application No. 16/686,596, filed on Nov. 18, 2019, now Pat. No. 11,261,258.

(60) Provisional application No. 62/769,514, filed on Nov. 19, 2018.

(51) Int. Cl.
| C12N 15/63 | (2006.01) |
| C07K 16/28 | (2006.01) |
| A61K 39/395 | (2006.01) |
| A61K 47/68 | (2017.01) |
| C07K 16/46 | (2006.01) |
| A61P 37/00 | (2006.01) |
| A61K 45/06 | (2006.01) |
| A61K 39/00 | (2006.01) |
| C07K 14/705 | (2006.01) |

(52) U.S. Cl.
CPC ...... *C07K 16/2878* (2013.01); *A61K 39/3955* (2013.01); *A61K 47/68* (2017.08); *A61K 47/6849* (2017.08); *A61P 37/00* (2018.01); *C07K 16/468* (2013.01); *C12N 15/63* (2013.01); *A61K 45/06* (2013.01); *A61K 47/6803* (2017.08); *A61K 2039/505* (2013.01); *C07K 14/70578* (2013.01); *C07K 2317/21* (2013.01); *C07K 2317/24* (2013.01); *C07K 2317/52* (2013.01); *C07K 2317/565* (2013.01); *C07K 2317/622* (2013.01); *C07K 2317/71* (2013.01); *C07K 2317/76* (2013.01); *C07K 2317/92* (2013.01)

(58) Field of Classification Search
CPC . C07K 16/2878; A61K 39/3955; C12N 15/63
See application file for complete search history.

(56) References Cited

U.S. PATENT DOCUMENTS

| 5,530,101 | A | 6/1996 | Queen et al. |
| 5,585,089 | A | 12/1996 | Queen et al. |
| 5,693,762 | A | 12/1997 | Queen et al. |
| 6,180,370 | B1 | 1/2001 | Queen et al. |
| 6,687,673 | B2 | 2/2004 | Mann |
| 6,737,056 | B1 | 5/2004 | Presta |
| 7,183,387 | B1 | 2/2007 | Presta |
| 8,674,083 | B2 | 3/2014 | Presta |
| 9,090,696 | B2 | 7/2015 | Barrett et al. |
| 9,475,879 | B2 | 10/2016 | Suri et al. |
| 10,435,475 | B2 | 10/2019 | Honczarenko et al. |
| 11,220,550 | B2 | 1/2022 | Yamniuk et al. |
| 2005/0054832 | A1 | 3/2005 | Lazar et al. |
| 2006/0235208 | A1 | 10/2006 | Lazar et al. |
| 2007/0003546 | A1 | 1/2007 | Lazar et al. |
| 2008/0199471 | A1 | 8/2008 | Bernett et al. |
| 2010/0331208 | A1 | 12/2010 | Gao et al. |
| 2013/0149238 | A1 | 6/2013 | Kavlie |
| 2013/0209445 | A1 | 8/2013 | Lazar et al. |
| 2013/0236470 | A1 | 9/2013 | Matsuoka |
| 2014/0079701 | A1 | 3/2014 | Miller et al. |
| 2014/0099317 | A1 | 4/2014 | Suri et al. |
| 2014/0294812 | A1 | 10/2014 | Lazar |
| 2014/0335089 | A1 | 11/2014 | Igawa et al. |
| 2014/0363428 | A1 | 12/2014 | Igawa et al. |
| 2015/0018529 | A1 | 1/2015 | Humphreys et al. |
| 2015/0210763 | A1 | 7/2015 | Kuramochi et al. |
| 2015/0299296 | A1 | 10/2015 | Katada et al. |
| 2015/0315284 | A1 | 11/2015 | Lazar et al. |

(Continued)

FOREIGN PATENT DOCUMENTS

| CN | 102633880 A | 8/2012 |
| CN | 103172731 A | 6/2013 |

(Continued)

OTHER PUBLICATIONS

Adams, et al. (2005) "Development of a chimeric anti-CD40 monoclonal antibody that synergizes with LEA29Y to prolong islet allograft survival," *J. Immunol.* 174: 542-50.

(Continued)

*Primary Examiner* — Zachary C Howard

(74) *Attorney, Agent, or Firm* — Banner & Witcoff, LTD.

(57) ABSTRACT

The disclosure provides for antibodies that bind CD40, including a humanized antibody. The antibodies bind CD40 and do not exhibit CD40 agonist activity. The antibodies may comprise a modified IgG1 Fc domain, and exhibit minimal activation of immature dendritic cells. Compositions comprising antibodies, methods of use for treatment of diseases involving CD40 activity, and use in the preparation of a medicament for treatment of a disease involving CD40 activity are provided.

23 Claims, 10 Drawing Sheets

Specification includes a Sequence Listing.

(56) References Cited

U.S. PATENT DOCUMENTS

| | | |
|---|---|---|
| 2015/0337053 A1 | 11/2015 | McCarthy et al. |
| 2016/0039912 A1 | 2/2016 | Mimoto et al. |
| 2016/0075785 A1 | 3/2016 | Ast et al. |
| 2016/0145350 A1 | 5/2016 | Lonberg |
| 2016/0355596 A1 | 12/2016 | Honczarenko et al. |
| 2016/0376371 A1 | 12/2016 | Ravetch et al. |
| 2018/0340031 A1 | 11/2018 | Yamniuk et al. |
| 2020/0148779 A1 | 5/2020 | Yamniuk et al. |
| 2020/0157233 A1 | 5/2020 | Yamniuk et al. |
| 2021/0054090 A1 | 2/2021 | Yamniuk et al. |

FOREIGN PATENT DOCUMENTS

| | | |
|---|---|---|
| CN | 104788565 A | 7/2015 |
| EP | 2471813 B1 | 12/2014 |
| JP | 2008-505174 A | 2/2008 |
| JP | 2014-513953 A | 6/2017 |
| JP | 2018-526977 A | 9/2018 |
| WO | WO-2004/099249 A2 | 11/2004 |
| WO | WO-2006/019447 A1 | 2/2006 |
| WO | WO-2008/091954 A2 | 7/2008 |
| WO | WO-2008/137475 A2 | 11/2008 |
| WO | WO-2012/065950 A1 | 5/2012 |
| WO | WO-2012/145673 A1 | 10/2012 |
| WO | WO-2014/006217 A1 | 1/2014 |
| WO | WO-2014/184545 A2 | 11/2014 |
| WO | WO-2015/0134988 A1 | 9/2015 |
| WO | WO-2016/028810 A1 | 2/2016 |
| WO | WO-2016/196314 A1 | 12/2016 |
| WO | WO-2017/004006 A1 | 1/2017 |
| WO | WO-2017/004016 A1 | 1/2017 |
| WO | WO-2017/059196 A2 | 4/2017 |
| WO | WO-2018/065389 A1 | 4/2018 |
| WO | WO-2018/169993 A1 | 9/2018 |
| WO | WO-2018/175279 A2 | 9/2018 |
| WO | WO-2018/217976 A1 | 11/2018 |
| WO | WO-2018/217988 A1 | 11/2018 |
| WO | WO-2018/217988 A9 | 11/2018 |
| WO | WO-2018/218056 A1 | 11/2018 |
| WO | WO-2019087094 A1 | 5/2019 |
| WO | WO-2020/106620 A1 | 5/2020 |
| WO | WO-2020/112781 A1 | 6/2020 |

OTHER PUBLICATIONS

Cai et al. (2011) "C-terminal lysine processing of human immunoglobulin G2 heavy chain in vivo," *Biotechnol Bioeng.* 108(2): 404-12 (Abstract).

Davies et al. (2005) "TRAF6 Is Required for TRAF2-Dependent CD40 Signal Transduction in Nonhemopoietic Cells," *Mol. Cell Biol.* 25(22): 9806-19.

Hoogenboom et al. (1991) "Multi-subunit proteins on the surface of filamentous phage: methodologies for displaying antibody (Fab) heavy and light chains," *Nucleic Acids Res.* 19(15): 4133-4137.

Ristov et al. (2018) "Characterization of the in vitro and in vivo properties of CFZ533, a blocking and non-depleting anti-CD40 monoclonal antibody," *Am J Transplant.* 18(12):2895-2904. [Epub May 24, 2018].

Clinical Trials Feeds, "Study of HCD122 (Lucatumumab) and Bendamustine Combination Therapy in CD40+ Rituximab-Refractory Follicular Lymphoma," Internet at http:clinicaltrialsfeeds.org/clinical-trials/show/NCT01275209 (last updated Jan. 11, 2011).

Vonderheide et al. (2007) "Clinical activity and immune modulation in cancer patients treated with CP-870,893, a novel CD40 agonist monoclonal antibody," *J. Clin. Oncol.* 25(7): 876-883.

International Preliminary Report on Patentability dated Dec. 5, 2019 in International Application No. PCT/US2018/034315.

International Search Report dated Sep. 11, 2018 in International Application No. PCT/US2018/034315.

Written Opinion dated Sep. 11, 2018 in International Application No. PCT/US2018/034315.

Mimoto, F., et al., "Engineered antibody Fc variant with selectively enhanced FcγRIIb binding over both FcγRIIaR131 and FcγRIIaH131," *Protein Engineering, Design and Selection* 2001, 26(10): 589-598.

Yamniuk, Aaron, et al., "Modified IgG1 Fc Domains and Anti-CD40 Domain Antibody Fusions Therewith," filed May 24, 2018 (PCT/US18/34330), 95 pages.

International Preliminary Report on Patentability dated Dec. 5, 2019 in International Application No. PCT/US2018/034330.

Vidarsson, Gestur, et al., "IgG Subclasses and allotypes: from structure to effector functions," *Frontiers in Immunology*, vol. 5, Oct. 20, 2014, pp. 1-17.

International Search Report and Written Opinion dated Jul. 24, 2018 for PCT/US2018/034330.

International Preliminary Report on Patentability dated Jun. 3, 2021 in International Application No. PCT/US2019/062011.

Rowshanravan et al. 2018, "CTLA-4: a moving target in immunotherapy," *Blood* 131(1):58-97.

Melvin et al., 2012, "Belatacept: A worthy alternative to cyclosporine?" *J. Pharmacol Pharmacother.* 3(1): 90-92.

Ngo et al., "Computational Complexity, Protein Structure Prediction and the Levinthal Paradox," in: *The Protein Folding Problem and Tertiary Structure Prediction* (Boston, Birkhäuser, 1994), Chapter 14, pp. 434-495.

Wells, 1990, "Additivity of Mutational Effects in Proteins." *Biochemistry* 29(37): 8509-8517.

Nebija et al., "2-DE and MALDI-TOF-MS analysis of therapeutic fusion protein abatacept," *Electrophoresis* 31: 1438-1443, 2011.

International Search Report and the Written Opinion dated Apr. 9, 2020 in International Application No. PCT/US2019/062011.

Shields et al., (2001) "High Resolution Mapping of the Binding Site on Human IgG 1 for FcγRI, FcγRII, FcγRIII, and FcRn and Design of IgG1 Variants with Improved Binding to the FcγR*," The Journal of Biological Chemistry, vol. 276, No. 9, pp. 6591-6604.

First Office Action dated Sep. 3, 2021 in Chinese Patent Application No. 201880032964.0 (9 pages) with an English translation (11 pages).

Nov. 2, 20213—(WO) International Search Report and Written Opinion—App PCT/US2021/047610.

Fisher Benjamin A et al., "Assessment of the anti-CD40 antibody iscalimab in patients with primary Sjögren's syndrome: a multicentre, randomised, double-blind, placebo-controlled, proof-of-concept study", NL Mar. 3, 2020 (Mar. 3, 2020), vol. 2, No. 3, p. e142-e152, Retrieved from the Internet: URL:http://dx.doi.org/10.1016/S2665-9913(19)30135-3 XP055859370 DOI: 10.1016/S2665-9913(19)30135-3 external link ISSN:2665-9913.

Anonymous, "BMS-986325 in Healthy Participants and Participants With Primary Sjögren's Syndrome—Full Text View—ClinicalTrials.gov", Dec. 24, 2020 (Dec. 24m 2020), Retrieved from the Internet: URL:https://clinicaltrials.gov/ct2/show/NCT04684654 XP055859331 [retrieved on Nov. 9, 2021].

Anonymous, "Safety, Pharmacokinetics and Preliminary Efficacy Study of CFZ533 in Patients With Primary Sjögren's Syndrome—Full Text View—ClinicalTrials.gov", Nov. 14, 2014 (Nov. 14, 2014), Retrieved from the Internet: URL:https://clinicaltrials.gov/ct2/show/NCT02291029 XP055859384 [retrieved on Nov. 9, 2021].

Fisher Benjamin et al., "Abstract 1784: The Novel Anti-CD40 Monoclonal Antibody CFZ533 Shows Beneficial Effects in Patients with Primary Sjogren's Syndrome: A Phase IIa Double-Blind, PlaceboControlled Randomized Trial", Arthritis & Rheumatology, John Wiley & Sons, Inc, US,vol. 69, No. Suppl. 10, Sep. 18, 2017 (Sep. 18, 2017), XP002788011 ISSN:2326-5191.

Jobling Kerry et al., "CD40 as a therapeutic target in Sjögren's syndrome", GB Jul. 3, 2018 (Jul. 3, 2018), vol. 14, No. 7, p. 535-537, Retrieved from the Internet: URL:http://dx.doi.org/10.1080/1744666X.2018.1485492 XP055859366 DOI: 10.1080/1744666X.2018.1485492 external link ISSN:1744-666X.

Figure 1D

KD values for Antibody / FcγR interactions:

| Sample | Control-IgG1 | Y12XX-hz28-IgG1-P238K | Antibody B |
|---|---|---|---|
| hCD64 | 0.2 nM | 25 nM | 150 nM |
| hCD32a-H131 | 600 nM | >50 uM | >50 uM |
| hCD32a-R131 | 840 nM | >50 uM | >50 uM |
| hCD32b | 3.9 uM | >50 uM | >50 uM |
| hCD16a-V158 | 270 nM | >50 uM | 7 uM |
| hCD16a-F158 | 11 uM | >50 uM | >50 uM |

SEQUENCE LISTING

<160> NUMBER OF SEQ ID NOS: 120

<210> SEQ ID NO 1
<211> LENGTH: 5
<212> TYPE: PRT
<213> ORGANISM: Artificial Sequence
<220> FEATURE:
<223> OTHER INFORMATION: Synthetic polypeptide: VH-CDR1

<400> SEQUENCE: 1

Ser Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic polypeptide: VH-CDR2

<400> SEQUENCE: 2

Gln Ile Asn Pro Thr Thr Gly Arg Ser Gln Tyr Asn Glu Lys Phe Lys
1               5                   10                  15

Thr

<210> SEQ ID NO 3
<211> LENGTH: 8
<212> TYPE: PRT
<213> ORGANISM: Artificial Sequence
<220> FEATURE:
<223> OTHER INFORMATION: Synthetic polypeptide: VH-CDR3

<400> SEQUENCE: 3

Trp Gly Leu Gln Pro Phe Ala Tyr
1               5

<210> SEQ ID NO 4
<211> LENGTH: 117
<212> TYPE: PRT
<213> ORGANISM: Artificial Sequence
<220> FEATURE:
<223> OTHER INFORMATION: Synthetic polypeptide: Vh-hz14

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
                20                  25                  30

Trp Met His Trp Val Arg Gln Ala Pro Gly Gln Gly Leu Glu Trp Met
            35                  40                  45

Gly Gln Ile Asn Pro Thr Thr Gly Arg Ser Gln Tyr Asn Glu Lys Phe
        50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser
        115

<210> SEQ ID NO 5

<211> LENGTH: 446
<212> TYPE: PRT
<213> ORGANISM: Artificial Sequence
<220> FEATURE:
<223> OTHER INFORMATION: Synthetic polypeptide: HC_Y12XX-hz28-CH1-IgG1-
P238K (is IgG1 without C-terminal lysine)

<400> SEQUENCE: 5

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
```

```
              370                 375                 380
Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
            435                 440                 445

<210> SEQ ID NO 6
<211> LENGTH: 447
<212> TYPE: PRT
<213> ORGANISM: Artificial Sequence
<220> FEATURE:
<223> OTHER INFORMATION: Synthetic polypeptide: HC_Y12XX-hz28-CH1-IgG1-
      P238K (is IgG1 with C-terminal lysine)

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
                20                  25                  30

Trp Met His Trp Val Arg Gln Ala Pro Gly Gln Gly Leu Glu Trp Met
            35                  40                  45

Gly Gln Ile Asn Pro Thr Thr Gly Arg Ser Gln Tyr Asn Glu Lys Phe
        50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 7
<211> LENGTH: 11
<212> TYPE: PRT
<213> ORGANISM: Artificial Sequence
<220> FEATURE:
<223> OTHER INFORMATION: Synthetic polypeptide: VL-CDR1

<400> SEQUENCE: 7

Lys Ala Ser Gln Asp Val Ser Thr Ala Val Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic polypeptide: VL-CDR2

<400> SEQUENCE: 8

Ser Ala Ser Tyr Arg Tyr Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide: VL-CDR3

<400> SEQUENCE: 9

Gln Gln His Tyr Ser Thr Pro Trp Thr
1               5

<210> SEQ ID NO 10
<211> LENGTH: 107
<212> TYPE: PRT
<213> ORGANISM: Artificial Sequence
<220> FEATURE:
<223> OTHER INFORMATION: Synthetic polypeptide: Vk-hz2

<400> SEQUENCE: 10
```

-continued

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 11
<211> LENGTH: 214
<212> TYPE: PRT
<213> ORGANISM: Artificial Sequence
<220> FEATURE:
<223> OTHER INFORMATION: Synthetic polypeptide: LC_Y12XX-hz28

<400> SEQUENCE: 11

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 17
<212> TYPE: PRT
<213> ORGANISM: Artificial Sequence
<220> FEATURE:

<223> OTHER INFORMATION: Synthetic polypeptide: VH-CDR2 (Vh-hz12)

<400> SEQUENCE: 12

Gln Ile Asn Pro Ser Gln Gly Arg Ser Gln Tyr Asn Glu Lys Phe Lys
1               5                   10                  15

Thr

<210> SEQ ID NO 13
<211> LENGTH: 117
<212> TYPE: PRT
<213> ORGANISM: Artificial Sequence
<220> FEATURE:
<223> OTHER INFORMATION: Synthetic polypeptide: Vh-hz12

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
                20                  25                  30

Trp Met His Trp Val Arg Gln Ala Pro Gly Gln Gly Leu Glu Trp Met
            35                  40                  45

Gly Gln Ile Asn Pro Ser Gln Gly Arg Ser Gln Tyr Asn Glu Lys Phe
        50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser
        115

<210> SEQ ID NO 14
<211> LENGTH: 446
<212> TYPE: PRT
<213> ORGANISM: Artificial Sequence
<220> FEATURE:
<223> OTHER INFORMATION: Synthetic polypeptide: HC_Y12XX-hz40-P238K -
      IgG1a without C-terminal lysine

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
                20                  25                  30

Trp Met His Trp Val Arg Gln Ala Pro Gly Gln Gly Leu Glu Trp Met
            35                  40                  45

Gly Gln Ile Asn Pro Ser Gln Gly Arg Ser Gln Tyr Asn Glu Lys Phe
        50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys

```
            130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
            210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
            435                 440                 445

<210> SEQ ID NO 15
<211> LENGTH: 447
<212> TYPE: PRT
<213> ORGANISM: Artificial Sequence
<220> FEATURE:
<223> OTHER INFORMATION: Synthetic polypeptide: HC_Y12XX-hz40-P238K -
      IgG1a with C-terminal lysine

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
                20                  25                  30

Trp Met His Trp Val Arg Gln Ala Pro Gly Gln Gly Leu Glu Trp Met
            35                  40                  45
```

```
Gly Gln Ile Asn Pro Ser Gln Gly Arg Ser Gln Tyr Asn Glu Lys Phe
 50                  55                  60
Lys Thr Arg Val Thr Ile Thr Ala Asp Lys Ser Thr Ser Thr Ala Tyr
 65                      70                  75                  80
Met Glu Leu Ser Ser Leu Arg Ser Glu Asp Thr Ala Val Tyr Tyr Cys
                 85                  90                  95
Ala Arg Trp Gly Leu Gln Pro Phe Ala Tyr Trp Gly Gln Gly Thr Leu
             100                 105                 110
Val Thr Val Ser Ser Ala Ser Thr Lys Gly Pro Ser Val Phe Pro Leu
                 115                 120                 125
Ala Pro Ser Ser Lys Ser Thr Ser Gly Gly Thr Ala Ala Leu Gly Cys
 130                 135                 140
Leu Val Lys Asp Tyr Phe Pro Glu Pro Val Thr Val Ser Trp Asn Ser
 145                 150                 155                 160
Gly Ala Leu Thr Ser Gly Val His Thr Phe Pro Ala Val Leu Gln Ser
                 165                 170                 175
Ser Gly Leu Tyr Ser Leu Ser Ser Val Val Thr Val Pro Ser Ser Ser
                 180                 185                 190
Leu Gly Thr Gln Thr Tyr Ile Cys Asn Val Asn His Lys Pro Ser Asn
                 195                 200                 205
Thr Lys Val Asp Lys Arg Val Glu Pro Lys Ser Cys Asp Lys Thr His
 210                 215                 220
Thr Cys Pro Pro Cys Pro Ala Pro Glu Leu Leu Gly Gly Lys Ser Val
 225                 230                 235                 240
Phe Leu Phe Pro Pro Lys Pro Lys Asp Thr Leu Met Ile Ser Arg Thr
                 245                 250                 255
Pro Glu Val Thr Cys Val Val Val Asp Val Ser His Glu Asp Pro Glu
                 260                 265                 270
Val Lys Phe Asn Trp Tyr Val Asp Gly Val Glu Val His Asn Ala Lys
                 275                 280                 285
Thr Lys Pro Arg Glu Glu Gln Tyr Asn Ser Thr Tyr Arg Val Val Ser
                 290                 295                 300
Val Leu Thr Val Leu His Gln Asp Trp Leu Asn Gly Lys Glu Tyr Lys
 305                 310                 315                 320
Cys Lys Val Ser Asn Lys Ala Leu Pro Ala Pro Ile Glu Lys Thr Ile
                 325                 330                 335
Ser Lys Ala Lys Gly Gln Pro Arg Glu Pro Gln Val Tyr Thr Leu Pro
                 340                 345                 350
Pro Ser Arg Asp Glu Leu Thr Lys Asn Gln Val Ser Leu Thr Cys Leu
                 355                 360                 365
Val Lys Gly Phe Tyr Pro Ser Asp Ile Ala Val Glu Trp Glu Ser Asn
                 370                 375                 380
Gly Gln Pro Glu Asn Asn Tyr Lys Thr Thr Pro Val Leu Asp Ser
 385                 390                 395                 400
Asp Gly Ser Phe Phe Leu Tyr Ser Lys Leu Thr Val Asp Lys Ser Arg
                 405                 410                 415
Trp Gln Gln Gly Asn Val Phe Ser Cys Ser Val Met His Glu Ala Leu
                 420                 425                 430
His Asn His Tyr Thr Gln Lys Ser Leu Ser Leu Ser Pro Gly Lys
                 435                 440                 445

<210> SEQ ID NO 16
<211> LENGTH: 107
<212> TYPE: PRT
```

```
<213> ORGANISM: Artificial Sequence
<220> FEATURE:
<223> OTHER INFORMATION: Synthetic polypeptide: Vk-hz3

<400> SEQUENCE: 16

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 17
<211> LENGTH: 214
<212> TYPE: PRT
<213> ORGANISM: Artificial Sequence
<220> FEATURE:
<223> OTHER INFORMATION: Synthetic polypeptide: LC_Y12XX-hz40

<400> SEQUENCE: 17

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Tyr Ser Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 18
<211> LENGTH: 98
<212> TYPE: PRT
<213> ORGANISM: Artificial Sequence
<220> FEATURE:
<223> OTHER INFORMATION: Synthetic polypeptide: heavy chain CH1=amino
    acids 118-215 of SEQ ID NO: 5

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 19
<211> LENGTH: 107
<212> TYPE: PRT
<213> ORGANISM: Artificial Sequence
<220> FEATURE:
<223> OTHER INFORMATION: Synthetic polypeptide: light chain CL = amino
    acids 108-214 of SEQ ID NO: 11

<400> SEQUENCE: 19

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 20
<211> LENGTH: 277
<212> TYPE: PRT
<213> ORGANISM: Homo sapiens

<400> SEQUENCE: 20

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

```
Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 21
<211> LENGTH: 232
<212> TYPE: PRT
<213> ORGANISM: Artificial Sequence
<220> FEATURE:
<223> OTHER INFORMATION: Synthetic polypeptide: Fc consensus
<220> FEATURE:
<221> NAME/KEY: MOD_RES
<222> LOCATION: (23)..(23)
<223> OTHER INFORMATION: Pro or Lys
<220> FEATURE:
<221> NAME/KEY: MOD_RES
<222> LOCATION: (82)..(82)
<223> OTHER INFORMATION: Asn or Ala
<220> FEATURE:
<221> NAME/KEY: MOD_RES
<222> LOCATION: (141)..(141)
<223> OTHER INFORMATION: Asp or Glu
<220> FEATURE:
<221> NAME/KEY: MOD_RES
<222> LOCATION: (143)..(143)
<223> OTHER INFORMATION: Leu or Met
<220> FEATURE:
<221> NAME/KEY: MOD_RES
<222> LOCATION: (232)..(232)
<223> OTHER INFORMATION: Lys or absent

<400> SEQUENCE: 21

Glu Pro Lys Ser Cys Asp Lys Thr His Thr Cys Pro Pro Cys Pro Ala
1               5                   10                  15
```

-continued

```
Pro Glu Leu Leu Gly Gly Xaa Ser Val Phe Leu Phe Pro Pro Lys Pro
             20                  25                  30

Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
     50                  55                  60

Asp Gly Val Glu Val His Asn Ala Lys Thr Lys Pro Arg Glu Glu Gln
65                  70                  75                  80

Tyr Xaa Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Xaa Glu Xaa Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Xaa
225                 230

<210> SEQ ID NO 22
<211> LENGTH: 231
<212> TYPE: PRT
<213> ORGANISM: Artificial Sequence
<220> FEATURE:
<223> OTHER INFORMATION: Synthetic polypeptide: IgG1-P238K(-C-term Lys)

<400> SEQUENCE: 22

Glu Pro Lys Ser Cys Asp Lys Thr His Thr Cys Pro Pro Cys Pro Ala
1               5                  10                  15

Pro Glu Leu Leu Gly Gly Lys Ser Val Phe Leu Phe Pro Pro Lys Pro
             20                  25                  30

Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
     50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly
225                 230
```

<210> SEQ ID NO 23
<211> LENGTH: 232
<212> TYPE: PRT
<213> ORGANISM: Artificial Sequence
<220> FEATURE:
<223> OTHER INFORMATION: Synthetic polypeptide: IgG1-P238K

<400> SEQUENCE: 23

```
Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```

<210> SEQ ID NO 24
<211> LENGTH: 329
<212> TYPE: PRT
<213> ORGANISM: Artificial Sequence
<220> FEATURE:

<223> OTHER INFORMATION: Synthetic polypeptide: CH1-IgG1-P238K(-C-term Lys)

<400> SEQUENCE: 24

| Ala | Ser | Thr | Lys | Gly | Pro | Ser | Val | Phe | Pro | Leu | Ala | Pro | Ser | Ser | Lys |
|---|---|---|---|---|---|---|---|---|---|---|---|---|---|---|---|
| 1 | | | | 5 | | | | | 10 | | | | | 15 | |

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 25
<211> LENGTH: 330
<212> TYPE: PRT
<213> ORGANISM: Artificial Sequence
<220> FEATURE:
<223> OTHER INFORMATION: Synthetic polypeptide: CH1-IgG1-P238K

<400> SEQUENCE: 25

Ala Ser Thr Lys Gly Pro Ser Val Phe Pro Leu Ala Pro Ser Ser Lys

```
            1               5                  10                 15
        Ser Thr Ser Gly Gly Thr Ala Ala Leu Gly Cys Leu Val Lys Asp Tyr
                    20                  25                 30

Phe Pro Glu Pro Val Thr Val Ser Trp Asn Ser Gly Ala Leu Thr Ser
                    35                  40                 45

Gly Val His Thr Phe Pro Ala Val Leu Gln Ser Ser Gly Leu Tyr Ser
                    50                  55                 60

Leu Ser Ser Val Val Thr Val Pro Ser Ser Leu Gly Thr Gln Thr
        65                  70                  75                 80

Tyr Ile Cys Asn Val Asn His Lys Pro Ser Asn Thr Lys Val Asp Lys
                        85                  90                 95

Arg Val Glu Pro Lys Ser Cys Asp Lys Thr His Thr Cys Pro Pro Cys
                    100                 105                110

Pro Ala Pro Glu Leu Leu Gly Gly Lys Ser Val Phe Leu Phe Pro Pro
                    115                 120                125

Lys Pro Lys Asp Thr Leu Met Ile Ser Arg Thr Pro Glu Val Thr Cys
                    130                 135                140

Val Val Val Asp Val Ser His Glu Asp Pro Glu Val Lys Phe Asn Trp
        145                 150                 155                160

Tyr Val Asp Gly Val Glu Val His Asn Ala Lys Thr Lys Pro Arg Glu
                        165                 170                175

Glu Gln Tyr Asn Ser Thr Tyr Arg Val Val Ser Val Leu Thr Val Leu
                    180                 185                190

His Gln Asp Trp Leu Asn Gly Lys Glu Tyr Lys Cys Lys Val Ser Asn
                    195                 200                205

Lys Ala Leu Pro Ala Pro Ile Glu Lys Thr Ile Ser Lys Ala Lys Gly
                    210                 215                220

Gln Pro Arg Glu Pro Gln Val Tyr Thr Leu Pro Pro Ser Arg Asp Glu
        225                 230                 235                240

Leu Thr Lys Asn Gln Val Ser Leu Thr Cys Leu Val Lys Gly Phe Tyr
                        245                 250                255

Pro Ser Asp Ile Ala Val Glu Trp Glu Ser Asn Gly Gln Pro Glu Asn
                    260                 265                270

Asn Tyr Lys Thr Thr Pro Pro Val Leu Asp Ser Asp Gly Ser Phe Phe
                    275                 280                285

Leu Tyr Ser Lys Leu Thr Val Asp Lys Ser Arg Trp Gln Gln Gly Asn
                    290                 295                300

Val Phe Ser Cys Ser Val Met His Glu Ala Leu His Asn His Tyr Thr
        305                 310                 315                320

Gln Lys Ser Leu Ser Leu Ser Pro Gly Lys
                        325                 330

<210> SEQ ID NO 26
<211> LENGTH: 231
<212> TYPE: PRT
<213> ORGANISM: Artificial Sequence
<220> FEATURE:
<223> OTHER INFORMATION: Synthetic polypeptide: IgG1f-P238K(-C-term Lys)

<400> SEQUENCE: 26

Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
            20                  25                  30

Lys Asp Thr Leu Met Ile Ser Arg Thr Pro Glu Val Thr Cys Val Val
```

```
                35                  40                  45
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 27
<211> LENGTH: 232
<212> TYPE: PRT
<213> ORGANISM: Artificial Sequence
<220> FEATURE:
<223> OTHER INFORMATION: Synthetic polypeptide: IgG1f-P238K

<400> SEQUENCE: 27

Glu Pro Lys Ser Cys Asp Lys Thr His Thr Cys Pro Pro Cys Pro Ala
 1               5                  10                  15

Pro Glu Leu Leu Gly Gly Lys Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

165                 170                 175

Lys Thr Thr Pro Pro Val Leu Asp Ser Asp Gly Ser Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 28
<211> LENGTH: 329
<212> TYPE: PRT
<213> ORGANISM: Artificial Sequence
<220> FEATURE:
<223> OTHER INFORMATION: Synthetic polypeptide: CH1-IgG1f-P238K(-C-term Lys)

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 29
<211> LENGTH: 330
<212> TYPE: PRT
<213> ORGANISM: Artificial Sequence
<220> FEATURE:
<223> OTHER INFORMATION: Synthetic polypeptide: CH1-IgG1f-P238K

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

```
Gln Lys Ser Leu Ser Leu Ser Pro Gly Lys
                325                 330
```

<210> SEQ ID NO 30
<211> LENGTH: 446
<212> TYPE: PRT
<213> ORGANISM: Artificial Sequence
<220> FEATURE:
<223> OTHER INFORMATION: Synthetic polypeptide: HC_Y12XX-hz28-CH1-IgG1f-
      P238K- no terminal lysine)

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 31
<211> LENGTH: 447
<212> TYPE: PRT
<213> ORGANISM: Artificial Sequence
<220> FEATURE:
<223> OTHER INFORMATION: Synthetic polypeptide: HC_Y12XX-hz28-CH1-IgG1f-
      P238K- with terminal lysine)

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
```

```
                    260                 265                 270
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 32
<211> LENGTH: 231
<212> TYPE: PRT
<213> ORGANISM: Artificial Sequence
<220> FEATURE:
<223> OTHER INFORMATION: Synthetic polypeptide: IgG1-N297A(-C-term Lys)

<400> SEQUENCE: 32

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
```

```
                    180                 185                 190
Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly
225                 230

<210> SEQ ID NO 33
<211> LENGTH: 232
<212> TYPE: PRT
<213> ORGANISM: Artificial Sequence
<220> FEATURE:
<223> OTHER INFORMATION: Synthetic polypeptide: IgG1-N297A

<400> SEQUENCE: 33

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 34
<211> LENGTH: 329
<212> TYPE: PRT
<213> ORGANISM: Artificial Sequence
<220> FEATURE:
<223> OTHER INFORMATION: Synthetic polypeptide: CH1-IgG1-N297A(-C-term
      Lys)

<400> SEQUENCE: 34

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 35
<211> LENGTH: 330
<212> TYPE: PRT
<213> ORGANISM: Artificial Sequence
<220> FEATURE:
<223> OTHER INFORMATION: Synthetic polypeptide: CH1-IgG1-N297A

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 231
<212> TYPE: PRT
<213> ORGANISM: Artificial Sequence
<220> FEATURE:
<223> OTHER INFORMATION: Synthetic polypeptide: IgG1f-N297A(-C-term Lys)

<400> SEQUENCE: 36

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
         50                  55                  60

Asp Gly Val Glu Val His Asn Ala Lys Thr Lys Pro Arg Glu Glu Gln
 65                  70                  75                  80

```
Tyr Ala Ser Thr Tyr Arg Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 37
<211> LENGTH: 232
<212> TYPE: PRT
<213> ORGANISM: Artificial Sequence
<220> FEATURE:
<223> OTHER INFORMATION: Synthetic polypeptide: IgG1f-N297A

<400> SEQUENCE: 37

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 38
<211> LENGTH: 329
<212> TYPE: PRT
<213> ORGANISM: Artificial Sequence
<220> FEATURE:
<223> OTHER INFORMATION: Synthetic polypeptide: CH1-IgG1f-N297A(-C-term
      Lys)

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly

<210> SEQ ID NO 39
<211> LENGTH: 330
<212> TYPE: PRT
<213> ORGANISM: Artificial Sequence
<220> FEATURE:
<223> OTHER INFORMATION: Synthetic polypeptide: CH1-IgG1f-N297A

<400> SEQUENCE: 39

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 40
<211> LENGTH: 5
<212> TYPE: PRT

```
<213> ORGANISM: Artificial Sequence
<220> FEATURE:
<223> OTHER INFORMATION: Synthetic polypeptide: Linker

<400> SEQUENCE: 40

Gly Gly Gly Gly Ser
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic polypeptide: Linker

<400> SEQUENCE: 41

Gly Gly Gly Gly Ser Gly Gly Gly Gly Ser
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Synthetic polypeptide: Linker

<400> SEQUENCE: 42

Gly Gly Gly Gly Ser Gly Gly Gly Gly Ser Gly Gly Gly Gly Ser
1               5                   10                  15

<210> SEQ ID NO 43
<211> LENGTH: 20
<212> TYPE: PRT
<213> ORGANISM: Artificial Sequence
<220> FEATURE:
<223> OTHER INFORMATION: Synthetic polypeptide: Linker

<400> SEQUENCE: 43

Gly Gly Gly Gly Ser Gly Gly Gly Gly Ser Gly Gly Gly Gly Ser Gly
1               5                   10                  15

Gly Gly Gly Ser
            20

<210> SEQ ID NO 44
<211> LENGTH: 25
<212> TYPE: PRT
<213> ORGANISM: Artificial Sequence
<220> FEATURE:
<223> OTHER INFORMATION: Synthetic polypeptide: Linker

<400> SEQUENCE: 44

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 45
<211> LENGTH: 3
<212> TYPE: PRT
<213> ORGANISM: Artificial Sequence
<220> FEATURE:
<223> OTHER INFORMATION: Synthetic polypeptide: Linker

<400> SEQUENCE: 45

Ala Ser Thr
1
```

<210> SEQ ID NO 46
<211> LENGTH: 6
<212> TYPE: PRT
<213> ORGANISM: Artificial Sequence
<220> FEATURE:
<223> OTHER INFORMATION: Synthetic polypeptide: Linker

<400> SEQUENCE: 46

Thr Val Ala Ala Pro Ser
1               5

<210> SEQ ID NO 47
<211> LENGTH: 3
<212> TYPE: PRT
<213> ORGANISM: Artificial Sequence
<220> FEATURE:
<223> OTHER INFORMATION: Synthetic polypeptide: Linker

<400> SEQUENCE: 47

Thr Val Ala
1

<210> SEQ ID NO 48
<211> LENGTH: 7
<212> TYPE: PRT
<213> ORGANISM: Artificial Sequence
<220> FEATURE:
<223> OTHER INFORMATION: Synthetic polypeptide: Linker

<400> SEQUENCE: 48

Ala Ser Thr Ser Gly Pro Ser
1               5

<210> SEQ ID NO 49
<211> LENGTH: 1392
<212> TYPE: DNA
<213> ORGANISM: Artificial Sequence
<220> FEATURE:
<223> OTHER INFORMATION: Synthetic polypeptide: representative nucleic
      acid sequence encoding the Y12XX heavy chain variable domain of
      Y12XX-hz28 including a constant region CH1 and Fc domain IgG1-
      P238K

<400> SEQUENCE: 49
atgagggctt ggatcttctt tctgctctgc ctggccggga gagcgctcgc acaggtgcag      60
ctggtgcagt ctggtgccga ggtcaaaaag ccaggctcca gcgtgaaggt gagctgcaag     120
gcctctggct acgctttcac ctcttattgg atgcactggg tgagacaggc tcctggacag     180
ggcctggagt ggatgggcca gatcaaccca accaccggca agccagta caatgagaag      240 tttaagaccc gcgtgaccat cacagccgac aagtccacca gcacagctta tatggagctg     300
tcttccctga ggtccgagga tacagccgtg tactattgcg ctcggtgggg cctgcagcct     360
ttcgcttact ggggccaggg caccctggtg acagtgagct ctgctagcac caagggccca     420
tcggtcttcc ccctggcacc ctcctccaag agcacctctg ggggcacagc ggccctgggc     480
tgcctggtca aggactactt ccccgaaccg gtgacggtgt cgtggaactc aggcgccctg     540
accagcggcg tgcacacctt cccggccgtc ctacagtcct caggactcta ctccctcagc     600
agcgtggtga ccgtgccctc cagcagcttg ggcacccaga cctacatctg caacgtgaat     660
cacaagccca gcaacaccaa ggtggacaag agagttgagc ccaaatcttg tgacaaaact     720
cacacatgcc caccgtgccc agcacctgaa ctcctggggg gaaagtcagt cttcctcttc     780

```
ccccaaaac caaggacac cctcatgatc tcccggaccc ctgaggtcac atgcgtggtg    840
gtggacgtga gccacgaaga ccctgaggtc aagttcaact ggtacgtgga cggcgtggag    900
gtgcataatg ccaagacaaa gccgcgggag gagcagtaca acagcacgta ccgtgtggtc    960
agcgtcctca ccgtcctgca ccaggactgg ctgaatggca aggagtacaa gtgcaaggtc    1020
tccaacaaag ccctcccagc ccccatcgag aaaaccatct ccaaagccaa agggcagccc    1080
cgagaaccac aggtgtacac cctgccccca tcccgggatg agctgaccaa gaaccaggtc    1140
agcctgacct gcctggtcaa aggcttctat cccagcgaca tcgccgtgga gtgggagagc    1200
aatgggcagc cggagaacaa ctacaagacc acgcctcccg tgctggactc cgacggctcc    1260
ttcttcctct acagcaagct caccgtggac aagagcaggt ggcagcaggg gaacgtcttc    1320
tcatgctccg tgatgcatga ggctctgcac aaccactaca cgcagaagag cctctccctg    1380
tctccgggtt ga    1392
```

<210> SEQ ID NO 50
<211> LENGTH: 696
<212> TYPE: DNA
<213> ORGANISM: Artificial Sequence
<220> FEATURE:
<223> OTHER INFORMATION: Synthetic polypeptide: representative nucleic
    acid sequence encoding the Y12XX light chain variable domain of
    Y12XX-hz28 including a constant region CL

<400> SEQUENCE: 50

```
atgagggctt ggatcttctt tctgctctgc ctggccgggc gcgccttggc cgacatccag    60
atgacccagt cccctccctt cctgtctgcc tccgtgggcg acagagtgac catcacctgt    120
aaggcttccc aggatgtgag cacagccgtg gcttggtacc agcagaagcc aggcaaggcc    180 ccaagctgc tgatctattc cgcctcttac aggtataccg gcgtgccctc tcggttctcc    240
ggcagcggct ctggcacaga ctttaccctg acaatctcca gcctgcagcc tgaggatttc    300
gccacctact attgccagca gcactactcc accccatgga catttggcgg cggcaccaag    360
gtggagatca agcgtacggt ggctgcacca tctgtcttca tcttcccgcc atctgatgag    420
cagttgaaat ctggaactgc ctctgttgtg tgcctgctga ataacttcta tcccagagag    480
gccaaagtac agtggaaggt ggataacgcc ctccaatcgg gtaactccca ggagagtgtc    540
acagagcagg acagcaagga cagcacctac agcctcagca gcaccctgac gctgagcaaa    600
gcagactacg agaaacacaa agtctacgcc tgcgaagtca cccatcaggg cctgagctcg    660
cccgtcacaa agagcttcaa caggggagag tgttag    696
```

<210> SEQ ID NO 51
<211> LENGTH: 17
<212> TYPE: PRT
<213> ORGANISM: Artificial Sequence
<220> FEATURE:
<223> OTHER INFORMATION: Synthetic polypeptide: signal peptide

<400> SEQUENCE: 51

```
Met Arg Ala Trp Ile Phe Phe Leu Leu Cys Leu Ala Gly Arg Ala Leu
1               5                   10                  15

Ala
```

<210> SEQ ID NO 52
<211> LENGTH: 51
<212> TYPE: DNA
<213> ORGANISM: Artificial Sequence
<220> FEATURE:

<223> OTHER INFORMATION: Synthetic polypeptide: coding sequence for
      signal peptide

<400> SEQUENCE: 52
atgagggctt ggatcttctt tctgctctgc ctggccggga gagcgctcgc a          51

<210> SEQ ID NO 53
<211> LENGTH: 126
<212> TYPE: PRT
<213> ORGANISM: Artificial Sequence
<220> FEATURE:
<223> OTHER INFORMATION: Synthetic polypeptide: ADX_Y1060.ZZ0-1-Vh

<400> SEQUENCE: 53

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser
        115                 120                 125

<210> SEQ ID NO 54
<211> LENGTH: 122
<212> TYPE: PRT
<213> ORGANISM: Artificial Sequence
<220> FEATURE:
<223> OTHER INFORMATION: Synthetic polypeptide: ADX_Y1072.ZZ0-1-Vh

<400> SEQUENCE: 54

Gln Val Gln Phe Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Ser Arg Tyr Asn Gln Lys Phe
    50                  55                  60

Lys Gly Lys Ala Leu Leu Thr Ala Asp Lys Ser Ser Ser Ile Ala Tyr
65                  70                  75                  80

Met Gln Leu Asn Ser Leu Ala Ser Glu Asp Ser Ala Val Tyr Phe Cys
                85                  90                  95

Ala Arg Phe Ser Leu Tyr Asp Gly Tyr Pro Tyr Tyr Phe Asp Tyr Trp
            100                 105                 110

Gly Gln Gly Thr Thr Leu Thr Val Ser Ser
        115                 120

<210> SEQ ID NO 55
<211> LENGTH: 118
<212> TYPE: PRT

<213> ORGANISM: Artificial Sequence
<220> FEATURE:
<223> OTHER INFORMATION: Synthetic polypeptide: ADX_Y1234.ZZ0-1-Vh

<400> SEQUENCE: 55

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Asn Ser Gly Val Gly Asn Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Gly Asn Tyr Ala Trp Phe Ala Tyr Trp Gly Gln Gly Thr
            100                 105                 110

Leu Val Thr Val Ser Ala
        115

<210> SEQ ID NO 56
<211> LENGTH: 117
<212> TYPE: PRT
<213> ORGANISM: Artificial Sequence
<220> FEATURE:
<223> OTHER INFORMATION: Synthetic polypeptide: ADX_Y1236.ZZ0-1-Vh

<400> SEQUENCE: 56

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Tyr Gly Asn Tyr Ala Met Asp Tyr Trp Gly Gln Gly Thr Ser
            100                 105                 110

Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: Synthetic polypeptide: ADX_Y1238.ZZ0-1-Vh

<400> SEQUENCE: 57

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

```
Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Asp Ser Ala Val Tyr Phe Cys
                85                  90                  95

Ala Arg Ser Gln Leu Gly Arg Arg Phe Asp Tyr Trp Gly Gln Gly Thr
            100                 105                 110

Thr Leu Thr Val Ser Ser
            115

<210> SEQ ID NO 58
<211> LENGTH: 115
<212> TYPE: PRT
<213> ORGANISM: Artificial Sequence
<220> FEATURE:
<223> OTHER INFORMATION: Synthetic polypeptide: ADX_Y1241.ZZ0-1-Vh

<400> SEQUENCE: 58

Glu Phe Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Ile Ile Gln Trp Val Lys Gln Pro Gly Gln Gly Leu Glu Trp Ile
        35                  40                  45

Gly Tyr Ile Asn Pro Tyr Ser Ser Glu Thr Asn Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Ile Tyr Phe Cys
                85                  90                  95

Ala Arg Asp Leu Ile Gly Asn Tyr Trp Gly Gln Gly Thr Thr Leu Thr
            100                 105                 110

Val Ser Ser
    115

<210> SEQ ID NO 59
<211> LENGTH: 117
<212> TYPE: PRT
<213> ORGANISM: Artificial Sequence
<220> FEATURE:
<223> OTHER INFORMATION: Synthetic polypeptide: ADX_Y1242.ZZ0-1-Vh

<400> SEQUENCE: 59

Glu Phe Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Ser Tyr
            20                  25                  30

Val Met His Trp Val Lys Gln Lys Pro Gly Gln Ala Leu Glu Trp Ile
        35                  40                  45

Gly Tyr Ile Asn Pro Ser Asn Asp Gly Ser Glu Tyr Asn Glu Arg Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
```

```
                85                  90                  95
Ala Arg Trp Ala Pro Tyr Pro Phe Ala Tyr Trp Gly Gln Gly Thr Leu
            100                 105                 110

Val Thr Val Ser Ala
        115

<210> SEQ ID NO 60
<211> LENGTH: 120
<212> TYPE: PRT
<213> ORGANISM: Artificial Sequence
<220> FEATURE:
<223> OTHER INFORMATION: Synthetic polypeptide: ADX_Y1249.ZZ0-1-Vh

<400> SEQUENCE: 60

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asp Pro Ser Ser His Tyr Thr Asn Tyr Asn Gln Lys Phe
    50                  55                  60

Lys Gly Thr Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Arg Tyr Ala Tyr Trp Tyr Phe Asp Val Trp Gly Ala
            100                 105                 110

Gly Thr Thr Leu Thr Val Ser Ser
        115                 120

<210> SEQ ID NO 61
<211> LENGTH: 117
<212> TYPE: PRT
<213> ORGANISM: Artificial Sequence
<220> FEATURE:
<223> OTHER INFORMATION: Synthetic polypeptide: ADX_Y1256.ZZ0-1-Vh

<400> SEQUENCE: 61

Gln Val Gln Leu Gln Gln Ser Gly Ala Glu Leu Ala Lys Pro Gly Ser
1               5                   10                  15

Ser Val Lys Met Ser Cys Lys Ala Ser Gly Tyr Ala Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Thr Thr Gly Tyr Ser Ala Tyr Asn Gln Lys Phe
    50                  55                  60

Lys Asp Lys Ala Thr Leu Thr Ala Asp Lys Ser Ser Ser Thr Ala Tyr
65                  70                  75                  80

Leu Gln Leu Thr Ser Leu Thr Ser Glu Asp Ser Ala Val Tyr Phe Cys
                85                  90                  95

Ser Arg Trp Gly Leu Pro Pro Phe Ala Tyr Trp Gly Gln Gly Thr Leu
            100                 105                 110

Val Thr Val Ser Ala
        115

<210> SEQ ID NO 62
<211> LENGTH: 117
```

```
<212> TYPE: PRT
<213> ORGANISM: Artificial Sequence
<220> FEATURE:
<223> OTHER INFORMATION: Synthetic polypeptide: ADX_Y1257.ZZ0-1-Vh

<400> SEQUENCE: 62

Gln Val Gln Leu Gln Gln Ser Gly Ala Glu Leu Ala Lys Pro Gly Ser
1               5                   10                  15

Ser Val Lys Met Ser Cys Lys Ala Ser Gly Tyr Ala Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Thr Thr Gly Tyr Ser Ala Tyr Asn Gln Lys Phe
    50                  55                  60

Lys Ala Lys Thr Thr Leu Thr Ala Asp Lys Ser Ser Ser Thr Ala Tyr
65                  70                  75                  80

Met Gln Leu Thr Ser Leu Thr Phe Glu Asp Ser Ala Val Tyr Phe Cys
                85                  90                  95

Ser Arg Trp Gly Leu Pro Pro Phe Ala Tyr Trp Gly Gln Gly Thr Leu
            100                 105                 110

Val Thr Val Ser Ala
            115

<210> SEQ ID NO 63
<211> LENGTH: 117
<212> TYPE: PRT
<213> ORGANISM: Artificial Sequence
<220> FEATURE:
<223> OTHER INFORMATION: Synthetic polypeptide: ADX_Y1258.ZZ0-1-Vh

<400> SEQUENCE: 63

Gln Val Gln Leu Gln Gln Ser Gly Ala Glu Leu Ala Lys Pro Gly Ser
1               5                   10                  15

Ser Val Lys Met Ser Cys Lys Ala Ser Gly Tyr Ala Phe Thr Ser Tyr
            20                  25                  30

Trp Met His Trp Ile Lys Gln Arg Pro Gly Gln Gly Leu Glu Trp Ile
        35                  40                  45

Gly Phe Ile Asn Pro Thr Thr Gly Tyr Ser Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Trp Gly Leu Pro Pro Phe Ala Tyr Trp Gly Gln Gly Thr Leu
            100                 105                 110

Val Thr Val Ser Ala
            115

<210> SEQ ID NO 64
<211> LENGTH: 117
<212> TYPE: PRT
<213> ORGANISM: Artificial Sequence
<220> FEATURE:
<223> OTHER INFORMATION: Synthetic polypeptide: ADX_Y1259.ZZ0-1-Vh

<400> SEQUENCE: 64

Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Ser Phe Thr Ser Tyr
```

```
                    20                  25                  30

Trp Met His Trp Ile Lys Gln Arg Pro Gly Gln Gly Leu Glu Trp Ile
            35                  40                  45

Gly Phe Ile Asn Pro Thr Thr Gly Tyr Thr Glu Tyr Asn Gln Lys Phe
        50                  55                  60

Lys Asp Lys Ala Thr Leu Thr Ala Asp Lys Ser Ser Thr Ala Tyr
65                  70                  75                  80

Met Gln Leu Ser Ser Leu Ser Ser Glu Asp Ser Ala Val Tyr Tyr Cys
                85                  90                  95

Ser Arg Trp Gly Leu Pro Pro Phe Ala Tyr Trp Gly Gln Gly Thr Leu
            100                 105                 110

Val Thr Val Ser Ala
        115

<210> SEQ ID NO 65
<211> LENGTH: 117
<212> TYPE: PRT
<213> ORGANISM: Artificial Sequence
<220> FEATURE:
<223> OTHER INFORMATION: Synthetic polypeptide: ADX_Y1260.ZZ0-1-Vh

<400> SEQUENCE: 65

Gln Val Gln Leu Gln Gln Ser Gly Ala Glu Leu Thr Lys Pro Gly Ala
1               5                   10                  15

Ser Val Lys Met Ser Cys Lys Ala Ser Gly Tyr Ser Phe Thr Ser Tyr
                20                  25                  30

Trp Met His Trp Val Lys Gln Arg Pro Gly Gln Gly Leu Glu Trp Ile
            35                  40                  45

Gly Ser Ile Asn Pro Ser Thr Gly Tyr Thr Glu Asp Asn Gln Lys Phe
        50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Leu Pro Pro Phe Ala Tyr Trp Gly Gln Gly Thr Leu
            100                 105                 110

Val Thr Val Ser Ala
        115

<210> SEQ ID NO 66
<211> LENGTH: 117
<212> TYPE: PRT
<213> ORGANISM: Artificial Sequence
<220> FEATURE:
<223> OTHER INFORMATION: Synthetic polypeptide: ADX_Y1261.ZZ0-1-Vh

<400> SEQUENCE: 66

Gln Val Gln Leu Gln Gln Ser Gly Ala Glu Arg Ala Lys Pro Gly Ala
1               5                   10                  15

Ser Val Lys Met Ser Cys Lys Ala Ser Gly Tyr Ser Phe Thr Ser Tyr
                20                  25                  30

Trp Met His Trp Ile Lys Gln Arg Pro Gly Gln Gly Leu Glu Trp Ile
            35                  40                  45

Gly Phe Ile Asn Pro Asn Thr Gly His Thr Asp Tyr Asn Gln Lys Phe
        50                  55                  60

Lys Asp Lys Ala Thr Leu Thr Ala Asp Lys Ser Ser Thr Ala Tyr
65                  70                  75                  80
```

Met Gln Leu Ser Ser Leu Thr Ser Glu Asp Ser Ala Val Tyr Phe Cys
                85                  90                  95

Ser Arg Trp Gly Leu Pro Pro Phe Ala Tyr Trp Gly Gln Gly Thr Leu
            100                 105                 110

Val Thr Val Ser Ala
        115

<210> SEQ ID NO 67
<211> LENGTH: 117
<212> TYPE: PRT
<213> ORGANISM: Artificial Sequence
<220> FEATURE:
<223> OTHER INFORMATION: Synthetic polypeptide: ADX_Y1262.ZZ0-1-Vh

<400> SEQUENCE: 67

Gln Val Gln Leu Gln Gln Ser Gly Ala Glu Leu Ala Lys Pro Gly Ser
1               5                   10                  15

Ser Val Lys Met Ser Cys Lys Ala Ser Gly Tyr Ala Phe Thr Ser Tyr
                20                  25                  30

Trp Met His Trp Val Lys Gln Arg Pro Gly Gln Gly Leu Glu Trp Ile
            35                  40                  45

Gly Tyr Ile Asn Pro Thr Thr Gly Tyr Ser Ala Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Asp Pro Arg Pro Phe Ala Tyr Trp Gly Gln Gly Thr Leu
            100                 105                 110

Val Thr Val Ser Ala
        115

<210> SEQ ID NO 68
<211> LENGTH: 117
<212> TYPE: PRT
<213> ORGANISM: Artificial Sequence
<220> FEATURE:
<223> OTHER INFORMATION: Synthetic polypeptide: ADX_Y1263.ZZ0-1-Vh

<400> SEQUENCE: 68

Gln Val Gln Leu Gln Gln Ser Gly Ala Glu Leu Ala Lys Pro Gly Thr
1               5                   10                  15

Ser Val Lys Met Ser Cys Lys Ala Ser Gly Tyr Ser Phe Thr Ser Tyr
                20                  25                  30

Trp Val His Trp Val Lys Glu Arg Pro Gly Gln Gly Leu Glu Trp Ile
            35                  40                  45

Gly His Thr Asn Pro Asn Thr Gly Tyr Thr Glu Tyr Asn Gln Lys Phe
        50                  55                  60

Lys Asp Lys Ala Thr Leu Thr Val Asp Arg Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Asp Pro Arg Pro Phe Ala Tyr Trp Gly Gln Gly Thr Leu
            100                 105                 110

Val Thr Val Ser Ala
        115

<210> SEQ ID NO 69

```
<211> LENGTH: 117
<212> TYPE: PRT
<213> ORGANISM: Artificial Sequence
<220> FEATURE:
<223> OTHER INFORMATION: Synthetic polypeptide: ADX_Y1264.ZZ0-1-Vh

<400> SEQUENCE: 69

Glu Val Gln Leu Gln Gln Ser Gly Thr Val Leu Ala Arg Pro Gly Ala
1               5                   10                  15

Ser Val Lys Met Ser Cys Arg Ala Ser Gly Tyr Ser Phe Ser Ser Tyr
            20                  25                  30

Trp Met His Trp Val Lys Gln Arg Pro Gly Gln Gly Leu Glu Trp Ile
        35                  40                  45

Gly Ser Ile Asn Pro Gly Asn Ser Asp Ala Phe Tyr Asn Gln Gln Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Trp Gly Leu Pro Pro Phe Ala Tyr Trp Gly Gln Gly Thr Leu
            100                 105                 110

Val Thr Val Ser Ala
            115

<210> SEQ ID NO 70
<211> LENGTH: 117
<212> TYPE: PRT
<213> ORGANISM: Artificial Sequence
<220> FEATURE:
<223> OTHER INFORMATION: Synthetic polypeptide: ADX_Y1265.ZZ0-1-Vh

<400> SEQUENCE: 70

Glu Val Gln Leu Gln Gln Ser Gly Thr Val Leu Ala Gly Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Asp Leu Glu Trp Ile
        35                  40                  45

Gly Thr Ile Asn Pro Gly Lys Gly Asp Ser Asn Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Trp Gly Leu Pro Pro Phe Ala Tyr Trp Gly Gln Gly Thr Leu
            100                 105                 110

Val Thr Val Ser Ala
            115

<210> SEQ ID NO 71
<211> LENGTH: 117
<212> TYPE: PRT
<213> ORGANISM: Artificial Sequence
<220> FEATURE:
<223> OTHER INFORMATION: Synthetic polypeptide: ADX_Y1266.ZZ0-1-Vh

<400> SEQUENCE: 71

Gln Val Gln Leu Gln Gln Pro Gly Ala Glu Leu Val Lys Pro Gly Ala
1               5                   10                  15
```

-continued

Ser Val Arg Leu Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Gln Ile Asn Pro Ser Asn Gly Arg Thr Gln Tyr Asn Glu Lys Phe
    50                  55                  60

Lys Ser Met Ala Thr Leu Thr Val Asp Lys Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ala
        115

<210> SEQ ID NO 72
<211> LENGTH: 117
<212> TYPE: PRT
<213> ORGANISM: Artificial Sequence
<220> FEATURE:
<223> OTHER INFORMATION: Synthetic polypeptide: ADX_Y1267.ZZ0-1-Vh

<400> SEQUENCE: 72

Gln Val Gln Leu Gln Gln Pro Gly Ala Glu Leu Val Lys Pro Gly Ala
1               5                   10                  15

Ser Val Arg Leu Ser Cys Glu Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Gln Ile Asn Pro Ser Asn Gly Arg Thr Gln Tyr Asn Glu Lys Phe
    50                  55                  60

Lys Ser Met Ala Thr Leu Thr Val Asp Lys Ser Ser Thr Ala Tyr
65                  70                  75                  80

Ile Gln Leu Asn Ser Leu Thr Ser Glu Asp Ser Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ala
        115

<210> SEQ ID NO 73
<211> LENGTH: 117
<212> TYPE: PRT
<213> ORGANISM: Artificial Sequence
<220> FEATURE:
<223> OTHER INFORMATION: Synthetic polypeptide: ADX_Y1268.ZZ0-1-Vh

<400> SEQUENCE: 73

Gln Val Gln Leu Gln Gln Pro Gly Ala Glu Leu Val Lys Pro Gly Ala
1               5                   10                  15

Ser Val Arg Leu Ser Cys Lys Ala Ser Gly Tyr Ala Phe Thr Ser Tyr
            20                  25                  30

Trp Met His Trp Val Lys Gln Arg Pro Gly Gln Gly Leu Glu Trp Ile
        35                  40                  45

Gly Gln Ile Asn Pro Ser Asn Gly Arg Ser Gln Tyr Asn Glu Lys Phe
    50                  55                  60

Lys Thr Met Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ala
        115

<210> SEQ ID NO 74
<211> LENGTH: 118
<212> TYPE: PRT
<213> ORGANISM: Artificial Sequence
<220> FEATURE:
<223> OTHER INFORMATION: Synthetic polypeptide: ADX_Y1269.ZZ0-1-Vh

<400> SEQUENCE: 74

Gln Val Gln Leu Gln Gln Ser Gly Ala Glu Leu Pro Arg Pro Gly Ala
1               5                   10                  15

Ser Val Lys Met Ser Cys Lys Ala Ser Gly Tyr Thr Phe Thr Asp Tyr
            20                  25                  30

Thr Val His Trp Val Lys Gln Arg Pro Gly Gln Gly Leu Glu Trp Ile
        35                  40                  45

Gly Tyr Ile Asn Pro Ser Ser Ser Tyr Thr Ser Tyr Asp Gln Lys Phe
    50                  55                  60

Lys Asp Lys Ala Thr Val Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Thr Met Tyr Trp Tyr Phe Asp Ile Trp Gly Ala Gly Thr
            100                 105                 110

Thr Val Thr Val Ser Ser
        115

<210> SEQ ID NO 75
<211> LENGTH: 120
<212> TYPE: PRT
<213> ORGANISM: Artificial Sequence
<220> FEATURE:
<223> OTHER INFORMATION: Synthetic polypeptide: ADX_Y1297.ZZ0-1-Vh

<400> SEQUENCE: 75

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Thr Tyr Tyr Tyr Gly Ser Arg Phe Pro Tyr Trp Gly Gln
            100                 105                 110

Gly Thr Leu Val Thr Val Ser Ala
        115                 120

```
<210> SEQ ID NO 76
<211> LENGTH: 107
<212> TYPE: PRT
<213> ORGANISM: Artificial Sequence
<220> FEATURE:
<223> OTHER INFORMATION: Synthetic polypeptide: ADX_Y1060.ZZ0-1-Vk

<400> SEQUENCE: 76

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys
            100                 105

<210> SEQ ID NO 77
<211> LENGTH: 112
<212> TYPE: PRT
<213> ORGANISM: Artificial Sequence
<220> FEATURE:
<223> OTHER INFORMATION: Synthetic polypeptide: ADX_Y1072.ZZ0-1-Vk

<400> SEQUENCE: 77

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Phe Pro Tyr Thr Phe Gly Gly Gly Thr Lys Leu Glu Ile Lys
            100                 105                 110

<210> SEQ ID NO 78
<211> LENGTH: 107
<212> TYPE: PRT
<213> ORGANISM: Artificial Sequence
<220> FEATURE:
<223> OTHER INFORMATION: Synthetic polypeptide: ADX_Y1234.ZZ0-1-Vk

<400> SEQUENCE: 78

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Ile Gly Ser Pro Arg Leu Leu Ile
        35                  40                  45
```

Lys Tyr Ala Ser Glu Ser Ile Ser Gly Ile Pro Ser Arg Phe Ser Gly
            50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ile Asn Ser Trp Pro Leu
                85                  90                  95

Thr Phe Gly Ala Gly Thr Lys Leu Glu Leu Lys
            100                 105

<210> SEQ ID NO 79
<211> LENGTH: 107
<212> TYPE: PRT
<213> ORGANISM: Artificial Sequence
<220> FEATURE:
<223> OTHER INFORMATION: Synthetic polypeptide: ADX_Y1236.ZZ0-1-Vk

<400> SEQUENCE: 79

Asp Ile Val Met Thr Gln Ser Gln Lys Phe Met Ser Thr Ser Val Gly
1               5                   10                  15

Asp Arg Ile Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Ala Arg Phe Ser Gly
    50                  55                  60

Ser Gly Ser Gly Thr Ser Tyr Ser Leu Thr Ile Ser Arg Met Glu Ala
65                  70                  75                  80

Glu Asp Ala Ala Thr Tyr Tyr Cys Gln Gln Arg Ser Ser Tyr Pro Leu
                85                  90                  95

Thr Phe Gly Ala Gly Thr Lys Leu Glu Leu Lys
            100                 105

<210> SEQ ID NO 80
<211> LENGTH: 107
<212> TYPE: PRT
<213> ORGANISM: Artificial Sequence
<220> FEATURE:
<223> OTHER INFORMATION: Synthetic polypeptide: ADX_Y1238.ZZ0-1-Vk

<400> SEQUENCE: 80

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Thr Gly
            20                  25                  30

Val Ala Trp Tyr Gln Gln Lys Pro Gly Gln Ser Pro Lys Leu Leu Ile
        35                  40                  45

Tyr Ser Ala Ser Tyr Arg Asn Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys
            100                 105

<210> SEQ ID NO 81
<211> LENGTH: 107
<212> TYPE: PRT

<213> ORGANISM: Artificial Sequence
<220> FEATURE:
<223> OTHER INFORMATION: Synthetic polypeptide: ADX_Y1241.ZZ0-1-Vk

<400> SEQUENCE: 81

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 82
<211> LENGTH: 107
<212> TYPE: PRT
<213> ORGANISM: Artificial Sequence
<220> FEATURE:
<223> OTHER INFORMATION: Synthetic polypeptide: ADX_Y1242.ZZ0-1-Vk

<400> SEQUENCE: 82

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 83
<211> LENGTH: 107
<212> TYPE: PRT
<213> ORGANISM: Artificial Sequence
<220> FEATURE:
<223> OTHER INFORMATION: Synthetic polypeptide: ADX_Y1249.ZZ0-1-Vk

<400> SEQUENCE: 83

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 84
<211> LENGTH: 107
<212> TYPE: PRT
<213> ORGANISM: Artificial Sequence
<220> FEATURE:
<223> OTHER INFORMATION: Synthetic polypeptide: ADX_Y1256.ZZ0-1-Vk

<400> SEQUENCE: 84

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: Synthetic polypeptide: ADX_Y1257.ZZ0-1-Vk

<400> SEQUENCE: 85

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: Synthetic polypeptide: ADX_Y1258.ZZ0-1-Vk

<400> SEQUENCE: 86

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 87
<211> LENGTH: 107
<212> TYPE: PRT
<213> ORGANISM: Artificial Sequence
<220> FEATURE:
<223> OTHER INFORMATION: Synthetic polypeptide: ADX_Y1259.ZZ0-1-Vk

<400> SEQUENCE: 87

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: Synthetic polypeptide: ADX_Y1260.ZZ0-1-Vk

<400> SEQUENCE: 88

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Synthetic polypeptide: ADX_Y1261.ZZ0-1-Vk

<400> SEQUENCE: 89

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Synthetic polypeptide: ADX_Y1262.ZZ0-1-Vk

<400> SEQUENCE: 90

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Tyr Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: Synthetic polypeptide: ADX_Y1263.ZZ0-1-Vk

<400> SEQUENCE: 91

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65              70                  75                  80

Glu Asp Leu Ala Val Tyr Tyr Cys Gln Gln His Tyr Ser Thr Pro Trp
            85                  90                  95

Thr Phe Gly Gly Gly Thr Lys Leu Glu Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: Synthetic polypeptide: ADX_Y1264.ZZ0-1-Vk

<400> SEQUENCE: 92

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65              70                  75                  80

Glu Asp Leu Ala Val Tyr Tyr Cys His Gln His Tyr Ser Thr Pro Trp
            85                  90                  95

Thr Phe Gly Gly Gly Thr Lys Leu Glu Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: Synthetic polypeptide: ADX_Y1265.ZZ0-1-Vk

<400> SEQUENCE: 93

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65              70                  75                  80

Glu Asp Leu Ala Val Tyr Tyr Cys Gln Gln His Tyr Ser Thr Pro Trp
            85                  90                  95

```
Thr Phe Gly Gly Gly Thr Lys Leu Glu Ile Lys
            100                 105
```

<210> SEQ ID NO 94
<211> LENGTH: 107
<212> TYPE: PRT
<213> ORGANISM: Artificial Sequence
<220> FEATURE:
<223> OTHER INFORMATION: Synthetic polypeptide: ADX_Y1266.ZZ0-1-Vk

<400> SEQUENCE: 94

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105
```

<210> SEQ ID NO 95
<211> LENGTH: 107
<212> TYPE: PRT
<213> ORGANISM: Artificial Sequence
<220> FEATURE:
<223> OTHER INFORMATION: Synthetic polypeptide: ADX_Y1267.ZZ0-1-Vk

<400> SEQUENCE: 95

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Leu Gln His Tyr Thr Thr Pro Trp
                85                  90                  95

Thr Phe Gly Gly Gly Thr Lys Leu Glu Ile Lys
            100                 105
```

<210> SEQ ID NO 96
<211> LENGTH: 107
<212> TYPE: PRT
<213> ORGANISM: Artificial Sequence
<220> FEATURE:
<223> OTHER INFORMATION: Synthetic polypeptide: ADX_Y1268.ZZ0-1-Vk

<400> SEQUENCE: 96

```
Asp Ile Val Met Thr Gln Ser His Lys Phe Met Ser Thr Ser Val Gly
1               5                   10                  15
```

```
Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105
```

<210> SEQ ID NO 97
<211> LENGTH: 107
<212> TYPE: PRT
<213> ORGANISM: Artificial Sequence
<220> FEATURE:
<223> OTHER INFORMATION: Synthetic polypeptide: ADX_Y1269.ZZ0-1-Vk

<400> SEQUENCE: 97

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Pro Asn
            20                  25                  30

Val Ala Trp Tyr Gln Gln Lys Pro Gly Gln Ser Pro Lys Leu Leu Ile
        35                  40                  45

Tyr Ser Thr Ser Tyr Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Ile Tyr Tyr Cys Gln Gln His Tyr Ser Thr Pro Leu
                85                  90                  95

Thr Phe Gly Ala Gly Thr Lys Leu Glu Leu Lys
            100                 105
```

<210> SEQ ID NO 98
<211> LENGTH: 107
<212> TYPE: PRT
<213> ORGANISM: Artificial Sequence
<220> FEATURE:
<223> OTHER INFORMATION: Synthetic polypeptide: ADX_Y1297.ZZ0-1-Vk

<400> SEQUENCE: 98

```
Asp Ile Val Met Thr Gln Ser His Lys Phe Met Ser Thr Ser Val Gly
1               5                   10                  15

Asp Arg Val Ser Val Thr Cys Lys Ala Ser Gln Asn Val Arg Ile Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Leu Thr Ile Thr Asn Val Gln Ser
65                  70                  75                  80

Glu Asp Leu Ala Glu Tyr Phe Cys Gln Gln Tyr Asn Thr Tyr Pro Leu
                85                  90                  95

Thr Phe Gly Ala Gly Thr Lys Leu Glu Leu Lys
            100                 105
```

<210> SEQ ID NO 99
<211> LENGTH: 117
<212> TYPE: PRT
<213> ORGANISM: Artificial Sequence
<220> FEATURE:
<223> OTHER INFORMATION: Synthetic polypeptide: Vh-C1

<400> SEQUENCE: 99

```
Gln Val Gln Leu Gln Gln Ser Gly Ala Glu Leu Ala Lys Pro Gly Ser
1               5                   10                  15

Ser Val Lys Met Ser Cys Lys Ala Ser Gly Tyr Ala Phe Thr Ser Tyr
            20                  25                  30

Trp Met His Trp Ile Lys Gln Arg Pro Gly Gln Gly Leu Glu Trp Ile
        35                  40                  45

Gly Phe Ile Asn Pro Thr Thr Gly Tyr Ser Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Trp Gly Leu Pro Pro Phe Ala Tyr Trp Gly Gln Gly Thr Leu
            100                 105                 110

Val Thr Val Ser Ala
            115
```

<210> SEQ ID NO 100
<211> LENGTH: 117
<212> TYPE: PRT
<213> ORGANISM: Artificial Sequence
<220> FEATURE:
<223> OTHER INFORMATION: Synthetic polypeptide: Vh-hz1

<400> SEQUENCE: 100

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Phe Ile Asn Pro Thr Thr Gly Tyr Ser Glu Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Pro Pro Phe Ala Tyr Trp Gly Gln Gly Thr Leu
            100                 105                 110

Val Thr Val Ser Ser
            115
```

<210> SEQ ID NO 101
<211> LENGTH: 117
<212> TYPE: PRT
<213> ORGANISM: Artificial Sequence
<220> FEATURE:
<223> OTHER INFORMATION: Synthetic polypeptide: Vh-hz2

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Arg Pro Gly Gln Gly Leu Glu Trp Met
        35                  40                  45

Gly Phe Ile Asn Pro Thr Thr Gly Tyr Ser Glu Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Pro Pro Phe Ala Tyr Trp Gly Gln Gly Thr Leu
            100                 105                 110

Val Thr Val Ser Ser
            115

<210> SEQ ID NO 102
<211> LENGTH: 117
<212> TYPE: PRT
<213> ORGANISM: Artificial Sequence
<220> FEATURE:
<223> OTHER INFORMATION: Synthetic polypeptide: Vh-hz3

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Arg Pro Gly Gln Gly Leu Glu Trp Ile
        35                  40                  45

Gly Phe Ile Asn Pro Thr Thr Gly Tyr Ser Glu Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Arg Trp Gly Leu Pro Pro Phe Ala Tyr Trp Gly Gln Gly Thr Leu
            100                 105                 110

Val Thr Val Ser Ser
            115

<210> SEQ ID NO 103
<211> LENGTH: 117
<212> TYPE: PRT
<213> ORGANISM: Artificial Sequence
<220> FEATURE:
<223> OTHER INFORMATION: Synthetic polypeptide: Vh-C2

<400> SEQUENCE: 103

Gln Val Gln Leu Gln Gln Ser Gly Ala Glu Leu Ala Lys Pro Gly Ser
1               5                   10                  15

Ser Val Lys Met Ser Cys Lys Ala Ser Gly Tyr Ala Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Thr Thr Gly Tyr Ser Ala Tyr Asn Gln Lys Phe
    50                  55                  60

```
Lys Asp Lys Ala Thr Leu Thr Ala Asp Lys Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Trp Asp Pro Arg Pro Phe Ala Tyr Trp Gly Gln Gly Thr Leu
            100                 105                 110

Val Thr Val Ser Ala
        115

<210> SEQ ID NO 104
<211> LENGTH: 117
<212> TYPE: PRT
<213> ORGANISM: Artificial Sequence
<220> FEATURE:
<223> OTHER INFORMATION: Synthetic polypeptide: Vh-hz4

<400> SEQUENCE: 104

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
                20                  25                  30

Trp Met His Trp Val Arg Gln Ala Pro Gly Gln Gly Leu Glu Trp Met
            35                  40                  45

Gly Tyr Ile Asn Pro Thr Thr Gly Tyr Ser Ala Tyr Asn Gln Lys Phe
    50                  55                  60

Lys Asp Lys Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Asp Pro Arg Pro Phe Ala Tyr Trp Gly Gln Gly Thr Leu
            100                 105                 110

Val Thr Val Ser Ser
        115

<210> SEQ ID NO 105
<211> LENGTH: 117
<212> TYPE: PRT
<213> ORGANISM: Artificial Sequence
<220> FEATURE:
<223> OTHER INFORMATION: Synthetic polypeptide: Vh-hz5

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
                20                  25                  30

Trp Met His Trp Val Arg Gln Arg Pro Gly Gln Gly Leu Glu Trp Met
            35                  40                  45

Gly Tyr Ile Asn Pro Thr Thr Gly Tyr Ser Ala Tyr Asn Gln Lys Phe
    50                  55                  60

Lys Asp Lys Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Asp Pro Arg Pro Phe Ala Tyr Trp Gly Gln Gly Thr Leu
            100                 105                 110

Val Thr Val Ser Ser
```

<210> SEQ ID NO 106
<211> LENGTH: 117
<212> TYPE: PRT
<213> ORGANISM: Artificial Sequence
<220> FEATURE:
<223> OTHER INFORMATION: Synthetic polypeptide: Vh-hz6

<400> SEQUENCE: 106

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ala Phe Thr Ser Tyr
                20                  25                  30
Trp Met His Trp Val Arg Gln Arg Pro Gly Gln Gly Leu Glu Trp Ile
            35                  40                  45
Gly Tyr Ile Asn Pro Thr Thr Gly Tyr Ser Ala Tyr Asn Gln Lys Phe
    50                  55                  60
Lys Asp Lys Ala Thr Leu Thr Ala Asp Lys Ser Thr Ser Thr Ala Tyr
65                  70                  75                  80
Met Glu Leu Asn Ser Leu Arg Ser Glu Asp Thr Ala Val Tyr Tyr Cys
                85                  90                  95
Ala Arg Trp Asp Pro Arg Pro Phe Ala Tyr Trp Gly Gln Gly Thr Leu
            100                 105                 110
Val Thr Val Ser Ser
        115
```

<210> SEQ ID NO 107
<211> LENGTH: 117
<212> TYPE: PRT
<213> ORGANISM: Artificial Sequence
<220> FEATURE:
<223> OTHER INFORMATION: Synthetic polypeptide: Vh-hz7

<400> SEQUENCE: 107

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ala Phe Thr Ser Tyr
                20                  25                  30
Trp Met His Trp Val Arg Gln Ala Pro Gly Gln Gly Leu Glu Trp Met
            35                  40                  45
Gly Tyr Ile Asn Pro Thr Thr Gly Tyr Ser Ala Tyr Asn Gln Lys Phe
    50                  55                  60
Lys Asp Lys Ala Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Trp Gln Pro Arg Pro Phe Ala Tyr Trp Gly Gln Gly Thr Leu
            100                 105                 110
Val Thr Val Ser Ser
        115
```

<210> SEQ ID NO 108
<211> LENGTH: 117
<212> TYPE: PRT
<213> ORGANISM: Artificial Sequence
<220> FEATURE:
<223> OTHER INFORMATION: Synthetic polypeptide: Vh-hz8

<400> SEQUENCE: 108

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
                20                  25                  30

Trp Met His Trp Val Arg Gln Ala Pro Gly Gln Gly Leu Glu Trp Met
            35                  40                  45

Gly Tyr Ile Asn Pro Thr Thr Gly Tyr Ser Ala Tyr Asn Gln Lys Phe
        50                  55                  60

Lys Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Ala Arg Pro Phe Ala Tyr Trp Gly Gln Gly Thr Leu
            100                 105                 110

Val Thr Val Ser Ser
        115

<210> SEQ ID NO 109
<211> LENGTH: 117
<212> TYPE: PRT
<213> ORGANISM: Artificial Sequence
<220> FEATURE:
<223> OTHER INFORMATION: Synthetic polypeptide: Vh-C3

<400> SEQUENCE: 109

Gln Val Gln Leu Gln Gln Pro Gly Ala Glu Leu Val Lys Pro Gly Ala
1               5                   10                  15

Ser Val Arg Leu Ser Cys Lys Ala Ser Gly Tyr Ala Phe Thr Ser Tyr
                20                  25                  30

Trp Met His Trp Val Lys Gln Arg Pro Gly Gln Gly Leu Glu Trp Ile
            35                  40                  45

Gly Gln Ile Asn Pro Ser Asn Gly Arg Ser Gln Tyr Asn Glu Lys Phe
        50                  55                  60

Lys Thr Met Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ala
        115

<210> SEQ ID NO 110
<211> LENGTH: 117
<212> TYPE: PRT
<213> ORGANISM: Artificial Sequence
<220> FEATURE:
<223> OTHER INFORMATION: Synthetic polypeptide: Vh-hz9

<400> SEQUENCE: 110

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
                20                  25                  30

Trp Met His Trp Val Arg Gln Ala Pro Gly Gln Gly Leu Glu Trp Met
            35                  40                  45

Gly Gln Ile Asn Pro Ser Asn Gly Arg Ser Gln Tyr Asn Glu Lys Phe
```

```
                50                  55                  60
Lys Thr Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Leu Gln Pro Phe Ala Tyr Trp Gly Gln Gly Thr Leu
            100                 105                 110

Val Thr Val Ser Ser
            115

<210> SEQ ID NO 111
<211> LENGTH: 117
<212> TYPE: PRT
<213> ORGANISM: Artificial Sequence
<220> FEATURE:
<223> OTHER INFORMATION: Synthetic polypeptide: Vh-hz10

<400> SEQUENCE: 111

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Thr Ser Tyr
                 20                  25                  30

Trp Met His Trp Val Arg Gln Arg Pro Gly Gln Gly Leu Glu Trp Met
             35                  40                  45

Gly Gln Ile Asn Pro Ser Asn Gly Arg Ser Gln Tyr Asn Glu Lys Phe
         50                  55                  60

Lys Thr Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Leu Gln Pro Phe Ala Tyr Trp Gly Gln Gly Thr Leu
            100                 105                 110

Val Thr Val Ser Ser
            115

<210> SEQ ID NO 112
<211> LENGTH: 117
<212> TYPE: PRT
<213> ORGANISM: Artificial Sequence
<220> FEATURE:
<223> OTHER INFORMATION: Synthetic polypeptide: Vh-hz11

<400> SEQUENCE: 112

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Thr Ser Tyr
                 20                  25                  30

Trp Met His Trp Val Arg Gln Arg Pro Gly Gln Gly Leu Glu Trp Ile
             35                  40                  45

Gly Gln Ile Asn Pro Ser Asn Gly Arg Ser Gln Tyr Asn Glu Lys Phe
         50                  55                  60

Lys Thr Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Leu Gln Pro Phe Ala Tyr Trp Gly Gln Gly Thr Leu
            100                 105                 110
```

```
Val Thr Val Ser Ser
        115

<210> SEQ ID NO 113
<211> LENGTH: 117
<212> TYPE: PRT
<213> ORGANISM: Artificial Sequence
<220> FEATURE:
<223> OTHER INFORMATION: Synthetic polypeptide: Vh-hz13

<400> SEQUENCE: 113

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Ser Asn Ala Arg Ser Gly Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser
        115

<210> SEQ ID NO 114
<211> LENGTH: 107
<212> TYPE: PRT
<213> ORGANISM: Artificial Sequence
<220> FEATURE:
<223> OTHER INFORMATION: Synthetic polypeptide: Vk-C1

<400> SEQUENCE: 114

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 115
<211> LENGTH: 107
<212> TYPE: PRT
<213> ORGANISM: Artificial Sequence
<220> FEATURE:
<223> OTHER INFORMATION: Synthetic polypeptide: Vk-C2

<400> SEQUENCE: 115

Asp Ile Val Met Thr Gln Ser His Lys Phe Met Ser Thr Ser Val Gly
```

-continued

```
1               5                   10                  15
Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
    50                  55                  60

Ser Gly Tyr Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
                100                 105
```

<210> SEQ ID NO 116
<211> LENGTH: 107
<212> TYPE: PRT
<213> ORGANISM: Artificial Sequence
<220> FEATURE:
<223> OTHER INFORMATION: Synthetic polypeptide: Vk-hz1

<400> SEQUENCE: 116

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Trp
                85                  90                  95

Thr Phe Gly Gly Gly Thr Lys Val Glu Ile Lys
                100                 105
```

<210> SEQ ID NO 117
<211> LENGTH: 330
<212> TYPE: PRT
<213> ORGANISM: Homo sapiens

<400> SEQUENCE: 117

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 118
<211> LENGTH: 232
<212> TYPE: PRT
<213> ORGANISM: Artificial Sequence
<220> FEATURE:
<223> OTHER INFORMATION: Synthetic polypeptide: Fc consensus
<220> FEATURE:
<221> NAME/KEY: MOD_RES
<222> LOCATION: (23)..(23)
<223> OTHER INFORMATION: Leu, Ser, Ala, Arg, or Trp
<220> FEATURE:
<221> NAME/KEY: MOD_RES
<222> LOCATION: (141)..(141)
<223> OTHER INFORMATION: Asp or Glu
<220> FEATURE:
<221> NAME/KEY: MOD_RES
<222> LOCATION: (143)..(143)
<223> OTHER INFORMATION: Leu or Met
<220> FEATURE:
<221> NAME/KEY: MOD_RES
<222> LOCATION: (232)..(232)
<223> OTHER INFORMATION: Lys or absent

<400> SEQUENCE: 118

Glu Pro Lys Ser Cys Asp Lys Thr His Thr Cys Pro Pro Cys Pro Ala
1               5                   10                  15

Pro Glu Leu Leu Gly Gly Xaa Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
```

-continued

```
            50                  55                  60
Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Xaa Glu Xaa Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Xaa
225                 230

<210> SEQ ID NO 119
<211> LENGTH: 232
<212> TYPE: PRT
<213> ORGANISM: Artificial Sequence
<220> FEATURE:
<223> OTHER INFORMATION: Synthetic polypeptide: Fc consensus
<220> FEATURE:
<221> NAME/KEY: MOD_RES
<222> LOCATION: (141)..(141)
<223> OTHER INFORMATION: Asp or Glu
<220> FEATURE:
<221> NAME/KEY: MOD_RES
<222> LOCATION: (143)..(143)
<223> OTHER INFORMATION: Leu or Met
<220> FEATURE:
<221> NAME/KEY: MOD_RES
<222> LOCATION: (232)..(232)
<223> OTHER INFORMATION: Lys or absent

<400> SEQUENCE: 119

Glu Pro Lys Ser Cys Asp Lys Thr His Thr Cys Pro Pro Cys Pro Ala
  1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
         50                  55                  60

Asp Gly Val Glu Val His Asn Ala Lys Thr Lys Pro Arg Glu Glu Gln
 65                  70                  75                  80

Tyr Ala Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
```

```
                115                 120                 125
Arg Glu Pro Gln Val Tyr Thr Leu Pro Pro Ser Arg Xaa Glu Xaa Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
            210                 215                 220

Ser Leu Ser Leu Ser Pro Gly Xaa
225                 230

<210> SEQ ID NO 120
<211> LENGTH: 232
<212> TYPE: PRT
<213> ORGANISM: Artificial Sequence
<220> FEATURE:
<223> OTHER INFORMATION: Synthetic polypeptide: Fc consensus
<220> FEATURE:
<221> NAME/KEY: MOD_RES
<222> LOCATION: (23)..(23)
<223> OTHER INFORMATION: Leu, Ser, Ala, Arg, or Trp
<220> FEATURE:
<221> NAME/KEY: MOD_RES
<222> LOCATION: (82)..(82)
<223> OTHER INFORMATION: Asn or Ala
<220> FEATURE:
<221> NAME/KEY: MOD_RES
<222> LOCATION: (141)..(141)
<223> OTHER INFORMATION: Asp or Glu
<220> FEATURE:
<221> NAME/KEY: MOD_RES
<222> LOCATION: (143)..(143)
<223> OTHER INFORMATION: Leu or Met
<220> FEATURE:
<221> NAME/KEY: MOD_RES
<222> LOCATION: (232)..(232)
<223> OTHER INFORMATION: Lys or absent

<400> SEQUENCE: 120

Glu Pro Lys Ser Cys Asp Lys Thr His Thr Cys Pro Pro Cys Pro Ala
1               5                   10                  15

Pro Glu Leu Leu Gly Gly Xaa Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Xaa Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Xaa Glu Xaa Thr
    130                 135                 140
```

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Xaa
225                 230
```

ANTAGONISTIC CD40 MONOCLONAL ANTIBODIES AND USES THEREOF

CROSS REFERENCE TO RELATED APPLICATIONS

This application is a divisional of U.S. patent application Ser. No. 17/080,626, filed Oct. 26, 2020, now U.S. Pat. No. 11,254,750, which is a continuation of U.S. patent application Ser. No. 16/686,596, filed Nov. 18, 2019, now U.S. Pat. No. 11,261,258, which claims the benefit of U.S. Provisional Application No. 62/769,514, filed Nov. 19, 2018, each of which is hereby incorporated in its entirety for all purposes.

SEQUENCE LISTING

The instant application contains a Sequence Listing which has been submitted electronically in ASCII format and is hereby incorporated by reference in its entirety. Said ASCII copy, created on Feb. 10, 2022, is named 200896-0015-04-US-000033-SL.txt and is 167,751 bytes in size.

FIELD

The disclosure provides antibodies that bind CD40. The antibody polypeptides bind CD40 and do not exhibit CD40 agonist activity. The antibodies may comprise a modified IgG1 Fc domain, and exhibit minimal activation of immature dendritic cells. Compositions comprising antibodies, methods of use for treatment of diseases involving CD40 activity, and use in the preparation of a medicament for treatment of a disease involving CD40 activity are provided.

BACKGROUND

CD40 is a co-stimulatory molecule belonging to the tumor necrosis factor (TNF) receptor superfamily that is present on antigen presenting cells (APC), including dendritic cells, B cells, and macrophages. APCs are activated when CD40 binds its ligand, CD154 (CD40L), on $T_H$ cells. CD40-mediated APC activation is involved in a variety of immune responses, including cytokine production, up-regulation of co-stimulatory molecules (such as CD86), and enhanced antigen presentation and B cell proliferation. CD40 can also be expressed by endothelial cells, smooth muscle cells, fibroblasts, and epithelial cells.

CD40 activation is also involved in a variety of undesired T cell responses related to autoimmunity, transplant rejection, or allergic responses, for example. One strategy for controlling undesirable T cell responses is to target CD40 with an antagonistic antibody. For example, monoclonal antibody HCD122 (Lucatumumab), formerly known as Chiron 1212, is currently in clinical trials for the treatment of certain CD40-mediated inflammatory diseases. See "Study of HCD122 (Lucatumumab) and Bendamustine Combination Therapy in CD40+ Rituximab-Refractory Follicular Lymphoma," Clinical Trials Feeds, on the Internet at hypertext transfer protocol: clinicaltrialsfeeds.org/clinical-trials/show/NCT01275209 (last updated Jan. 11, 2011). Monoclonal antibodies, however, can display agonist activity. For example, the usefulness of the anti-CD40 antibody, Chi220, is limited by its weak stimulatory potential. See Adams, et al., "Development of a chimeric anti-CD40 monoclonal antibody that synergizes with LEA29Y to prolong islet allograft survival," *J. Immunol.* 174: 542-50 (2005).

SUMMARY

In a first embodiment, the present invention provides an isolated antibody, or antigen binding portion thereof, that specifically binds to human CD40, wherein the antibody comprises a first polypeptide portion comprising a heavy chain variable region, and a second polypeptide portion comprising a light chain variable region, wherein:

the heavy chain variable region comprises one of (i) a CDR1 comprising SYWMH (SEQ ID NO: 1), a CDR2 comprising QINPTTGRSQYNEKFKT (SEQ ID NO: 2), a CDR3 comprising WGLQPFAY (SEQ ID NO: 3); and (ii) a CDR1 comprising SYWMH (SEQ ID NO: 1), a CDR2 comprising QINPSQGRSQYNEKFKT (SEQ ID NO: 12), a CDR3 comprising WGLQPFAY (SEQ ID NO: 3); and the light chain variable region comprises a CDR1 comprising KASQDVSTAVA (SEQ ID NO: 7), a CDR2 comprising SASYRYT (SEQ ID NO: 8), and a CDR3 comprising QQHYSTPWT (SEQ ID NO: 9).

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein:

the heavy chain variable region comprises one of (i) a CDR1 consisting of SYWMH (SEQ ID NO: 1), a CDR2 consisting of QINPTTGRSQYNEKFKT (SEQ ID NO: 2), a CDR3 consisting of WGLQPFAY (SEQ ID NO: 3); and (ii) a CDR1 consisting of SYWMH (SEQ ID NO: 1), a CDR2 consisting of QINPSQGRSQYNEKFKT (SEQ ID NO: 12), a CDR3 consisting of WGLQPFAY (SEQ ID NO: 3); and the light chain variable region comprises a CDR1 consisting of KASQDVSTAVA (SEQ ID NO: 7), a CDR2 consisting of SASYRYT (SEQ ID NO: 8), and a CDR3 consisting of QQHYSTPWT (SEQ ID NO: 9).

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein:

the heavy chain variable region comprises a CDR1 consisting of SYWMH (SEQ ID NO: 1), a CDR2 consisting QINPTTGRSQYNEKFKT (SEQ ID NO: 2), a CDR3 consisting of WGLQPFAY (SEQ ID NO: 3); and the light chain variable region comprises a CDR1 consisting of KASQDVSTAVA (SEQ ID NO: 7), a CDR2 consisting of SASYRYT (SEQ ID NO: 8), and a CDR3 consisting of QQHYSTPWT (SEQ ID NO: 9).

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein:

the heavy chain variable region comprises the amino acid sequence of (SEQ ID NO: 4)
QVQLVQSGAEVKKPGSSVKVSCKASGYAFTSYWMHWVRQAPGQGLEWMG

QINPTTGRSQYNEKFKTRVTITADKSTSTAYMELSSLRSEDTAVYYCAR

WGLQPFAYWGQGTLVTVSS, and the light chain variable region comprises the amino acid sequence of (SEQ ID NO: 10)
DIQMTQSPSFLSASVGDRVTITCKASQDVSTAVAWYQQKPGKAPKWYSA

SYRYTGVPSRFSGSGSGTDFTLTISSLQPEDFATYYCQQHYSTPWTFGG

GTKVEIK.

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein the heavy chain variable region comprises the amino acid sequence of (SEQ ID NO: 13)
QVQLVQSGAEVKKPGSSVKVSCKASGYAFTSYWMHWVRQAPGQGLEWMG

QINPSQGRSQYNEKFKTRVTITADKSTSTAYMELSSLRSEDTAVYYCAR

WGLQPFAYWGQGTLVTVSS, and the light chain variable region comprises the amino acid sequence of (SEQ ID NO: 16)
EIVMTQSPATLSVSPGERATLSCKASQDVSTAVAWYQQKPGQAPRLLIY

SASYRYTGIPARFSGSGSGTEFTLTISSLQSEDFAVYYCQQHYSTPWTF

GGGTKVEIK.

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein the heavy chain variable region comprises the amino acid sequence of (SEQ ID NO: 4)
QVQLVQSGAEVKKPGSSVKVSCKASGYAFTSYWMHWVRQAPGQGLEWMGQ

INPTTGRSOYNEKFKTRVTITADKSTSTAYMELSSLRSEDTAVYYCARWG

LQPFAYWGQGTLVTVSS, and the light chain variable region comprises the amino acid sequence of (SEQ ID NO: 16)
EIVMTQSPATLSVSPGERATLSCKASQDVSTAVAWYQQKPGQAPRLLIYS

ASYRYTGIPARFSGSGSGTEFTLTISSLQSEDFAVYYCQQHYSTPWTFGG

GTKVEIK.

In certain embodiments, the isolated antibody or antigen binding portion thereof comprises the first polypeptide portion comprising a human heavy chain constant region; and the second polypeptide portion comprising a human light chain constant region. The isolated antibody or antigen binding portion thereof described herein can comprise a human IgG1 Fc domain comprising either (1) a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan, and wherein the antibody or antigen binding portion thereof has reduced FcγR binding; or (2) an alanine substituted at Kabat position 297.

The isolated antibody or antigen binding portion thereof described herein can comprise a human IgG1 Fc domain comprising a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan, and wherein the antibody or antigen binding portion has reduced FcγR binding. In certain embodiments, P238 is mutated to lysine.

The isolated antibody or antigen binding portion thereof described herein can comprise an Fc domain which comprises an amino acid sequence selected from:

(SEQ ID NO: 22; IgG1-P238K (-C-term Lys))
EPKSCDKTHTCPPCPAPELLGGKSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPG, (SEQ ID NO: 23; IgG1-P238K)
EPKSCDKTHTCPPCPAPELLGGKSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK, (SEQ ID NO: 24; CH1-IgG1-P238K (-C-term Lys))
*ASTKGPSVFPLAPSSKSTSGGTAALGCLVKDYFPEPVTVSWNSGALTSGV*

*HTFPAVLQSSGLYSLSSVVTVPSSSLGTQTYICNVNHKPSNTKVDKRVEP*

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG, (SEQ ID NO: 25; CH1-IgG1-P238K)
*ASTKGPSVFPLAPSSKSTSGGTAALGCLVKDYFPEPVTVSWNSGALTSGV*

*HTFPAVLQSSGLYSLSSVVTVPSSSLGTQTYICNVNHKPSNTKVDKRVEP*

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK, (SEQ ID NO: 26; IgG1f-P238K (-C-term Lys))
EPKSCDKTHTCPPCPAPELLGGKSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

-continued

TCLVKGFYPSDIAVEWESNGQPENNYKTTPPVLDSDGSFFLYSKLTVDKS

RWQQGNVFSCSVMHEALHNHYTQKSLSLSPG, (SEQ ID NO: 27; IgG1f-P238K)
EPKSCDKTHTCPPCPAPELLGGKSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK, (SEQ ID NO: 28; CH1-IgG1f-P238K (-C-term Lys))
*ASTKGPSVFPLAPSSKSTSGGTAALGCLVKDYFPEPVTVSWNSGALTSGV*

*HTFPAVLQSSGLYSLSSVVTVPSSSLGTQTYICNVNHKPSNTKVDKRV*EP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPG,
or (SEQ ID No: 29; CH1-IgG1f-P238K)
*ASTKGPSVFPLAPSSKSTSGGTAALGCLVKDYFPEPVTVSWNSGALTSGV*

*HTFPAVLQSSGLYSLSSVVTVPSSSLGTQTYICNVNHKPSNTKVDKRV*EP

KSCDKTHTCPPCPAPELLGGKSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In certain embodiments, the isolated antibody or antigen binding portion thereof described herein comprises a human IgG1 Fc domain comprising either (1) a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan, and wherein the antibody or antigen binding portion thereof has reduced FcγR binding; or (2) an alanine substituted at Kabat position 297, comprises a heavy chain variable region comprising a CDR1 comprising SYWMH (SEQ ID NO: 1), a CDR2 comprising QINPTTGRSQYNEKFKT (SEQ ID NO: 2), a CDR3 comprising WGLQPFAY (SEQ ID NO: 3); and a light chain variable region comprising a CDR1 comprising KASQDVSTAVA (SEQ ID NO: 7), a CDR2 comprising SASYRYT (SEQ ID NO: 8), and a CDR3 comprising QQHYSTPWT (SEQ ID NO: 9).

The isolated antibody or antigen binding portion thereof can comprise a human IgG1 Fc domain comprising the amino acid sequence of SEQ ID NO: 22 or SEQ ID NO: 23.

In some embodiments of the isolated antibody or antigen binding portion thereof described herein, the first polypeptide portion comprises or consists of an amino acid sequence selected from the group consisting of:

QVQLVQSGAEVKKPGSSVKVSCKASGYAFTSYWMHWVRQAPGQGLEWMGQ

INPTTGRSQYNEKFKTRVTITADKSTSTAYMELSSLRSEDTAVYYCARWG

LQPFAYWGQGTLVTVSS*ASTKGPSVFPLAPSSKSTSGGTAALGCLVKDYF*

*PEPVTVSWNSGALTSGVHTFPAVLQSSGLYSLSSVVTVPSSSLGTQTYIC*

*NVNHKPSNTKVDKRV*EPKSCDKTHTCPPCPAPELLGGKSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG (SEQ ID NO: 5; HC_Y12XX-hz28-CH1-IgG1-P238K- no terminal lysine),

QVQLVQSGAEVKKPGSSVKVSCKASGYAFTSYWMHWVRQAPGQGLEWMGQ

INPTTGRSQYNEKFKTRVTITADKSTSTAYMELSSLRSEDTAVYYCARWG

LQPFAYWGQGTLVTVSS*ASTKGPSVFPLAPSSKSTSGGTAALGCLVKDYF*

*PEPVTVSWNSGALTSGVHTFPAVLQSSGLYSLSSVVTVPSSSLGTQTYIC*

*NVNHKPSNTKVDKRV*EPKSCDKTHTCPPCPAPELLGGKSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (SEQ ID NO: 6; HC_Y12XX-hz28-CH1-IgG1-P238K- with terminal lysine),

QVQLVQSGAEVKKPGSSVKVSCKASGYAFTSYWMHWVRQAPGQGLEWMGQ

INPTTGRSQYNEKFKTRVTITADKSTSTAYMELSSLRSEDTAVYYCARWG

LQPFAYWGQGTLVTVSS*ASTKGPSVFPLAPSSKSTSGGTAALGCLVKDYF*

*PEPVTVSWNSGALTSGVHTFPAVLQSSGLYSLSSVVTVPSSSLGTQTYIC*

*NVNHKPSNTKVDKRV*EPKSCDKTHTCPPCPAPELLGGKSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPG (SEQ ID NO: 30; HC_Y12XX-hz28-CH1-IgG1f-P238K- no terminal lysine),
and

QVQLVQSGAEVKKPGSSVKVSCKASGYAFTSYWMHWVRQAPGQGLEWMGQ

INPTTGRSQYNEKFKTRVTITADKSTSTAYMELSSLRSEDTAVYYCARWG

LQPFAYWGQGTLVTVSS*ASTKGPSVFPLAPSSKSTSGGTAALGCLVKDYF*

*PEPVTVSWNSGALTSGVHTFPAVLQSSGLYSLSSVVTVPSSSLGTQTYIC*

*NVNHKPSNTKVDKRV*EPKSCDKTHTCPPCPAPELLGGKSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

-continued
LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK (SEQ ID NO: 31; HC_Y12XX-hz28-CH1-IgG1f-P238K- with terminal lysine);

and the second polypeptide portion comprises or consists of the amino acid sequence of (SEQ ID NO: 11; LC_Y12XX-hz28-CL)
DIQMTQSPSFLSASVGDRVTITCKASQDVSTAVAWYQQKPGKAPKWYSAS

YRYTGVPSRFSGSGSGTDFTLTISSLQPEDFATYYCQQHYSTPWTFGGGT

KVEIKRTVAAPSVFIFPPSDEQLKSGTASVVCLLNNFYPREAKVQWKVDN

ALQSGNSQESVTEQDSKDSTYSLSSTLTLSKADYEKHKVYACEVIINGLS

SPVTKSFNRGEC.

In some embodiments of the isolated antibody or antigen binding portion thereof described herein, the first polypeptide portion comprises or consists of an amino acid sequence of

QVQLVQSGAEVKKPGSSVKVSCKASGYAFTSYWMHWVRQAPGQGLEWMGQ

INPTTGRSQYNEKFKTRVTITADKSTSTAYMELSSLRSEDTAVYYCARWG

LQPFAYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSCDKTHTCPPCPAPELLGGKSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG (SEQ ID NO: 5; HC_Y12XX-hz28-CH1-IgG1-P238K- no terminal lysine);
and the second polypeptide portion comprises or consists of the amino acid sequence of (SEQ ID NO: 11; LC_Y12XX-hz28-CL)
DIQMTQSPSFLSASVGDRVTITCKASQDVSTAVAWYQQKPGKAPKLLIYS

ASYRYTGVPSRFSGSGSGTDFTLTISSLQPEDFATYYCQQHYSTPWTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVIHQG

LSSPVTKSFNRGEC.

and the second polypeptide portion comprises or consists of the amino acid sequence of (SEQ ID NO: 11; LC_Y12XX-hz28-CL)
DIQMTQSPSFLSASVGDRVTITCKASQDVSTAVAWYQQKPGKAPK

LLIYSASYRYTGVPSRFSGSGSGTDFTLTISSLQPEDFATYYCQQ

HYSTPWTFGGGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC.

In certain embodiments, the isolated antibody or antigen binding portion thereof described herein comprises a human IgG1 Fc domain comprises a human IgG1 Fc domain comprising an alanine substituted at Kabat position 297.

The isolated antibody or antigen binding portion thereof as described herein can antagonize activities of CD40. The isolated antibody or antigen binding portion thereof described herein can be a chimeric antibody. The isolated antibody or antigen binding portion thereof described herein can be a humanized antibody. The isolated antibody or antigen binding portion thereof described herein can comprise a human heavy chain constant region and a human light chain constant region.

The antibody or antigen binding portion thereof disclosed herein, is an antigen binding portion selected from the group consisting of Fv, Fab, F(ab')2, Fab', dsFv, scFv, sc(Fv)2, diabodies, and scFv-Fc. The isolated antibody or antigen binding portion thereof as described herein is an scFv-Fc.

The antibody or antigen binding portion thereof disclosed herein can linked to a therapeutic agent.

The antibody or antigen binding portion thereof disclosed herein can be linked to a second functional moiety having a different binding specificity than said antibody or antigen binding portion thereof.

The antibody or antigen binding portion thereof disclosed herein can further comprise an additional moiety.

A nucleic acid molecule encoding an isolated antibody or antigen binding portion thereof is disclosed herein. An expression vector comprising the nucleic acid molecule is disclosed herein. Also contemplated is a cell transformed with the expression vector. Also disclosed is a method of preparing an anti-human CD40 antibody, or antigen binding portion thereof, comprising:

a) expressing the antibody, or antigen binding portion thereof, in the cell transformed with the expression vector comprising the nucleic acid molecule encoding an isolated antibody or antigen binding portion thereof disclosed herein; and b) isolating the antibody, or antigen binding portion thereof, from the cell.

Also provided is a pharmaceutical composition comprising: a) the antibody, or antigen binding portion thereof disclosed herein; and b) a pharmaceutically acceptable carrier.

A method is provided of treating or preventing an immune response in a subject comprising administering to the subject the antibody, or the antigen binding portion thereof, disclosed herein. Further provided is a method of treating or preventing an autoimmune or inflammatory disease in a subject, comprising administering to the subject the antibody, or the antigen binding portion, disclosed herein. Optionally, the antibody, or the antigen binding portion thereof, is administered with an immunosuppressive/immunomodulatory and/or anti-inflammatory agent. Administration may be simultaneous or sequential. An exemplary agent is a CTLA4 mutant molecule, such as L104EA29Y-Ig (belatacept). In such method of treating or preventing an immune response in the subject, and in such method of treating or preventing an autoimmune or inflammatory disease in a subject, preferably the subject has a disease selected from the group consisting of: Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), lupus nephritis, lupus nephritis, systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

Also contemplated is an antibody, or antigen binding portion thereof as disclosed here, for use as a medicament. Further contemplated is an antibody, or antigen binding portion thereof as disclosed here, or a medicament comprising the same, for use to treat a subject in need thereof. Further contemplated is an antibody, or antigen binding portion thereof as disclosed herein in a therapeutically-effective amount, for use in treating or preventing an immune response, wherein the antibody or antigen binding portion thereof is for administering to a patient in need thereof.

BRIEF DESCRIPTION OF THE FIGURES

FIGS. 1A-1D depict SPR sensorgram data of binding of antibodies to human FcγRs. FIG. 1A depicts data for a control antibody, control IgG1. FIG. 1B depicts data for Y12XX-hx28-IgG1-P238K, control IgG1. FIG. 1C depicts data for a control antibody, Antibody B. FIG. 1D is a table summarizing the KD values for Antibody/FcγRs interactions. The KD values were obtained from either a 1:1 Langmuir fit (hCD64) or 1:1 steady state fit (hCD32a-H131, hCD32a-R131, hCD32b, hCD16a-V158, and hCD16a-F158).

FIG. 2A depicts IL-6 data. FIG. 2B depicts CD86 data. FIG. 2C depicts CD54 data. The mean fluorescence intensity (MFI) is measured on the Y-axis in both FIG. 2B and FIG. 2C. Each symbol represents data for iDC from an individual donor. Y12XX-hz42-P238K was tested in cells from 4 donors, Y12XX-hz40-P238K was tested in cells from 6 donors, and Y12XX-hz28-P238K was tested in 10 donors. Concentration of antibody in is indicated (10, 30, or 100 µg/ml). Inclusion of CHO-CD32 cells in the assay is as indicated to mediate FcγR mediated cross-linking or clustering. Ly6-IgG was used as a negative control. Partial CD40 agonist 2141 and BMS986090-100 were used as positive controls.

FIG. 3A depicts the data from the first iteration of the assay, and FIG. 3B depicts the data from the second iteration of the assay.

FIG. 4A depicts data obtained with donor #8 CD14+ monocytes as effector cells. FIG. 4B depicts data obtained with donor #65 CD14+ monocytes as effector cells.

FIG. 5A depicts data obtained with donor #38 NK cells as effector cells. FIG. 5B depicts data obtained with donor #55 NK cells as effector cells.

FIGS. 6C and 6D depict data for the positive control, CD40L-IZ. AIMV: AIM V™ medium (1×) (Thermo Fisher Scientific, Waltham, Mass.).

DETAILED DESCRIPTION

Figure 1A:
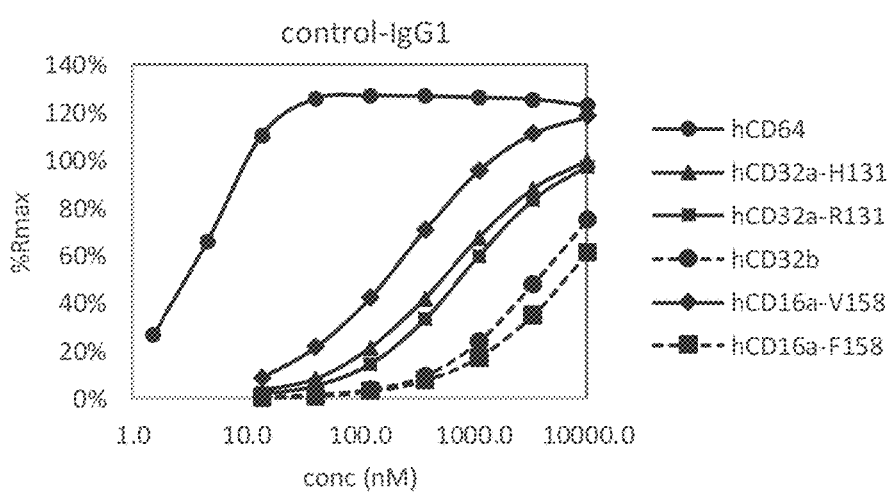

The present disclosure is directed to anti-CD40 antibodies, and in particular, antagonistic anti-CD40 antibodies. For therapeutic targets such as CD40, FcγR-mediated cross-linking of anti-CD40 antibodies has the potential to lead to undesirable agonist signaling and potential for toxicity. The present disclosure also describes antagonistic anti-CD40 antibodies having reduced engagement of the "low affinity" FcγRs: hCD32a/FcγRIIa, hCD32b/FcγRIIb, and hCD16a/FcγRIIIa, as well as reduced engagement to "high affinity" FcγR hCD64. Reduced engagement of low affinity FcγRs is expected to reduce the likelihood of undesirable agonist signaling and undesirable potential for toxicity.

Definitions & Abbreviations

Further abbreviations and definitions are provided below.
APC antigen presenting cells
CD54 also referred to as ICAM-1
CDR complementarity determining regions
CH or CH constant heavy chain
$C_L$ or CL constant light chain
CHO cell Chinese hamster ovary cell
dAb domain antibody
DC dendritic cell
FcgR interchangeable with FcγR
FcγR Fc-gamma-receptor
FR Framework region
GM-CSF granulocyte macrophage colony stimulating factor
HC heavy chain
ICAM-1 intracellular adhesion molecule 1
iDC immature dendritic cells
IFN interferon
IgG immunoglobulin G
IL-6 interleukin-6
LC light chain
mAb monoclonal antibody
mg milligram
ml or mL milliliter
ng nanogram
nM nanomolar
pI isoelectric point SPR surface plasmon resonance
TNF tumor necrosis factor
μg microgram
μM micromolar
V$_L$ or VL variable light chain domain
Vk or VK kappa variable light chain domain
V$_H$ or VH variable heavy chain domain In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

As used here, the term "about" is understood by persons of ordinary skill in the art and will vary to some extent on the context in which it is used. Generally, "about" encompasses a range of values that are plus/minus 10% of a referenced value unless indicated otherwise in the specification.

It is understood that any and all whole or partial integers between the ranges set forth are included herein.

CD40 is also known and referred to as B-cell surface antigen CD40, Bp50, CD40L receptor, CDw40, CDW40, MGC9013, p50, TNFRSF5, and Tumor necrosis factor receptor superfamily member 5. "Human CD40" refers to the CD40 comprising the following amino acid sequence:

```
                                          (SEQ ID NO: 20)
MVRLPLQCVL  WGCLLTAVHP  EPPTACREKQ  YLINSQCCSL

CQPGQKLVSD  CTEFTETECL  PCGESEFLDT  WNRETHCHQH

KYCDPNLGLR  VQQKGTSETD  TICTCEEGWH  CTSEACESCV

LHRSCSPGFG  VKQIATGVSD  TICEPCPVGF  FSNVSSAFEK

CHPWTSCETK  DLVVQQAGTN  KTDVVCGPQD  RLRALVVIPI

IFGILFAILL  VLVFIKKVAK  KPTNKAPHPK  QEPQEINFPD

DLPGSNTAAP  VQETLHGCQP  VTQEDGKESR  ISVQERQ.
```

As used herein, the term "variable domain" refers to immunoglobulin variable domains defined by Kabat et al., Sequences of Immunological Interest, 5th ed., U.S. Dept. Health & Human Services, Washington, D.C. (1991). The numbering and positioning of CDR amino acid residues within the variable domains is in accordance with the well-known Kabat numbering convention. VH, "variable heavy chain" and "variable heavy chain domain" refer to the variable domain of a heavy chain. VL, "variable light chain" and "variable light chain domain" refer to the variable domain of a light chain.

The term "human," when applied to antibodies, means that the antibody has a sequence, e.g., FR and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above.

An "isolated" compound as used herein means that the compound is removed from at least one component with which the compound is naturally associated with in nature.

The anti-CD40 antibody of the present disclosure comprise a variable heavy chain and a variable light chain, each of which contains three complementarity-determining regions (CDRs) and four framework regions (FRs), arranged from amino-terminus to carboxy-terminus in the following order: FR1, CDR1, FR2, CDR2, FR3, CDR3, FR4. The CDRs contain most of the residues that form specific interactions with the antigen and are primarily responsible for antigen recognition.

The anti-CD40 antibody of the present disclosure can comprise CDRs of humanized antibody Y12XX-hz28 (Vh-hz14; Vk-hz2), Y12XX-hz40 (Vh-hz12; Vk-hz3), or Y12XX-hz42 (Vh-hz14; Vk-hz3). An overview of the amino acid sequences of the heavy chain variable region and light chain variable region is provided in Table 1. The table includes a short hand name and a more detailed name for each amino acid sequence, as well as the sequence identifiers.

TABLE 1

| Antibody | HC Variable Region | LC Variable Region |
|---|---|---|
| Y12XX-hz28 | Vh-hz14<br>(Y1268_IGHV1.6908-<br>S54T-N55T-Vh)<br>(SEQ ID NO: 4) | Vk-hz2<br>(Y1258_IGKV1.3902-Vk)<br>(SEQ ID NO: 10) |
| Y12XX-hz40 | Vy-hz12<br>(Y1268_IGHV1.6908-<br>N55Q-Vh)<br>(SEQ ID NO: 13) | Vk-hz3<br>(Y1258_IGKV3.1501-Vk)<br>(SEQ ID NO: 16) |
| Y12XX-hz42 | Vh-hz14<br>(Y1268_IGHV1.6908-<br>S54T-N55T-Vh)<br>(SEQ ID NO: 4) | Vk-hz3<br>(Y1258_IGKV3.1501-Vk)<br>(SEQ ID NO: 16) |

In a specific embodiment, the anti-CD40 antibodies of the present disclosure comprises the CDRs of humanized antibody Y12XX-hz28 (Vh-hz14; Vk-hz2). Detail of the amino acid sequences of Y12XX-hz28 is provided in Table 2.

TABLE 2

| Y12XX-hz28 sequences (Vh-hz14; Vk-hz2) | | |
|---|---|---|
| Heavy chain<br>variable region | QVQLVQSGAEVKKPGSSVKVSCKASGYAFTSYWMHWVRQ<br>APGQGLEWMGQINPTTGRSQYNEKFKTRVTITADKSTST<br>AYMELSSLRSEDTAVYYCARWGLQPFAYWGQGLTVTVSS<br>(SEQ ID NO: 4) | Vh-hz14<br>(SEQ ID NO: 4;<br>CDRs underlined) |
| VH-CDR1 | SYWMH<br>SEQ ID NO: 1) | Amino acids 31-35<br>of SEQ ID NO: 4 |
| VH-CDR2 | QINPTTGRSQYNEKFKT<br>(SEQ ID NO: 2) | Amino acids 50-66<br>of SEQ ID NO: 4 |
| VH-CDR3 | WGLQPFAY<br>(SEQ ID NO: 3) | Amino acids 99-106<br>of SEQ ID NO: 4 |

TABLE 2-continued

Y12XX-hz28 sequences (Vh-hz14; Vk-hz2)

| | | |
|---|---|---|
| HC_Y12XX-hz28-CH1-IgG1-P238K (is IgG1 with and without C-terminal lysine) | QVQLVQSGAEVKKPGSSVKVSCKASGYAFTSYWMHWVRQ APGQGLEWMGQINPTTGRSQYNEKFKTRVTITADKSTST AYMELSSLRSEDTAVYYCARWGLQPFAYWGQGTLVTVSS *ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKR*VEPKSCDKTHTCPPCPAPEL LGGKSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSIDAVEWESNGQPENN YKTTPPVLDSDGSFFLYSKLTVDKSRWQQGNVFSCSVMH EALHNHYTQKSLSLSPG (SEQ ID NO: 5) | CRDs underlined; CH1 = amino acids 118-215 (italicized); IgG1-P238K = amino acids 216-446; P238K underlined; no C-terminal lysine |
| | QVQLVQSGAEVKKPGSSVKVSCKASGYAFTSYWMHWVRQ APGQGLEWMGQINPTTGRSQYNEKFKTRVTITADKSTST AYMELSSLRSEDTAVYYCARWGLQPFAYWGQGTLVTVSS *ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKR*VEPKSCDKTHTCPPCPAPEL LGGKSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSIDAVEWESNGQPENN YKTTPPVLDSDGSFFLYSKLTVDKSRWQQGNVFSCSVMH EALHNHYTQKSLSLSPGK (SEQ ID NO: 6) | CRDs underlined; CH1 = amino acids 118-215 (italicized); IgG1-P238K = amino acids 216-447; P238K underlined; no C-terminal lysine |
| Light chain variable region | DIQMTQSPSFLSASVGDRVTITCKASQDVSTAVAWYQQK PGKAPKLLIYSASYRYTGVPSRFSGSGSGTDFTLTISSL QPEDFATYYCQQHYSTPWTFGGGTKVEIK (SEQ ID NO: 10) | Vk-hz2 (SEQ ID NO: 10; CDRs underlined) |
| VL-CDR1 | KASQDVSTAVA (SEQ ID NO: 7) | Amino acids 24-34 of SEQ ID NO: 10 |
| VL-CDR2 | SASYRYT (SEQ ID NO: 8) | Amino acids 50-56 of SEQ ID NO: 10 |
| VL-CDR3 | QQHYSTPWT (SEQ ID NO: 9) | Amino acids 89-97 of SEQ ID NO: 10 |
| LC_Y12XX-hz28 | DIQMTQSPSFLSASVGDRVTITCKASQDVSTAVAWYQQK PGKAPKLLIYSASYRYTGVPSRFSGSGSGTDFTLTISSL QPEDFATYYCQQHYSTPWTFGGGTKVEIK*RTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC* (SEQ ID NO: 11) | CDRs underlined; CL = amino acids 108-214 (italicized) |

In a specific embodiment, the anti-CD40 antibody of the present disclosure comprises the CDRs of humanized antibody Y12XX-hz40 (Vh-hz12; Vk-hz3). Amino acid sequences of Y12XX-hz40 are provided in Table 3.

TABLE 3

| | | |
|---|---|---|
| Heavy chain variable region | QVQLVQSGAEVKKPGSSVKVSCKASGYAFTSYWMHWVRQ APGQGLEWMGQINPSQGRSQYNEKFKTRVTITADKSTST AYMELSSLRSEDTAVYYCARWGLQPFAYWGQGTLVTVSS (SEQ ID NO: 13) | Vh-hz12 (SEQ ID NO: 13; CDRs underlined) |
| VH-CDR1 | SYWMH (SEQ ID NO: 1) | Amino acids 31-35 of SEQ ID NO: 13 |
| VH-CDR2 | QINPSQGRSQYNEKFKT (SEQ ID NO: 12) | Amino acids 50-66 of SEQ ID NO: 13 |
| VH-CDR3 | WGLQPFAY (SEQ ID NO: 3) | Amino acids 99-106 of SEQ ID NO: 13 |

TABLE 3-continued

Y12XX-hz40 sequences (Vh-hz12; Vk-hz3)

| | | |
|---|---|---|
| HC_Y12XX-hz40-P238K-IgG1a with and without C-terminal lysine | QVQLVQSGAEVKKPGSSVKVSCKASGYAFTSYWMHWVRQ APGQGLEWMGQINPSQGRSQYNEKFKTRVTITADKSTST AYMELSSLRSEDTAVYYCARWGLQPFAYWGQGTLVTVSS *ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKR*VEPKSCDKTHTCPPCPAPEL LGGKSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPG (SEQ ID NO: 14) | CDRs underlined; CH1 = amino acids 118-215 (italicized); IgG1-P238K = amino acids 216-446; P238K underlined; no C-terminal lysine |
| | QVQLVQSGAEVKKPGSSVKVSCKASGYAFTSYWMHWVRQ APGQGLEWMGQINPSQGRSQYNEKFKTRVTITADKSTST AYMELSSLRSEDTAVYYCARWGLQPFAYWGQGTLVTVSS *ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKR*VEPKSCDKTHTCPPCPAPEL LGGKSVFLFPPKPKDTLMISRTPEVTCVVVDVSHEDPEV KFNWYVDGVEVHNAKTKRPEEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK (SEQ ID NO: 15) | CDRs underlined; CH1 = amino acids 118-215 (italicized); IgG1-P238K = amino acids 216-447; P238K underlined; no C-terminal lysine |
| Light chain variable region | EIVMTQSPATLSVSPGERATLSCKASQDVSTAVAWYQQK PGQAPRLLIYSASYRYTGIPARFSGSGSGTEFTLTISSL QSEDFAVYYCQQHYSTPWTFGGGTKVEIK (SEQ ID NO: 16) | Vk-hz3 (SEQ ID NO: 16; CDRs underlined) |
| VL-CDR1 | KASQDVSTAVA (SEQ ID NO: 7) | Amino acids 24-34 of SEQ ID NO: 16 |
| VL-CDR2 | SASYRYT (SEQ ID NO: 8) | Amino acids 50-56 of SEQ ID NO: 16 |
| VL-CDR3 | QQHYSTPWT (SEQ ID NO: 9) | Amino acids 89-97 of SEQ ID NO: 16 |
| LC_Y12XX-hz40 | EIVMTQSPATLSVSPGERATLSCKASQDVSTAVAWYKKQ PGQAPRLLIYSASYRYTGIPARFSGSGSGTEFTLTISSL QSEDFAVYYCQQHYSTPWTFGGGTKVEIKRTVAAPSVFI *FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC* (SEQ ID NO: 17) | CDRs underlined; CL = amino acids 108-214 (italicized) |

In a specific embodiment, the anti-CD40 antibody of the present disclosure comprises the CDRs of humanized antibody Y12XX-hz42 (Vh-hz14; Vk-hz3). Detail of the amino acid sequences of Y12XX-hz42 is provided in Table 4.

TABLE 4

Y12XX-hz42 sequences (Vh-hz14; Vk-hz3)

| | | |
|---|---|---|
| Heavy chain variable region | QVQLVQSGAEVKKPGSSVKVSCKASGYAFTSYWMHWVRQ APGQGLEWMGQINPTTGRSQYNEKFKTRVTITADKSTST AYMELSSLRSEDTAVYYCARWGLQPFAYWGQGTLVTVSS (SEQ ID NO: 4) | Vh-hz14 (SEQ ID NO: 4; CDRs underlined) |
| VH-CDR1 | SYWMH (SEQ ID NO: 1) | Amino acids 31-35 of SEQ ID NO: 4 |
| VH-CDR2 | QINPTTGRSQYNEKFKT (SEQ ID NO: 2) | Amino acids 50-66 of SEQ ID NO: 4 |
| VH-CDR3 | WGLQPFAY (SEQ ID NO: 3) | Amino acids 99-106 of SEQ ID NO: 4 |

TABLE 4-continued

Y12XX-hz42 sequences (Vh-hz14; Vk-hz3)

| | | |
|---|---|---|
| HC_Y12XX-hz40-<br>P238K-IgG1a<br>with and without<br>C-terminal<br>lysine | QVQLVQSGAEVKKPGSSVKVSCKASGYAFTSYWMHWVRQ<br>APGQGLEWMGQINPTTGRSQYNEKFKTRVTITADKSTST<br>AYMELSSLRSEDTAVYYCARWGLQPFAYWGQGTLVTVSS<br>*ASTKGPSVFPLAPSSKSTSGGTAALGCLVKDYFPEPVTV*<br>*SWNSGALTSGVHTFPAVLQSSGLYSLSSVVTVPSSSLGT*<br>*QTYICNVNHKPSNTKVDKR*VEPKSCDKTHTCPPCPAPEL<br>LGGKSVFLFPPKPKDLTMISRTPEVTCVVVDVSHEDPEV<br>KFNWYVDGVEVHNAKTKPREEQYNSTYRVVSVLTVLHQD<br>WLNGKEYKCKVSNKALPAPIEKTISKAKGQPREPQVYTL<br>PPSRDELTKNQVSLTCLVKGFYPSDIAVEWESNGQPENN<br>YKTTPPVLDSDGSFFLYSKLTVDKSRWQQGNVFSCSVMH<br>EALHNHYTQKSLSLSPG<br>(SEQ ID NO: 5) | CRDs underlined;<br>CH1 = amino acids<br>118-215 (italicized);<br>IgG1-P238K = amino<br>acids 216-446; P238K<br>underlined; no<br>C-terminal lysine |
| | QVQLVQSGAEVKKPGSSVKVSCKASGYAFTSYWMHWVRQ<br>APGQGLEWMGQINPTTGRSQYNEKFKTRVTITADKSTST<br>AYMELSSLRSEDTAVYYCARWGLQPFAYWGQGTLVTVSS<br>*ASTKGPSVFPLAPSSKSTSGGTAALGCLVKDYFPEPVTV*<br>*SWNSGALTSGVHTFPAVLQSSGLYSLSSVVTVPSSSLGT*<br>*QYTICNVNHKPSNTKVDKR*VEPKSCDKTHTCPPCPAPEL<br>LGGKSVFLFPPKPKDLTMISRTPEVTCVVVDVSHEDPEV<br>KFNWYVDGVEVHNAKTKPREEQYNSTYRVVSVLTVLHQD<br>WLNGKEYKCKVSNKALPAPIEKTISKAKGQPREPQVYTL<br>PPSRDELTKNQVSLTCLVKGFYPSDIAVEWESNGQPENN<br>YKTTPPVLDSDGSFFLYSKLTVDKSRWQQGNVFSCSVMH<br>EALHNHYTQKSLSLSPGK<br>(SEQ ID NO: 6) | CRDs underlined;<br>CH1 = amino acids<br>118-215 (italicized);<br>IgG1-P238K = amino<br>acids 216-447; P238K<br>underlined; no<br>C-terminal lysine |
| Light chain<br>variable region | EIVMTQSPATLSVSPGERATLSCKASQDVSTAVAWYQQK<br>PGQAPRLLIYSASYRYTGIPARFSGSGSGTEFTLTISSL<br>QSEDFAVYYCQQHYSTPWTFGGGTKVEIK<br>(SEQ ID NO: 16) | Vk-hz3<br>(SEQ ID NO: 16;<br>CDRs underlined) |
| VL-CDR1 | KASQDVSTAVA<br>(SEQ ID NO: 7) | Amino acids 24-34<br>of SEQ ID NO: 16 |
| VL-CDR2 | SASYRYT<br>(SEQ ID NO: 8) | Amino acids 50-56<br>of SEQ ID NO: 16 |
| VL-CDR3 | QQHYSTPWT<br>(SEQ ID NO: 9) | Amino acids 89-97<br>of SEQ ID NO: 16 |
| LC_Y12XX-hz42 | EIVMTQSPATLSVSPGERATLSCKASQDVSTAVAWYQQK<br>PGQAPRLLIYSASYRYTGIPARFSGSGSGTEFTLTISSL<br>QSEDFAVYYCQQHYSTPWTFGGGTKVEIK*RTVAAPSVFI*<br>*FPPSDEQLKSGTASVVCLLNNFYPREAKVQWKVDNALQS*<br>*GNSQESVTEQDSKDSTYSLSSTLTLSKADYEKHKVYACE*<br>*VTHQGLSSPVTKSFNRGEC*<br>(SEQ ID NO: 17) | CDRs underlined;<br>CL = amino acids<br>108-214 (italicized) |

In one embodiment, the antibodies of the disclosure can comprise the amino acid sequences of the CDR1, CDR2, and CDR3 regions of the humanized Y12XX-hz28 variable heavy and light chains sequences (see e.g., SEQ ID NOS: 4 and 10 respectively, as an example). Monoclonal antibodies contain all 6 CDRs (3 for the $V_H$ and 3 for the $V_L$), for example, SYWMH (SEQ ID NO: 1), QINPTTGRSQYNEKFKT (SEQ ID NO: 2), and WGLQPFAY (SEQ ID NO: 3) for the variable heavy chain CDRs 1-3 respectively and KASQDVSTAVA (SEQ ID NO: 7), SASYRYT (SEQ ID NO: 8), and QQHYSTPWT (SEQ ID NO: 9) for the variable light chain CDRs 1-3 respectively.

In one embodiment, the antibodies of the disclosure can comprise the amino acid sequences of the CDR1, CDR2, and CDR3 regions of the humanized Y12XX-hz40 variable heavy and light chains sequences (see e.g., SEQ ID NOS: 13 and 16 respectively, as an example). Monoclonal antibodies contain all 6 CDRs (3 for the $V_H$ and 3 for the $V_L$), for example, SYWMH (SEQ ID NO: 1), QINPSQGRSQYNEKFKT (SEQ ID NO: 12), and WGLQPFAY (SEQ ID NO: 3) for the variable heavy chain CDRs 1-3 respectively and KASQDVSTAVA (SEQ ID NO: 7), SASYRYT (SEQ ID NO: 8), and QQHYSTPWT (SEQ ID NO: 9) for the variable light chain CDRs 1-3 respectively.

In one embodiment, the antibodies of the disclosure can comprise the amino acid sequences of the CDR1, CDR2, and CDR3 regions of the humanized Y12XX-hz42 variable heavy and light chains sequences (see e.g., SEQ ID NOS: 4 and 16 respectively, as an example). Monoclonal antibodies contain all 6 CDRs (3 for the $V_H$ and 3 for the $V_L$), for example, SYWMH (SEQ ID NO: 1), QINPTTGRSQYNEKFKT (SEQ ID NO: 2), and WGLQPFAY (SEQ ID NO: 3) for the variable heavy chain CDRs 1-3 respectively and KASQDVSTAVA (SEQ ID NO: 7), SASYRYT (SEQ ID NO: 8), and QQHYSTPWT (SEQ ID NO: 9) for the variable light chain CDRs 1-3 respectively.

An "antibody" (Ab) shall include, without limitation, an immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as V$_L$) and a light chain constant region. The light chain constant region comprises one constant domain, C$_L$. The V$_H$ and V$_L$ regions can be further subdivided into regions of hypervariability, termed complementarity determining regions (CDRs), interspersed with regions that are more conserved, termed framework regions (FR). Each V$_H$ and V$_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

An "antigen binding portion" of an Ab (also called an "antigen-binding fragment") or antigen binding portion thereof refers to one or more sequences of an Ab (full length or fragment of the full length antibody) that retain the ability to bind specifically to the antigen bound by the whole Ab. Examples of an antigen-binding fragment include Fab, F(ab')$_2$, scFv (single-chain variable fragment), Fab', dsFv, sc(Fv)2, and scFv-Fc.

A "humanized" antibody refers to an Ab in which some, most or all of the amino acids outside the CDR domains of a non-human Ab are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

A "chimeric antibody" refers to an Ab in which the variable regions are derived from one species and the constant regions are derived from another species, such as an Ab in which the variable regions are derived from a mouse Ab and the constant regions are derived from a human Ab.

As used herein, "specific binding" refers to the binding of an antigen by an antibody with a dissociation constant (K$_d$) of about 1 μM or lower as measured, for example, by surface plasmon resonance (SPR). Suitable assay systems include the BIAcore™ (GE Healthcare Life Sciences, Marlborough, Mass.) surface plasmon resonance system and BIAcore™ kinetic evaluation software (e.g., version 2.1).

Binding of the present antibodies to CD40 antagonizes at least one CD40 activity. "CD40 activities" include, but are not limited to, T cell activation (e.g., induction of T cell proliferation or cytokine secretion), macrophage activation (e.g., the induction of reactive oxygen species and nitric oxide in the macrophage), and B cell activation (e.g., B cell proliferation, antibody isotype switching, or differentiation to plasma cells). CD40 activities can be mediated by interaction with other molecules. "CD40 activities" include the functional interaction between CD40 and the following molecules, which are identified by their Uniprot Accession Number is parentheses:

| | |
|---|---|
| CALR | (P27797); |
| ERP44 | (Q9BS26); |
| FBL | (P22087); |
| POLR2H | (P52434); |
| RFC5 | (P40937); |
| SGK1 | (O00141); |
| SLC30A7 | (Q8NEW0); |
| SLC39A7 | (Q92504); |

-continued

| | |
|---|---|
| TRAF2 | (Q5T1L5); |
| TRAF3 | (Q13114); |
| TRAF6 | (Q9Y4K3); |
| TXN | (Q5T937); |
| UGGT1 | (Q9NYU2); and |
| USP15 | (Q9Y4E8). |

For example, a CD40 "activity" includes an interaction with TRAF2. CD40/TRAF2 interaction activates NF-κB and JNK. See Davies et al., Mol. Cell Biol. 25: 9806-19 (2005). This CD40 activity thus can be determined by CD40-dependent cellular NF-κB and JNK activation, relative to a reference.

As used herein, the terms "activate," "activates," and "activated" refer to an increase in a given measurable CD40 activity by at least 10% relative to a reference, for example, at least 10%, 25%, 50%, 75%, or even 100%, or more. A CD40 activity is "antagonized" if the CD40 activity is reduced by at least 10%, and in an exemplary embodiment, at least about 20%, 30%, 40%, 50%, 60%, 70%, 80%, 90%, 95%, 97%, or even 100% (i.e., no detectable activity), relative to the absence of the antagonist. For example, an antibody may antagonize some or all CD40 activity, while not activating CD40. For example, the antibody may not activate B cell proliferation. The antibody may not activate cytokine secretion by T cells, where the cytokine is at least one cytokine selected from the group consisting of IL-2, IL-6, IL-10, IL-13, TNF-α, and IFN-γ.

Variable domains may comprise one or more framework regions (FR) with the same amino acid sequence as a corresponding framework region encoded by a human germline antibody gene segment. Preferred framework sequences for use in the antibodies described herein are those that are structurally similar to the framework sequences used by antibodies described herein. The V$_H$ CDR1, 2 and 3 sequences, and the V$_L$ CDR1, 2 and 3 sequences, can be grafted onto framework regions that have the identical sequence as that found in the germline immunoglobulin gene from which the framework sequence derive, or the CDR sequences can be grafted onto framework regions that contain up to 20, preferably conservative, amino acid substitutions as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Exemplary framework regions include but are not limited to those in Tables 5 and 6 below.

TABLE 5

| Heavy Framework Region | Sequence |
|---|---|
| FR1 | Amino acid residues 1-30 of any VH sequence in Table 8 (SEQ ID NOs: 53-75) or Table 10 (SEQ ID NOs: 4, 13, and 99-113) in the Examples |
| FR2 | Amino acid residues 36-49 of any VH sequence in Table 8 (SEQ ID NOs: 53-75) or Table 10 (SEQ ID NOs: 4,13, and 99-113) in the Examples |
| FR3 | Amino acid residues 67-98 of any VH sequence in Table 8 (SEQ ID NOs: 53-75) or Table 10 (SEQ ID NOs: 4,13, and 99-113) in the Examples |

TABLE 5-continued

| Heavy Framework Region | Sequence |
|---|---|
| FR4 | Amino acid residues 107-117 of any VH sequence in Table 8 (SEQ ID NOs: 53-75) or Table 10 (SEQ ID NOs: 4, 13, and 99-113) in the Examples |

TABLE 6

| Light Framework Region | Sequence |
|---|---|
| FR1 | Amino acid residues 1-23 of any VL sequence in Table 8 (SEQ ID NOs: 76-98) or Table 10 (SEQ ID NOs: 10, 16, and 114-116) in the Examples |
| FR2 | Amino acid residues 35-49 of any VL sequence in Table 8 (SEQ ID NOs: 76-98) or Table 10 (SEQ ID NOs: 10, 16, and 114-116) in the Examples |
| FR3 | Amino acid residues 57-88 of any VL sequence in Table 8 (SEQ ID NOs: 76-98) or Table 10 (SEQ ID NOs: 10, 16, and 114-116) in the Examples |
| FR4 | Amino acid residues 98-107 of any VL sequence in Table 8 (SEQ ID NOs: 76-98) or Table 10 (SEQ ID NOs: 10, 16, and 114-116) in the Examples |

A variant variable domain may differ from the variable domain of the humanized Y12XX-hz28, Y12XX-hz40, or Y12XX-hz42 sequence by up to 10 amino acids or any integral value between, where the variant variable domain specifically binds CD40. Alternatively, the variant variable domain may have at least 90% sequence identity (e.g., at least 92%, 95%, 98%, or 99% sequence identity) relative to the sequence of the humanized Y12XX-hz28, Y12XX-hz40, or Y12XX-hz42 sequence, respectively. Non-identical amino acid residues or amino acids that differ between two sequences may represent amino acid substitutions, additions, or deletions. Residues that differ between two sequences appear as non-identical positions, when the two sequences are aligned by an appropriate amino acid sequence alignment algorithm, such as BLAST® (a registered trademark of the U.S. National Library of Medicine).

Exemplary CD40 antibodies of the present invention can include an isolated antibody, or antigen binding portion thereof, that specifically binds to human CD40, wherein said antibody comprises a first polypeptide portion comprising a heavy chain variable region, and a second polypeptide portion comprising a light chain variable region, wherein:

said heavy chain variable region comprises one of (i) a CDR1 comprising SYWMH (SEQ ID NO: 1), a CDR2 comprising QINPTTGRSQYNEKFKT (SEQ ID NO: 2), a CDR3 comprising WGLQPFAY (SEQ ID NO: 3) and (ii) a CDR1 comprising SYWMH (SEQ ID NO: 1), a CDR2 comprising QINPSQGRSQYNEKFKT (SEQ ID NO: 12), a CDR3 comprising WGLQPFAY (SEQ ID NO: 3); and said light chain variable region comprises a CDR1 comprising KASQDVSTAVA (SEQ ID NO: 7), a CDR2 comprising SASYRYT (SEQ ID NO: 8), and a CDR3 comprising QQHYSTPWT (SEQ ID NO: 9).

The isolated antibody or antigen binding portion thereof can antagonize one or more activities of CD40. The isolated antibody or antigen binding portion thereof can be a chimeric antibody. Exemplary heavy and light variable chains for a chimeric antibody are in Table 8 of the Examples. The isolated antibody or antigen binding portion thereof can be a humanized antibody. Exemplary humanized heavy and light variable chains are in Table 10 of the Examples. The isolated antibody or antigen binding portion thereof can comprise a human heavy chain constant region and a human light chain constant region.

Fc Domain and Constant Region

The carboxyl-terminal "half" of a heavy chain defines a constant region (Fc) and which is primarily responsible for effector function. As used herein, the term "Fc domain" refers to the constant region antibody sequences comprising CH2 and CH3 constant domains as delimited according to Kabat et al., Sequences of Immunological Interest, 5$^{th}$ ed., U.S. Dept. Health & Human Services, Washington, D.C. (1991). The Fc region may be derived from a human IgG. For instance, the Fc region may be derived from a human IgG1 or a human IgG4 Fc region. A heavy variable domain can be fused to an Fc domain. The carboxyl terminus of the variable domain may be linked or fused to the amino terminus of the Fc CH2 domain. Alternatively, the carboxyl terminus of the variable domain may be linked or fused to the amino terminus of a linker amino acid sequence, which itself is fused to the amino terminus of an Fc domain. Alternatively, the carboxyl terminus of the variable domain may be linked or fused to the amino terminus of a CH1 domain, which itself is fused to the Fc CH2 domain. Optionally, the protein may comprise the hinge region after the CH1 domain in whole or in part. Optionally an amino acid linker sequence is present between the variable domain and the Fc domain. The carboxyl terminus of the light variable domain may be linked or fused to the amino terminus of a CL domain.

An exemplary sequence for a heavy chain CH1 is amino acids 118-215 of SEQ ID NO: 5 (ASTKGPSVF-PLAPSSKSTSGGTAALGCLVKDYF-PEPVTVSWNSGALTSGVHTFPAVLQ SSGLYS-LSSVVTVPSSSLGTQTYICNVNHKPSNTKVDKRV; SEQ ID NO: 18). An exemplary sequence for a light chain CL is amino acids 108-214 of SEQ ID NO: 11

(RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVT

KSFNRGEC;SEQ ID NO: 19).

The antibody can be a fusion antibody comprising a first variable domain that specifically binds human CD40, and a second domain comprising an Fc domain.

Exemplary Fc domains used in the fusion protein can include human IgG domains. Exemplary human IgG Fc domains include IgG4 Fc domain and IgG1 Fc domain. While human IgG heavy chain genes encode a C-terminal lysine, the lysine is often absent from endogenous antibodies as a result of cleavage in blood circulation. Antibodies having IgG heavy chains including a C-terminal lysine, when expressed in mammalian cell cultures, may also have variable levels of C-terminal lysine present (Cai et al, 2011, Biotechnol Bioeng. 108(2): 404-12). Accordingly, the C-terminal lysine of any IgG heavy chain Fc domain disclosed herein may be omitted.

The isolated antibody or antigen binding portion thereof described herein, can comprise an Fc domain which comprises an amino acid sequence of:
EPKSCDKTHTCPPCPAPELLGG(P/K)
SVFLFPPKPKDTLMISRTPEVTCVV VDVSHEDPE-
VKFNWYVDGVEVHNAKTKPREEQY(N/A)
STYRVVSVLTVLHQDWLN
GKEYKCKVSNKALPA-
PIEKTISKAKGQPREPQVYTLPPSR(D/E)E(L/M)

TKNQVSLTC LVKGFYPSDIAVEWESNGQPEN-NYKTTPPVLDSDGSFFLYSKLTVDKSRWQQGNVFSCSVMHEALHNHYTQKSLSLSPG(K/not present) (Fc consensus; SEQ ID NO: 21). The parenthetical notation indicates possible amino acid identities at the position. For instance, Kabat position 238 can be either Proline (P) or Lysine (K), which is notated as (P/K). Additional exemplary, non-limiting consensus sequences are SEQ ID NOs: 118-120.

The isolated antibody or antigen binding portion thereof described herein can comprise a human IgG1 Fc domain comprising a mutation at Kabat position 238 that reduces binding to Fc-gamma-receptors (FcγRs), wherein proline 238 (P238) is mutated to one of the residues selected from the group consisting of lysine (K), serine (S), alanine (A), arginine (R) and tryptophan (W), and wherein the antibody or antigen binding portion thereof has reduced FcγR binding. The isolated antibody or antigen binding portion thereof described herein can have P238 mutated to lysine in a human IgG1 Fc domain.

The isolated antibody or antigen binding portion thereof comprises an Fc domain which comprises an amino acid sequence selected from: SEQ ID NOs: 22-29.

Exemplary sequences comprising the IgG1 Fc domains above include: SEQ ID NO: 5, SEQ ID NO: 6, SEQ ID NO: 30, and SEQ ID NO: 31.

The isolated antibody or antigen binding portion thereof described herein can comprise a human IgG1 Fc domain comprising an alanine substituted at Kabat position 297. For example, the isolated antibody or antigen binding portion thereof comprises an Fc domain which comprises an amino acid sequence selected from: SEQ ID NOs: 32-39.

The isolated antibody or antigen binding portion described herein may comprise (1) a variable heavy chain ($V_H$) selected from Table 8 or Table 10 in the Examples, or the CDRs thereof, and/or (2) a variable light chain ($V_L$) selected from Table 8 or Table 10 in the Examples, or the CDRs thereof.

The isolated antibody or antigen binding portion thereof disclosed herein may comprise a heavy chain amino acid sequence selected from Vh-hz12 (SEQ ID NO: 13) and Vh-hz14 (SEQ ID NO: 4).

The isolated antibody or antigen binding portion thereof disclosed herein may comprise a light chain amino acid sequence selected from Vk-hz2 (SEQ ID NO: 10) and Vk-hz3 (SEQ ID NO: 16).

The isolated antibody or antigen binding portion thereof disclosed herein may be an antibody selected from the group consisting of:
a) Y12XX-hz28-P238K having a heavy chain of SEQ ID NO: 5 or 6 and light chain of SEQ ID NO: 11;
b) Y12XX-hz40-P238K having a heavy chain of SEQ ID NO: 14 or 15 and light chain of SEQ ID NO: 17; and
c) Y12XX-hz42-P238K having a heavy chain of SEQ ID NO: 5 or 6 and light chain of SEQ ID NO: 17.

The antibody or antigen binding portion thereof disclosed herein, wherein the antigen binding portion is selected from the group consisting of Fv, Fab, F(ab')2, Fab', dsFv, scFv, sc(Fv)$_2$, diabodies, and scFv-Fc.

The antibody or antigen binding portion thereof disclosed herein can be an immunoconjugate, wherein the antibody or antigen-binding portion thereof is linked to a therapeutic agent.

The antibody or antigen binding portion thereof disclosed herein can be a bispecific antibody, wherein the antibody or antigen-binding portion thereof is linked to a second functional moiety having a different binding specificity than said antibody or antigen binding portion thereof.

The antibody or antigen binding portion thereof disclosed herein can further comprise an additional moiety.

The variable regions of the present antibodies may optionally be linked to the Fc domain by an "amino acid linker" or "linker." For example, the C-terminus of a variable heavy chain domain may be fused to the N-terminus of an amino acid linker, and an Fc domain may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include GGGGS (SEQ ID NO: 40), and a linker comprising 2, 3, 4, or 5 copies of GGGGS (SEQ ID NOs: 41 to 44, respectively). TABLE 7 lists suitable linker sequences for use in the present disclosure.

TABLE 7

| Representative Linker Sequences | |
| --- | --- |
| GGGGS | SEQ ID NO: 40 |
| (GGGGS)$_2$ | SEQ ID NO: 41 |
| (GGGGS)$_3$ | SEQ ID NO: 42 |
| (GGGGS)$_4$ | SEQ ID NO: 43 |
| (GGGGS)$_5$ | SEQ ID NO: 44 |
| AST | SEQ ID NO: 45 |
| TVAAPS | SEQ ID NO: 46 |
| TVA | SEQ ID NO: 47 |
| ASTSGPS | SEQ ID NO: 48 |

Antibody Preparation

The antibody can be produced and purified using ordinary skill in a suitable mammalian host cell line, such as CHO, 293, COS, NSO, and the like, followed by purification using one or a combination of methods, including protein A affinity chromatography, ion exchange, reverse phase techniques, or the like.

As well known in the art, multiple codons can encode the same amino acid. Nucleic acids encoding a protein sequence thus include nucleic acids having codon degeneracy. The polypeptide sequences disclosed herein can be encoded by a variety of nucleic acids. The genetic code is universal and well known. Nucleic acids encoding any polypeptide sequence disclosed herein can be readily conceived based on conventional knowledge in the art as well as optimized for production. While the possible number of nucleic acid sequence encoding a given polypeptide is large, given a standard table of the genetic code, and aided by a computer, the ordinarily skilled artisan can easily generate every possible combination of nucleic acid sequences that encode a given polypeptide.

A representative nucleic acid sequence encoding the Y12XX heavy chain variable domain of Y12XX-hz28 including a constant region CH1 and Fc domain IgG1-

P238K is: ATGAGGGCTTGGATCTTCTTTCTGCTCTGCCTGGCCGGGAGAGCGCTCGCACAGGTGCAGCTGGTGCAGTCTGGTGCCGAGGTCAAAAAGCCAGGCTCCAGCGTGAAGGTGAGCTGCAAGGCCTCTGGCTACGCTTTCACCTCTTATTGGATGCACTGGGTGAGACAGGCTCCTGGACAGGGCCTGGAGTGGATGGGCCAGATCAACCCAACCACCGGCAGAAGCC AGTACAATGAGAAGTTTAAGACCCGCGTGACCATCACAGCCGACAAGTCCACCAGCACAGCTTATATGGAGCTGTCTTCCCTGAGGTCCGAGGATACAGCCGTGTACTATTGCGCTCGGTGGGGCCTGCAGCCTTTCGCTTACTGGGGCCAGGGCACCCTGGTGACAGTGAGCTCTGCTAGCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGG CCGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAGAGTTGAGCCCAAATCTTGTGACAAAACTCACACATGCCCACCGTGCCCAGCACCTGAACTCCTGGGGGAAAGTCAGTCTTCCTCTTCCCCCCAAAACCCAAGGACACCCTCATGATCTCCCGGACCCCTGAGGTCACATGCGTGGTGGTGGACGT GAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTC AGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGATGAGCTGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCA CTACACGCAGAAGAGCCTCTCCCTGTCTCCGGGTTGA (SEQ ID NO: 49). In this sequence, nucleotides 1-51 encode a signal peptide (optional), nucleotides 52-402 encode the heavy chain variable region in which nucleotides 141-155 encode CDR1, nucleotides 198-249 encode CDR2, and nucleotides 346-369 encode CDR3 of the Y12XX variable domain of the heavy chain. Nucleotides 403-696 encode a CH1 domain, and nucleotides 697-1399 encode IgG1-P238K. Nucleotides 1400-1402 are a stop codon.

A representative nucleic acid sequence encoding the Y12XX light chain variable domain of Y12XX-hz28 including a constant region CL is: ATGAGGGCTTGGATCTTCTTTCTGCTCTGCCTGGCCGGGCGCGCCTT GGCCGACATC CAGATGACCCAGTCCCCCTCCTTCCTGTCTGCCTCC GTGGGCGACAGAGTGACCATC ACCTGTAAGGCTTCCCAGGATGTGAGCACAGCCGTGGCTTGGTACCAGCAGAAGCC AGGCAAGGCCCCCAAGCTGCTGATCTATTCCGCCTCTTACAGGTATACCGGCGTGCCCTCTCGGTTCTCCGGCAGCGGCTCTGGCACAGACTTTACCCTGACAATCTCCAGCCT GCAGCCTGAGGATTTCGCCACCTACTATTGCCAGCAGCACTACTCCACCCCATGGACATTTGGCGGCGGCACCAAGGTGGAGATCAAGCGTACGGTGGCTGCACCATCTGTCTT CATCTTCCCGCCATCTGATGAGCAGTTGAAATCTGGAACTGCCTCTGTTGTGTGCCTG CTGAATAACTTCTATCCCAGAGAGGCCAAAGTACAGTGGAAGGTGGATAACGCCCT CCAATCGGGTAACTCCCAGGAGAGTGTCACAGAGCAGGACAGCAAGGACAGCACCT ACAGCCTCAGCAGCACCCTGACGCTGAGCAAAGCAGACTACGAGAAACACAAAGTC TACGCCTGCGAAGTCACCCATCAGGGCCTGAGCTCGCCCGTCACAAAGAGCTTCAA CAGGGGAGAGTGTTAG (SEQ ID NO: 50). In this sequence, nucleotides 1-51 encode a signal peptide (optional), nucleotides 52-372 encode the light chain variable region in which nucleotides 121-153 encode CDR1, nucleotides 199-219 encode CDR2, and nucleotides 316-342 encode CDR3. Nucleotides 373-693 encode a CL. Nucleotides 694-696 are a stop codon The coding sequence for the heavy and/or light chain optionally may encode a signal peptide, such as MRAWIFFLLCLAGRALA (SEQ ID NO: 51), at the 5' end of the coding sequence. As described above, an exemplary nucleic acid coding sequence for this signal peptide is ATGAGGGCTTGGATCTTCTTTCTGCTCTGCCTGGCCGGGAGAGCGCTCGCA (SEQ ID NO: 52).

Accordingly, a nucleic acid encoding an antibody disclosed herein is also contemplated. Such a nucleic acid may be inserted into a vector, such as a suitable expression vector, e.g., pHEN-1 (Hoogenboom et al. (1991) *Nucleic Acids Res.* 19: 4133-4137). Further provided is an isolated host cell comprising the vector and/or the nucleic acid.

The antibody of the disclosure can be produced and purified using only ordinary skill in any suitable mammalian host cell line, such as CHO (Chinese hamster ovary cells), 293 (human embryonic kidney 293 cells), COS cells, NSO cells, and the like, followed by purification using one or a combination of methods, including protein A affinity chromatography, ion exchange, reverse phase techniques, or the like.

Pharmaceutical Compositions and Methods of Treatment

A pharmaceutical composition comprises a therapeutically-effective amount of one or more antibodies and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are known in the art. See, e.g., Remington, THE SCIENCE AND PRACTICE OF PHARMACY, A. Gennaro, et al., eds., 21st ed., Mack Publishing Co. (2005).

The pharmaceutical composition may be administered alone or in combination therapy, (i.e., simultaneously or sequentially) with an immunosuppressive/immunomodulatory and/or anti-inflammatory agent. An exemplary type of agent is a cytotoxic T lymphocyte-associated protein 4 (CTLA4) mutant molecule. An exemplary CTLA4 mutant molecule is L104EA29Y-Ig (belatacept) which is a modified CTLA4-Ig. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

A method of treating an immune disease in a patient in need of such treatment may comprise administering to the patient a therapeutically effective amount of the antibody, or antigen binding portion thereof, as described herein. Further provided is a method of treating or preventing an autoimmune or inflammatory disease in a patient in need of such treatment may comprise administering to the patient a therapeutically effective amount of the antibody, or antigen binding portion thereof, as described herein. Also provided is the use of an antibody, or antigen binding portion thereof, of the disclosure, or a pharmaceutically acceptable salt thereof, for treating an immune disease in a patient in need of such treatment and/or for treating or preventing an autoimmune or inflammatory disease in a patient in need of such treatment, that may comprise administering to the patient a therapeutically effective amount of the antibody, or antigen binding portion thereof. Antagonizing CD40-mediated T cell activation could inhibit undesired T cell responses occurring during autoimmunity, transplant rejection, or allergic responses, for example. Inhibiting CD40-mediated T cell activation could moderate the progression and/or severity of these diseases.

The use of an antibody, or antigen binding portion thereof, of the disclosure, or a pharmaceutically acceptable salt thereof, in the preparation of a medicament for treatment of an immune disease and/or for treating or preventing an autoimmune or inflammatory disease in a patient in a patient in need of such treatment, is also provided. The medicament can, for example, be administered in combination with an immunosuppressive/immunomodulatory and/or anti-inflammatory agent.

As used herein, a "patient" means an animal, e.g., mammal, including a human. The patient may be diagnosed with an immune disease. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to, inflammation, allergy, autoimmune disease, or graft-related disease. Thus, the patient may be diagnosed with an autoimmune disease or inflammatory disease. An "autoimmune disease" refers to any disease associated with the development of an autoimmune reaction in an individual, including a cellular and/or a humoral immune reaction. An example of an autoimmune disease is inflammatory bowel disease (IBD), including, but not limited to ulcerative colitis and Crohn's disease. Other autoimmune diseases include systemic lupus erythematosus, multiple sclerosis, rheumatoid arthritis, diabetes, psoriasis, scleroderma, and atherosclerosis. Graft-related diseases include graft versus host disease (GVHD), acute transplantation rejection, and chronic transplantation rejection.

Diseases that can be treated by administering the antibody of the disclosure may be selected from the group consisting of Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), lupus nephritis, systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

The pharmaceutical composition may be administered alone or as a combination therapy, (i.e., simultaneously or sequentially) with an immunosuppressive/immunomodulatory and/or anti-inflammatory agent. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

Any suitable method or route can be used to administer the antibody, or antigen binding portion thereof, or the pharmaceutical composition. Routes of administration include, for example, intravenous, intraperitoneal, subcutaneous, or intramuscular administration. A therapeutically effective dose of administered antibody depends on numerous factors, including, for example, the type and severity of the immune disease being treated, the use of combination therapy, the route of administration of the antibody, or antigen binding portion thereof, or pharmaceutical composition, and the weight of the patient. A non-limiting range for a therapeutically effective amount of a domain antibody is 0.1-20 milligram/kilogram (mg/kg), and in an aspect, 1-10 mg/kg, relative to the body weight of the patient.

Kits

A kit useful for treating an immune disease in a human patient is provided. A kit useful for treating or preventing an autoimmune disease or inflammatory disease in a human patient is also provided. The kit can comprise (a) a dose of an antibody, or antigen binding portion thereof, of the present disclosure and (b) instructional material for using the antibody, or antigen binding portion thereof, in the method of treating an immune disease, or for using the antibody, or antigen binding portion thereof, in the method of treating or preventing an autoimmune or inflammatory disease, in a patient.

"Instructional material," as that term is used herein, includes a publication, a recording, a diagram, or any other medium of expression, which can be used to communicate the usefulness of the composition and/or compound of the invention in a kit. The instructional material of the kit may, for example, be affixed to a container that contains the compound and/or composition of the invention or be shipped together with a container, which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

EXAMPLES

Example 1: Binding of Mouse Anti-Human CD40 Antibodies to Human CD40

Mouse anti-human-CD40 antibodies were generated and were tested for binding to human CD40 by surface plasmon resonance (SPR). The Vh and Vk sequences for each antibody are shown in Table 8.

TABLE 8

Mouse anti-human-CD40 variable heavy and light sequences

| ID | VH Sequence | VL Sequence |
|---|---|---|
| ADX_Y1060.ZZ0-1 | ADX_Y1060.ZZ0-1-Vh<br>QVQLVQSGAEVKKPGASVKVSCKASG<br>YTFTGYYMHWVRQAPGQGLEWMGWIN<br>PDSGGTNYAQKFQGRVTMTRDTSIST<br>AYMELNRLRSDDTAVYYCARDQPLGY<br>CTNGVCSYFDYWGQGTLVTVSS<br>(SEQ ID NO: 53) | ADX_Y1060.ZZ0-1-Vk<br>DIQMTQSPSSVSASVGDRVTITCRASQ<br>GIYSWLAWYQQKPGKAPNLLIYTASTL<br>QSGVPSRFSGSGSGTDFTLTISSLQPE<br>DFATYYCQQANIFPLTFGGGTKVEIK<br>(SEQ ID NO: 76) |
| ADX_Y1072.ZZ0-1 | ADX_Y1072.ZZ0-1-Vh<br>QVQFQQSGAELARPGASVKLSCKASG<br>YTFTSYWMQWVKQRPGQGLEWIGTIY<br>PGDGDSRYNQKFKGKALLTADKSSSI<br>AYMQLNSLASEDSAVYFCARFSLYDG<br>YPYYFDYWGQGTTLTVSS<br>(SEQ ID NO: 54) | ADX_Y1072.ZZ0-1-Vk<br>DVVMTQTPLSLPVSLGDQASISCRSSQ<br>SLVHRNGNTYLHWYLQKPGQSPKLLIY<br>RVSNRFSGVPDRFSGSGSGTDFTLKIS<br>RVEAEDLGIYFCSQSTHFPYTFGGGTK<br>LEIK<br>(SEQ ID NO: 77) |
| ADX_Y1234.ZZ0-1 | ADX_Y1234.ZZ0-1-Vh<br>EVQLVESGGGLVKPGGSLKLSCAASG<br>FAFSSYDMSWVRQTPEKRLEWVAYIN<br>SGVGNTYYPDTVKGRFTISRDNAKNT<br>DIADYYCQQINSWPLTFGAGTKLELK<br>LYLQMSSLKSEDTAMYYCARHGNYAW<br>FAYWGQGTLVTVSA<br>(SEQ ID NO: 55) | ADX_Y1234.ZZ0-1-Vk<br>DILLTQSPAILSVSPGERVSFSCRASQ<br>SIGTSIHWYQQRTIGSPRLLIKYASES<br>ISGIPSRFSGSGSGTDFTLSINSVESE<br>(SEQ ID NO: 78) |
| ADX_Y1236.ZZ0-1 | ADX_Y1236.ZZ0-1-Vh<br>DVQLVESGGGLVQPGGSRKLSCAASG<br>FTFSSFGMHWVRQAPEKGLEWVAYIS<br>SGSSTIYYADTVKGRFTISRDNPKNT<br>LFLQMTSLRSEDTAMYYCARYGNYAM<br>DYWGQGTSVTVSS<br>(SEQ ID NO: 56) | ADX_Y1236.ZZ0-1-Vk<br>DIVMTQSQKFMSTSVGDRISITCKASQ<br>NVRTAVAWYQQKPGQSPKALIYLASNR<br>HTGVPARFSGSGSGTSYSLTISRMEAE<br>DAATYYCQQRSSYPLTFGAGTKLELK<br>(SEQ ID NO: 79) |
| ADX_Y1238.ZZ0-1 | ADX_Y1238.ZZ0-1-Vh<br>QVQLQQSGAELVRPGTSVKVSCKASG<br>YAFTNYLIEWVKQRPGQGLEWIGVIN<br>PGSGGTNYNEKFKGKATLTADKSSST<br>AYMQLSSLTSDDSAVYFCARSQLGRR<br>FDYWGQGTTLTVSS<br>SEQ ID NO: 57) | ADX_Y1238.ZZ0-1-Vk<br>DIVMTQSHKFMSTSVGDRVSITCKASQ<br>DVRTGVAWYQQKPGQSPKLLIYSASYR<br>NTGVPDRFTGSRSGTDFTFTISSVQAE<br>DLAVYYCQQHYSPPYTFGGGTKLEIK<br>(SEQ ID NO: 80) |
| ADX_Y1241.ZZ0-1 | ADX_Y1241.ZZ0-1-Vh<br>EFQLQQSGPELVKPGASVKMSCKASG<br>YTFTNYIIQWVKKQPGQGLEWIGYIN<br>PYSSETNYNEKFKGKATLTSDKSSST<br>AYMELSSLTSEDSAIYFCARDLIGNY<br>WGQGTTLTVSS<br>(SEQ ID NO: 58) | ADX_Y1241.ZZ0-1-Vk<br>DIVMTQSHKFMSTSVGDRVSITCKASQ<br>DVGTAVAWYQQKPGQSPKLLIYWASTR<br>HTGVPDRFTGSGSGTDFTLTISNVQSE<br>DLADYFCQQYSSYPLTFGAGTKLELK<br>(SEQ ID NO: 81) |
| ADX_Y1242.ZZ0-1 | ADX_Y1242.ZZ0-1-Vh<br>EFQLQQSGPELVKPGASVKMSCKASG<br>YSFTSYVMHWVKQKPGQALEWIGYIN<br>PSNDGSEYNERFKGKATLTSDKSSTT<br>AYMELSSLTSEDSAVYYCARWAPYPF<br>AYWGQGTLVTVSA<br>(SEQ ID NO: 59) | ADX_Y1242.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPYTFGGGTKLEIK<br>(SEQ ID NO: 82) |

TABLE 8-continued

Mouse anti-human-CD40 variable heavy and light sequences

| ID | VH Sequence | VL Sequence |
| --- | --- | --- |
| ADX_Y1249.ZZ0-1 | ADX_Y1249.ZZ0-1-Vh<br>QVQLQQSGAELARPGASVKMSCKASG<br>YTFTSYTMHWVKQRPGQGLEWIGYID<br>PSSHYTNYNQKFKGTATLTADKSSNT<br>AYMQLSSLTSEDSAVYYCARDYRYAY<br>WYFDVWGAGTTLTVSS<br>(SEQ ID NO: 60) | ADX_Y1249.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 83) |
| ADX_Y1256.ZZ0-1 | ADX_Y1256.ZZ0-1-Vh<br>QVQLQQSGAELAKPGSSVKMSCKASG<br>YAFTSYWMHWVKQRPGQGLEWIGYIN<br>PTTGYSAYNQKFKDKATLTADKSSST<br>AYLQLTSLTSEDSAVYFCSRWGLPPF<br>AYWGQGTLVTVSA<br>(SEQ ID NO: 61) | ADX_Y1256.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 84) |
| ADX_Y1257.ZZ0-1 | ADX_Y1257.ZZ0-1-Vh<br>QVQLQQSGAELAKPGSSVKMSCKASG<br>YAFTSYWMHWVKQRPGQGLEWIGYIN<br>PTTGYSAYNQKFKAKTTLTADKSSST<br>AYMQLTSLTFEDSAVYFCSRWGLPPF<br>AYWGQGTLVTVSA<br>(SEQ ID NO: 62) | ADX_Y1257.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 85) |
| ADX_Y1258.ZZ0-1 | ADX_Y1258.ZZ0-1-Vh<br>QVQLQQSGAELAKPGSSVKMSCKASG<br>YAFTSYWMHWIKQRPGQGLEWIGFIN<br>PTTGYSEYNQKFKDKATLTADKSSST<br>AYMQLNSLTSEDSAVYFCARWGLPPF<br>AYWGQGTLVTVSA<br>(SEQ ID NO: 63) | ADX_Y1258.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 86) |
| ADX_Y1259.ZZ0-1 | ADX_Y1259.ZZ0-1-Vh<br>QVQLQQSGAELAKPGASVKMSCKTSG<br>YSFTSYWMHWIKQRPGQGLEWIGFIN<br>PTTGYTEYNQKFKDKATLTADKSSST<br>AYMQLSSLSSEDSAVYYCSRWGLPPF<br>AYWGQGTLVTVSA<br>(SEQ ID NO: 64) | ADX_Y1259.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 87) |
| ADX_Y1260.ZZ0-1 | ADX_Y1260.ZZ0-1-Vh<br>QVQLQQSGAELTKPGASVKMSCKASG<br>YSFTSYWMHWVKQRPGQGLEWIGSIN<br>PSTGYTEDNQKFKDKATLTADKSSTT<br>AYMQLSSLTSEDSAVYYCARWGLPPF<br>AYWGQGTLVTVSA<br>(SEQ ID NO: 65) | ADX_Y1260.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 88) |
| ADX_Y1261.ZZ0-1 | ADX_Y1261.ZZ0-1-Vh<br>QVQLQQSGAERAKPGASVKMSCKASG<br>YSFTSYWMHWIKQRPGQGLEWIGFIN<br>PNTGHTDYNQKFKDKATLTADKSSST<br>AYMQLSSLTSEDSAVYFCSRWGLPPF<br>AYWGQGTLVTVSA<br>(SEQ ID NO: 66) | ADX_Y1261.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 89) |
| ADX_Y1262.ZZ0-1 | ADX_Y1262.ZZ0-1-Vh<br>QVQLQQSGAELAKPGSSVKMSCKASG<br>YAFTSYWMHWVKQRPGQGLEWIGYIN<br>PTTGYSAYNQKFKDKATLTADKSSST<br>AYMQLNSLTSEDSAVYYCARWDPRPF<br>AYWGQGTLVTVSA<br>(SEQ ID NO: 67) | ADX_Y1262.ZZ0-1-Vk<br>DIVMTQSHKFMSTSVGDRVSITCKASQ<br>DVSTAVAWYQQKPGQSPKLLIYSASYR<br>YTGVPDRFTGSGYGTDFTFTISSVQAE<br>DLAVYYCQQHYSTPWTFGGGTKLEIK<br>(SEQ ID NO: 90) |
| ADX_Y1263.ZZ0-1 | ADX_Y1263.ZZ0-1-Vh<br>QVQLQQSGAELAKPGTSVKMSCKASG<br>YSFTSYWVHWVKERPGQGLEWIGHTN<br>PNTGYTEYNQKFKDKATLTVDRSSST<br>AYMQLNSLTSEDSAVYYCARWDPRPF<br>AYWGQGTLVTVSA<br>(SEQ ID NO: 68) | ADX_Y1263.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 91) |

TABLE 8-continued

Mouse anti-human-CD40 variable heavy and light sequences

| ID | VH Sequence | VLSequence |
|---|---|---|
| ADX_Y1264.ZZ0-1 | ADX_Y1264.ZZ0-1-Vh<br>EVQLQQSGTVLARPGASVKMSCRASG<br>YSFSSYWMHWVKQRPGQGLEWIGSIN<br>PGNSDAFYNQQFKGKAKLTAVTSAST<br>AYMELSSLTNEDSAVYYCTRWGLPPF<br>AYWGQGTLVTVSA<br>(SEQ ID NO: 69) | ADX_Y1264.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCHQYSTPWTFGGGTKLEIK<br>(SEQ ID NO: 92) |
| ADX_Y1265.ZZ0-1 | ADX_Y1265.ZZ0-1-Vh<br>EVQLQQSGTVLAGPGASVKMSCKASG<br>YSFTSYWMHWVKQRPGQDLEWIGTIN<br>PGKGDSNYNQKFKGKAKLTAVTSAST<br>AYMELSSLTNEDSAVYYCTRWGLPPF<br>AYWGQGTLVTVSA<br>(SEQ ID NO: 70) | ADX_Y1265.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 93) |
| ADX_Y1266.ZZ0-1 | ADX_Y1266.ZZ0-1-Vh<br>QVQLQQPGAELVKPGASVRLSCKASG<br>YSFTSYWMHWVKQRPGQGLEWIGQIN<br>PSNGRTQYNEKFKSMATLTVDKSSST<br>AYIQLSSLTSEDSAVYYCARWGLPQPF<br>AYWGQGTLVTVSA<br>(SEQ ID NO: 71) | ADX_Y1266.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 94) |
| ADX_Y1267.ZZ0-1 | ADX_Y1267.ZZ0-1-Vh<br>QVQLQQPGAELVKPGASVRLSCEASG<br>YSFTSYWMHWVKQRPGQGLEWIGQIN<br>PSNGRTQYNEKFKSMATLTVDKSSST<br>AYIQLNSLTSEDSAVYYCARWGLPQPF<br>AYWGQGTLVTVSA<br>(SEQ ID NO: 72) | ADX_Y1267.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCLQHYTTPWTFGGGTKLEIK<br>(SEQ ID NO: 95) |
| ADX_Y1268.ZZ0-1 | ADX_Y1268.ZZ0-1-Vh<br>QVQLQQPGAELVKPGASVRLSCKASG<br>YAFTSYWMHWVKQRPGQGLEWIGQIN<br>PSNGRSQYNEKFKTMATLTVDKSSST<br>AYIQLSSLTSEDSAVYYCARWGLPQPF<br>AYWGQGTLVTVSA<br>(SEQ ID NO: 73) | ADX_Y1268.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 96) |
| ADX_Y1269.ZZ0-1 | ADX_Y1269.ZZ0-1-Vh<br>QVQLQQSGAELPRPGASVKMSCKASG<br>YTFTDYTVHWVKQRPGQGLEWIGYIN<br>PSSSYTSYDQKFKDKATVTADKSSST<br>AYMQLSSLTSEDSAVYYCARRTMYWY<br>FDIWGAGTTVTVSS<br>(SEQ ID NO: 74) | ADX_Y1269.ZZ0-1-Vk<br>DIVMTQSHKFMSTSVGDRVSITCKASQ<br>DVSPNVAWYQQKPGQSPKLLIYSTSYR<br>YTGVPDRFTGSRSGTDFTFTISSVQAE<br>DLAIYYCQQHYSTPLTFGAGTKLELK<br>(SEQ ID NO: 97) |
| ADX_Y1297.ZZ0-1 | ADX_Y1297.ZZ0-1-Vh<br>QVQLQQSGAELVKPGASVKLSCKASG<br>YTFTSYWMHWVKQRPGQGLEWIGEID<br>PSDSYTNYNQNFKGKATLTVDKSSST<br>AYMQLSSLTSEDSAVYYCARETYYYG<br>SRFPYWGQGTLVTVSA<br>(SEQ ID NO: 75) | ADX_Y1297.ZZ0-1-Vk<br>DIVMTQSHKFMSTSVGDRVSVTCKASQ<br>NVRINVAWYQQKPGQSPKALIYSASYR<br>YSGVPDRFTGSGSGTDFTLTITNVQSE<br>DLAEYFCQQYNTYPLTFGAGTKLELK<br>(SEQ ID NO: 98) |

The CD40 kinetic and affinity data for human-CD40 monomer binding to mouse anti-human CD40 antibodies captured on a protein A sensor chip surface were assessed by SPR. The data are shown in Table 9. The data shown are for a single concentration of CD40 analyte (1 μM) and are therefore reported as apparent (app) values.

TABLE 9

SPR kinetic/affinity data

| Antibody | $ka_{,app}$ (1/Ms) | $kd_{,app}$ (1/s) | $KD_{app}$ (M) |
|---|---|---|---|
| ADX_Y1072.ZZ0-1 | 7.7E+04 | 9.2E-03 | 1.2E-07 |
| ADX_Y1238.ZZ0-1 | 5.5E+04 | 1.2E-04 | 2.2E-09 |

TABLE 9-continued

SPR kinetic/affinity data

| Antibody | $ka_{,app}$ (1/Ms) | $kd_{,app}$ (1/s) | $KD_{app}$ (M) |
|---|---|---|---|
| ADX_Y1258.ZZO-1 | 1.7E+04 | 1.3E-04 | 7.9E-09 |
| ADX_Y1260.ZZO-1 | 5.2E+04 | 2.1E-04 | 4.0E-09 |
| ADX_Y1262.ZZO-1 | 3.7E+05 | 2.5E-03 | 6.6E-09 |
| ADX_Y1264.ZZO-1 | 1.4E+04 | 2.3E-04 | 1.7E-08 |
| ADX_Y1267.ZZO-1 | 3.7E+05 | 4.1E-04 | 1.1E-09 |
| ADX_Y1268.ZZO-1 | 3.2E+05 | 4.6E-04 | 1.4E-09 |

Based on the SPR data and sequence data, three antibodies, ADX_Y1258.ZZ0-1, ADX_Y1262.ZZ0-1, and ADX_Y1268.ZZ0-1, were selected for humanization.

Example 2: Humanization and Selection of Humanized Variants of Y12XX

Humanization background/procedure is as discussed in section "II. Engineered and Modified Antibodies" in WO2017004006, which is incorporated herein by reference in its entirety. Based on this analysis, nine (9) humanized Vh sequences (Vh-hz1, Vh-hz2, Vh-hz3, Vh-hz4, Vh-hz5, Vh-hz6, Vh-hz9, Vh-hz10, and Vh-hz11) and three (3) humanized Vκ sequences (Vk-hz1, Vk-hz2, and Vk-hz3), were selected for testing. In addition, five (5) humanized Vh sequences (Vh-hz7, Vh-hz8, Vh-hz12, Vh-hz13, and Vh-hz14) were designed to contain mutations intended to reduce chemical liability risk designed. The mutations include D100Q (Y1262_IGHV1.6908-D100Q) and P101A (Y1262_IGHV1.6908-P101A) mutations to mitigate potential hydrolysis risk in Y1262_IGHV1.6908. The mutations also include N55Q (Y1268_IGHV1.6908-N55Q), G56A (Y1268_IGHV1.6908-G56A), and the S54T-N55T double mutation (Y1268_IGHV1.6908-S54T-N55T) to mitigate potential deamidation risk in Y1268_IGHV1.6908. The S54T-N55T double mutation was designed based on the corresponding amino acid residues found at these positions in ADX_Y1262.ZZ0-1-Vh. See Table 10.

The sequences for these variants are shown in Table 10.

TABLE 10

| ID | Variable Hz # | SEQ ID NO: | Sequence |
|---|---|---|---|
| Y1258-Vh | Vh-C1 | 99 | QVQLQQSGAELAKPGSSVKMSCKASGYAFTSYWMHWIKQRPGQGLEWIGFINPTTGYSEYNQKFKDKATLTADKSSSTAYMQLNSLTSEDSAVYFCARWGLPPFAYWGQGTLVTVSA |
| Y1258_IGHV1.6908-Vh | Vh-hz1 | 100 | QVQLVQSGAEVKKPGSSVKVSCKASGYAFTSYWMHWVRQAPGQGLEWMGFINPTTGYSEYNQKFKDRVTITADKSTSTAYMELSSLRSEDTAVYYCARWGLPPFAYWGQGTLVTVSS |
| Y1258_IGHV1.6908_A40R-Vh | Vh-hz2 | 101 | QVQLVQSGAEVKKPGSSVKVSCKASGYAFTSYWMHWVRQRPGQGLEWMGFINPTTGYSEYNQKFKDRVTITADKSTSTAYMELSSLRSEDTAVYYCARWGLPPFAYWGQGTLVTVSS |
| Y1258_IGHV1.6908_A40R-M48I-S84N-Vh | Vh-hz3 | 102 | QVQLVQSGAEVKKPGSSVKVSCKASGYAFTSYWMHWVRQRPGQGLEWIGFINPTTGYSEYNQKFKDRVTITADKSTSTAYMELNSLRSEDTAVYYCARWGLPPFAYWGQGTLVTVSS |
| Y1262-Vh | Vh-C2 | 103 | QVQLQQSGAELAKPGSSVKMSCKASGYAFTSYWMHWVKQRPGQGLEWIGYINPTTGYSAYNQKFKDKATLTADKSSSTAYMQLNSLTSEDSAVYYCARWDPRPFAYWGQGTLVTVSA |
| Y1262_IGHV1.6908-Vh | Vh-hz4 | 104 | QVQLVQSGAEVKKPGSSVKVSCKASGYAFTSYWMHWVRQAPGQGLEWMGYINPTTGYSAYNQKFKDKATLTADKSTSTAYMELSSLRSEDTAVYYCARWDPRPFAYWGQGTLVTVSS |
| Y1262_IGHV1.6908_A40R-Vh | Vh-hz5 | 105 | QVQLVQSGAEVKKPGSSVKVSCKASGYAFTSYWMHWVRQRPGQGLEWMGYINPTTGYSAYNQKFKDKATLTADKSTSTAYMELSSLRSEDTAVYYCARWDPRPFAYWGQGTLVTVSS |
| Y1262_IGHV1.6908_A40R-M48I-S84N-Vh | Vh-hz6 | 106 | QVQLVQSGAEVKKPGSSVKVSCKASGYAFTSYWMHWVRQRPGQGLEWIGYINPTTGYSAYNQKFKDKATLTADKSTSTAYMELNSLRSEDTAVYYCARWDPRPFAYWGQGTLVTVSS |
| Y1262_IGHV1.6908-D100Q-Vh | Vh-hz7 | 107 | QVQLVQSGAEVKKPGSSVKVSCKASGYAFTSYWMHWVRQAPGQGLEWMGYINPTTGYSAYNQKFKDKATLTADKSTSTAYMELSSLRSEDTAVYYCARWQPRPFAYWGQGTLVTVSS |
| Y1262_IGHV1.6908-P101A-Vh | Vh-hz8 | 108 | QVQLVQSGAEVKKPGSSVKVSCKASGYAFTSYWMHWVRQAPGQGLEWMGYINPTTGYSAYNQKFKDKATLTADKSTSTAYMELSSLRSEDTAVYYCARWDARPFAYWGQGTLVTVSS |
| Y1268-Vh | Vh-C3 | 109 | QVQLQQPGAELVKPGASVRLSCKASGYAFTSYWMHWVKQRPGQGLEWIGQINPSNGRSQYNEKFKTMATLTVDKSSSTAYIQLSSLTSEDSAVYYCARWGLQPFAYWGQGTLVTVSA |
| Y1268_IGHV1.6908-Vh | Vh-hz9 | 110 | QVQLVQSGAEVKKPGSSVKVSCKASGYAFTSYWMHWVRQAPGQGLEWMGQINPSNGRSQYNEKFKTRVTITADKSTSTAYMELSSLRSEDTAVYYCARWGLQPFAYWGQGTLVTVSS |

TABLE 10-continued

| ID | Variable Hz # | SEQ ID NO: | Sequence |
|---|---|---|---|
| Y1268_IGHV1.6908_A40R-Vh | Vh-hz10 | 111 | QVQLVQSGAEVKKPGSSVKVSCKASGYAFT<u>SYWMH</u>WV RQRPGQGLEWMG<u>QINPSNGRSQYNEKFK</u>TRVTITADK STSTAYMELSSLRSEDTAVYYCAR<u>WGLQPFAY</u>WGQGT LVTVSS |
| Y1268_IGHV1.6908_A40R-M48I-Vh | Vh-hz11 | 112 | QVQLVQSGAEVKKPGSSVKVSCKASGYAFT<u>SYWMH</u>WV RQRPGQGLEWIG<u>QINPSNGRSQYNEKFK</u>TRVTITADK STSTAYMELSSLRSEDTAVYYCAR<u>WGLQPFAY</u>WGQGT LVTVSS |
| Y1268_IGHV1.6908-N55Q-Vh | Vh-hz12 | 13 | QVQLVQSGAEVKKPGSSVKVSCKASGYAFT<u>SYWMH</u>WV RQAPGQGLEWMG<u>QINPSQGRSQYNEKFK</u>TRVTITADK STSTAYMELSSLRSEDTAVYYCAR<u>WGLQPFAY</u>WGQGT LVTVSS |
| Y1268_IGHV1.6908-G56A-Vh | Vh-hz13 | 113 | QVQLVQSGAEVKKPGSSVKVSCKASGYAFT<u>SYWMH</u>WV RQAPGQGLEWMG<u>QINPSNARSQYNEKFK</u>TRVTITADK STSTAYMELSSLRSEDTAVYYCAR<u>WGLQPFAY</u>WGQGT LVTVSS |
| Y1268_IGHV1.6908-S54T-N55T-Vh | Vh-hz14 | 4 | QVQLVQSGAEVKKPGSSVKVSCKASGYAFT<u>SYWMH</u>WV RQAPGQGLEWMG<u>QINPTTGRSQYNEKFK</u>TRVTITADK STSTAYMELSSLRSEDTAVYYCAR<u>WGLQPFAY</u>WGQGT LVTVSS |
| Y1258-Vk | Vk-C1 | 114 | DIVMTQSHKFMSTSVGDRVSITCKASQDVSTAVAWYQ QKPGQSPKLLIYSASYRYTGVPDRFTGSGSGTDFTFT ISSVQAEDLAVYYCQQHYSTPWTFGGGTKLEIK |
| Y1262-Vk | Vk-C2 | 115 | DIVMTQSHKFMSTSVGDRVSITCKASQDVSTAVAWYQ QKPGQSPKLLIYSASYRYTGVPDRFTGSGYGTDFTFT ISSVQAEDLAVYYCQQHYSTPWTFGGGTKLEIK |
| Y1258_IGKV1.3301-Vk | Vk-hz1 | 116 | DIQMTQSPSSLSASVGDRVTITCKASQDVSTAVAWYQ QKPGKAPKLLIYSASYRYTGVPSRFSGSGSGTDFTFT ISSLQPEDIATYYCQQHYSTPWTFGGGTKVEIK |
| Y1258-IGKV1.3902-Vk | Vk-hz2 | 10 | DIQMTQSPSFLSASVGDRVTITCKASQDVSTAVAWYQ QKPGKAPKLLIYSASYRYTGVPSRFSGSGSGTDFTLT ISSLQPEDFATYYCQQHYSTPWTFGGGTKVEIK |
| Y1258-IGKV3.1501-Vk | Vk-hz3 | 16 | EIVMTQSPATLSVSPGERATLSCKASQDVSTAVAWYQ QKPGQAPRLLIYSASYRYTGIPARFSGSGSGTEFTLT ISSLQSEDFAVYYCQQHYSTPWTFGGGTKVEIK |

Table 10 provides the heavy and variable light domain sequences used for construction of humanized antibodies, as well as chimeric antibody controls, for CD40 binding analyses using BIAcore™ surface plasmon resonance (SPR), as well as Octet BLI titer analyses (discussed below).

Vh sequences were formatted with IgG1-P238K isotype (CH1-IgG1-P238K; SEQ ID NO:25). Vκ sequences were formatted as a full light chain with a common CL sequence (amino acids 108-214 of SEQ ID No: 11). In Table 11, "Y1258" and "Y1262" refer to chimeric molecules containing mouse variable regions and human constant regions. The various different combinations of the humanized HC constructs and LC constructs, as well as the chimeric Y1258 and Y1262 molecules were expressed as 3 milliliter (ml) supernatants for titer analysis and CD40 binding analysis. The family of molecules was collectively identified with an "Y12XX" prefix, followed by a "hz #" suffix to uniquely identify different heavy chain/light chain pairs.

Titer analysis was performed using Biolayer Interferometry (BLI) on an Octet RED instrument (Fortebio) by capturing antibodies from supernatant using protein A sensor tips and measuring capture response with respect to a standard curve obtained using a control antibody sample. SPR data were obtained by capturing antibodies on a protein A surface and testing the binding of 500 nM and 50 nM injections of human-CD40 analyte, using a BIAcore™ T200 instrument (GE Healthcare). The kinetic data for the two concentrations of hCD40-monomer were fit to a 1:1 Langmuir model, to yield estimates of the kinetic and affinity values for these interactions, and for comparison of the different molecules.

The Octet titer and BIAcore™ SPR CD40 binding data are provided in Table 11. In addition to testing supernatant ("sup") samples, purified chimeric Y1258, Y1262 and Y1268 antibodies containing human wild-type IgG1f isotype (<u>ASTKGPSVFPLAPSSKSTSGGTAALGCLVKDYFPEPVTVSWNSGALTS</u>

<u>GVHTFPAVLQSSGLYSLSSVVTVPSSSLGTQTYICNVNHKPSNTKVDKR</u>

-continued

VEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKL

TVDKSRWQQGNVFSCSVMHEALHNHYTQKSLSLSPGK;

SEQ ID NO: 117)

were tested by SPR as controls; these are named "Y1258-hIgG1f", "Y1632-hIgG1f" and "Y1268-hIgG1f" in Table 11, and the Vh and Vk chains are denoted as "Chim-P."

For a given heavy chain construct, the titer is generally highest when paired with light chains containing Vk-hz3 (SEQ ID NO:18), lower for heavy chains paired with Vk-hz2 (SEQ ID NO:10), and the lowest for heavy chains paired with Vk-hz1 (SEQ ID NO:116) containing light chains.

The SPR analysis data show that the antibodies bound with variable affinity to CD40, with KD values ranging from greater than 1 E-07 to less than 1 E-09. For some antibodies, the affinity was too strong to accurately determine with confidence in this assay, because the dissociation rate was too slow to measure. These values, which are italicized in the table, are beyond the limit of accurate quantitation in this assay.

TABLE 11

Octet titer and BIAcore™ SPR CD40 binding data

| Antibody ID | Vh | Vk | Sample | Titer (µg/ml) | ka (1/Ms) | kd (1/s) | KD (M) |
|---|---|---|---|---|---|---|---|
| Y1258-hIgG1f | Chim-P | Chim-P | purified | n/a | 5.8E+04 | *5.9E-07* | *1.0E-11* |
| Y1258 | Vh-C1 | Vk-C1 | sup | 54.2 | 5.6E+04 | *3.8E-06* | *6.7E-11* |
| Y12XX-hz1 | Vh-hz1 | Vk-hz1 | sup | 3.8 | 1.5E+04 | 1.6E-05 | 1.1E-09 |
| Y12XX-hz15 | Vh-hz1 | Vk-hz2 | sup | 34.6 | 1.6E+04 | 1.3E-04 | 8.0E-09 |
| Y12XX-hz29 | Vh-hz1 | Vk-hz3 | sup | 56.7 | 3.7E+04 | *2.6E-06* | *6.9E-11* |
| Y12XX-hz2 | Vh-hz2 | Vk-hz1 | sup | 4.5 | 1.7E+04 | 7.1E-05 | 4.1E-09 |
| Y12XX-hz16 | Vh-hz2 | Vk-hz2 | sup | 58.6 | 2.0E+05 | 6.4E-04 | 3.2E-09 |
| Y12XX-hz30 | Vh-hz2 | Vk-hz3 | sup | 82.6 | 4.1E+04 | *7.3E-07* | *1.8E-11* |
| Y12XX-hz3 | Vh-hz3 | Vk-hz1 | sup | 6.4 | 1.5E+04 | 6.7E-05 | 4.5E-09 |
| Y12XX-hz17 | Vh-hz3 | Vk-hz2 | sup | 50.7 | 3.7E+05 | 7.7E-02 | 2.1E-07 |
| Y12XX-hz31 | Vh-hz3 | Vk-hz3 | sup | 93.9 | 4.1E+04 | *2.9E-07* | *7.0E-12* |
| Y1262-hIgG1f | Chim-P | Chim-P | purified | n/a | 4.8E+05 | 5.5E-03 | 1.2E-08 |
| Y1262 | Chim | Chim | sup | 92.2 | 3.5E+05 | 2.8E-03 | 8.0E-09 |
| Y12XX-hz4 | Vh-hz4 | Vk-hz1 | sup | 4.7 | 4.6E+05 | 2.2E-03 | 4.7E-09 |
| Y12XX-hz18 | Vh-hz4 | Vk-hz2 | sup | 73.6 | 3.5E+05 | 2.4E-03 | 7.1E-09 |
| Y12XX-hz32 | Vh-hz4 | Vk-hz3 | sup | 104.3 | 2.9E+05 | 3.0E-03 | 1.0E-08 |
| Y12XX-hz5 | Vh-hz5 | Vk-hz1 | sup | 4.5 | 3.5E+05 | 2.5E-03 | 7.2E-09 |
| Y12XX-hz19 | Vh-hz5 | Vk-hz2 | sup | 56.7 | 3.8E+05 | 2.3E-03 | 6.2E-09 |
| Y12XX-hz33 | Vh-hz5 | Vk-hz3 | sup | 85.5 | 2.9E+05 | 3.3E-03 | 1.1E-08 |
| Y12XX-hz6 | Vh-hz6 | Vk-hz1 | sup | 6.7 | 3.8E+05 | 2.4E-03 | 6.4E-09 |
| Y12XX-hz20 | Vh-hz6 | Vk-hz2 | sup | 50.3 | 3.1E+05 | 2.5E-03 | 8.2E-09 |
| Y12XX-hz34 | Vh-hz6 | Vk-hz3 | sup | 93.7 | 3.7E+05 | 2.8E-03 | 7.6E-09 |
| Y12XX-hz8 | Vh-hz8 | Vk-hz1 | sup | 11.2 | 7.2E+05 | 1.5E-01 | 2.1E-07 |
| Y12XX-hz22 | Vh-hz8 | Vk-hz2 | sup | 49.1 | 3.7E+05 | 7.9E-02 | 2.1E-07 |
| Y12XX-hz36 | Vh-hz8 | Vk-hz3 | sup | 136.7 | 3.9E+05 | 1.0E-01 | 2.5E-07 |
| Y1268-hIgG1f | Chim-P | Chim-P | purified | n/a | 4.0E+05 | 1.3E-03 | 3.2E-09 |
| Y12XX-hz9 | Vh-hz9 | Vk-hz1 | sup | 5.1 | 2.0E+05 | 8.9E-04 | 4.6E-09 |
| Y12XX-hz23 | Vh-hz9 | Vk-hz2 | sup | 59.4 | 2.0E+05 | 6.4E-04 | 3.2E-09 |
| Y12XX-hz37 | Vh-hz9 | Vk-hz3 | sup | 138.4 | 2.6E+05 | 8.4E-04 | 3.3E-09 |
| Y12XX-hz10 | Vh-hz10 | Vk-hz1 | sup | 8.6 | 2.0E+05 | 7.3E-04 | 3.6E-09 |
| Y12XX-hz24 | Vh-hz10 | Vk-hz2 | sup | 48.1 | 1.9E+05 | 8.2E-04 | 4.4E-09 |
| Y12XX-hz38 | Vh-hz10 | Vk-hz3 | sup | 185.5 | 2.5E+05 | 8.8E-04 | 3.6E-09 |
| Y12XX-hz11 | Vh-hz11 | Vk-hz1 | sup | 7.5 | 1.8E+05 | 8.8E-04 | 5.0E-09 |
| Y12XX-hz25 | Vh-hz11 | Vk-hz2 | sup | 55.4 | 1.9E+05 | 6.4E-04 | 3.4E-09 |
| Y12XX-hz39 | Vh-hz11 | Vk-hz3 | sup | 134.2 | 2.4E+05 | 8.4E-04 | 3.5E-09 |
| Y12XX-hz12 | Vh-hz12 | Vk-hz1 | sup | 2.7 | 1.7E+05 | 1.4E-03 | 8.3E-09 |
| Y12XX-hz26 | Vh-hz12 | Vk-hz2 | sup | 36.8 | 1.6E+05 | 1.2E-03 | 7.5E-09 |
| Y12XX-hz40 | Vh-hz12 | Vk-hz3 | sup | 99.8 | 2.4E+05 | 1.1E-03 | 4.7E-09 |
| Y12XX-hz13 | Vh-hz13 | Vk-hz1 | sup | 3.0 | 2.1E+05 | 8.3E-04 | 3.9E-09 |
| Y12XX-hz27 | Vh-hz13 | Vk-hz2 | sup | 49.5 | 1.9E+05 | 8.8E-04 | 4.7E-09 |
| Y12XX-hz41 | Vh-hz13 | Vk-hz3 | sup | 52.7 | 2.5E+05 | 9.4E-04 | 3.8E-09 |
| Y12XX-hz14 | Vh-hz14 | Vk-hz1 | sup | 5.0 | 1.7E+05 | 8.3E-04 | 5.0E-09 |
| Y12XX-hz28 | Vh-hz14 | Vk-hz2 | sup | 70.1 | 1.8E+05 | 6.2E-04 | 3.5E-09 |
| Y12XX-hz42 | Vh-hz14 | Vk-hz3 | sup | 100.0 | 2.4E+05 | 8.3E-04 | 3.5E-09 |

Based on the sequences, titer, and SPR binding data, antibodies were selected for larger scale expression, purification, and further characterization. SPR analysis using purified antibodies was performed by capturing antibodies on a protein A surface, with binding of a 500-3.9 nM (2:1) dilution series of human-CD40 monomer, at either 25° C. or 37° C. in PBS-T pH 7.1 buffer; the titration data was fit to a 1:1 Langmuir model. The data is provided in Table 12.

TABLE 12

SPR kinetic/affinity data

| Ligand | Sample | 25° C. | | | 37° C. | | |
|---|---|---|---|---|---|---|---|
| | | ka (1/Ms) | kd (1/s) | KD (nM) | ka (1/Ms) | kd (1/s) | KD (nM) |
| Y12XX-hz28 | hCD40 | 2.2E+05 | 6.9E−04 | 3.1 | 4.4E+05 | 3.7E−03 | 8.5 |
| Y12XX-hz40 | hCD40 | 2.9E+05 | 1.3E−03 | 4.4 | 5.2E+05 | 5.7E−03 | 10.9 |
| Y12XX-hz42 | hCD40 | 3.1E+05 | 7.3E−04 | 2.3 | 6.3E+05 | 3.4E−03 | 5.5 |
| Antibody B | | 6.1E+04 | 2.3E−03 | 37 | | | |

These data show that the selected Y12XX antibodies bind with high affinity and KD values in the range of KD=1 E-9 M at 25° C. The binding is compared to that of another anti-CD40 antibody, antibody BI-mAb-B (U.S. Pat. No. 9,090,696, heavy chain sequence SEQ ID NO: 32 and light chain sequence SEQ ID NO: 31; referred to herein as "Antibody B" and "BI-LALA"). As shown by the data in Table 12, Antibody B binds to CD40 with much lower affinity than the humanized Y12XX molecules.

All three humanized versions of the Y12XX antibody were potent antagonists of B cell proliferation stimulated with CD40L-IZ trimeric agonist. See Table 13.

TABLE 13

Inhibition of B cell proliferation induced by soluble CD40L trimer

| | Average (IC50 ng/ml) | Standard Deviation (STDEV) | n donors |
|---|---|---|---|
| Antibody B | 9.4 | 3.9 | 6 |
| Y12XX-hz28-P238K | 6.7 | 3.6 | 8 |
| Y12XX-hz40-P238K | 6.0 | 4.7 | 2 |
| Y12XX-hz42-P238K | 12.1 | 2.3 | 2 |

Y12XX-hz28-P238K was also a potent antagonist of B cell proliferation stimulated with cellular CD40L from CD40L-expressing CHO cells. See Table 14.

TABLE 14

Potency for inhibition of CD40L expressing CHO cells stimulation of B cell proliferation

| | Potency (IC50 ng/ml of % inhibition) | Standard deviation | n donors |
|---|---|---|---|
| Antibody B | 62% * | 25% | 6 |
| Y12XX-hz28-P238K | 38.1 | 9.8 | 8 |

* % inhibition at highest dose tested (1-3 µg/ml)

The data for the humanized Y12XX antibodies is compared to that of Antibody B, which showed potent inhibition of B cell proliferation driven by soluble CD40L signals, but was much less effective at inhibition of B cell proliferation driven by cellular CD40L (CHO cells overexpressing CD40L). In contrast, humanized Y12XX antibodies exhibited only a <10 fold shift in the potency for inhibition of cell surface CD40L stimulation, providing more robust blockade of B cell responses to CD40L.

Humanized Y12XX antibodies were formatted with IgG1-P238K isotype (CH1-IgG1-P238K; SEQ ID NO: 25) to reduce the binding affinity for FcγRs and reduce FcγR-mediated signaling. FcγR binding for a representative humanized Y12XX antibody with this IgG1-P238K isotype (Y12XX-hz28-IgG1-P238K) was compared to the binding of a control antibody formatted with a wild type IgG1 isotype (control-IgG1) as well as Antibody B which has an IgG1 isotype containing the mutations L234A-L235A. These L234A-L235A mutations are also introduced to reduce FcγR binding.

FcγR binding SPR studies were performed by capturing antibodies on a protein A sensor chip surface and binding purified His-tagged human FcγRs as analyte. hCD64 binding consisted of a titration of 10 µM-1.5 nM hCD64 (2:1 dilution series), while data for the low affinity FcγRs hCD32a-H131, hCD32a-R131, hCD32b, hCD16a-V158, and hCD16a-F158 consisted of a titration of 10 uM-13.7 nM FcγR protein.

Figure 1B:
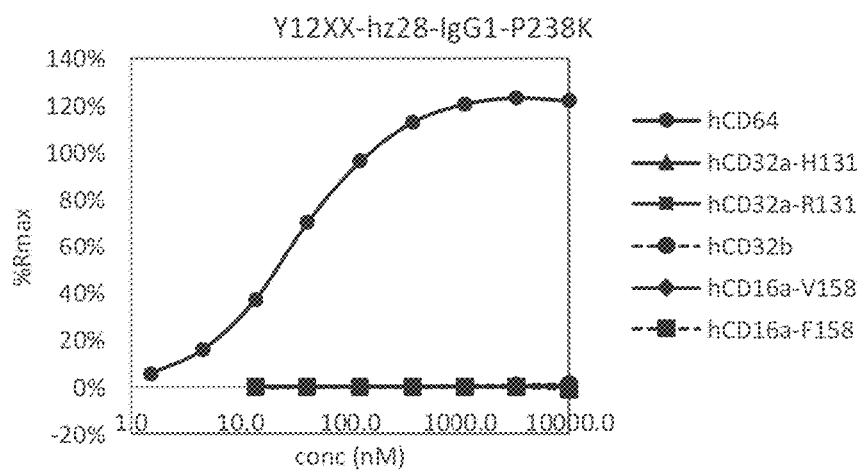
Figure 1C:
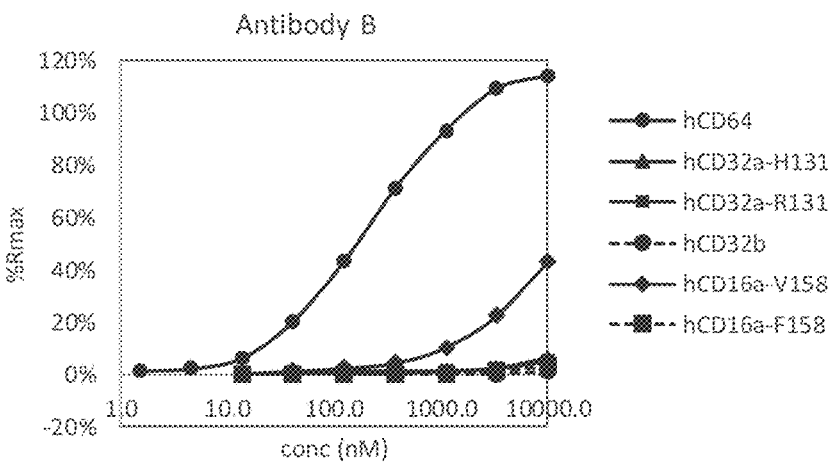

The control-IgG1 antibody demonstrated binding to all of the FcγRs tested. See FIG. 1A. Compared to wild type, the Y12XX-hz28-IgG1-P238K antibody demonstrated 125-fold weaker binding to hCD64, and demonstrated no detectable binding to any of the low affinity FcγRs hCD32a-H131, hCD32a-R131, hCD32b, hCD16a-V158 and hCD16a-F158 tested. See FIG. 1B. Antibody B also demonstrated weaker hCD64 binding than wild type IgG1, but also demonstrated appreciable binding to hCD16a-V158 (KD=7 µM) and some weak binding to hCD32a-H131 and hCD32a-R131. See FIG. 1C. The KD values are provided in FIG. 1D.

Humanized versions of the antibody Y12XX with P238K mutation in the Fc region were further tested for any agonist activity. Monocyte derived immature dendritic cells (iDC) are very sensitive to CD40 activation, increasing cytokine production (IL-6) and upregulating surface markers of activation (CD86 and CD54) upon CD40 stimulation. Therefore, the most promising humanized Y12XX antibodies were tested to assess their ability to stimulate iDC. The ability of CD40 antibodies to agonize CD40 can be enhanced by clustering or cross-linking binding of the Fc portions of the molecule to cell surface FcγR. Addition of CHO cells highly over-expressing CD32a, the low affinity FcγR, were used to evaluate the potential for FcγR mediated clustering/cross-link. The ratio of CHO cells to iDCs was 1:6 in these experiments, representing a potentially exaggerated level of clustering/cross-linking. BMS-986090 and 2141 were used as positive controls. BMS-986090 is an anti-CD40 antagonist domain antibody fused to IgG4 Fc (see SEQ ID NO: 1287 in WO 2012/145673). 2141 (mAb 134-2141) is a partial CD40 agonist (see Robert Vonderheide et al., 2007, *J. Clin. Oncol.* 25(7): 876-883). L6-IgG4 is a fusion protein with no CD40 binding capability, and served as a negative control.

Figure 2A:
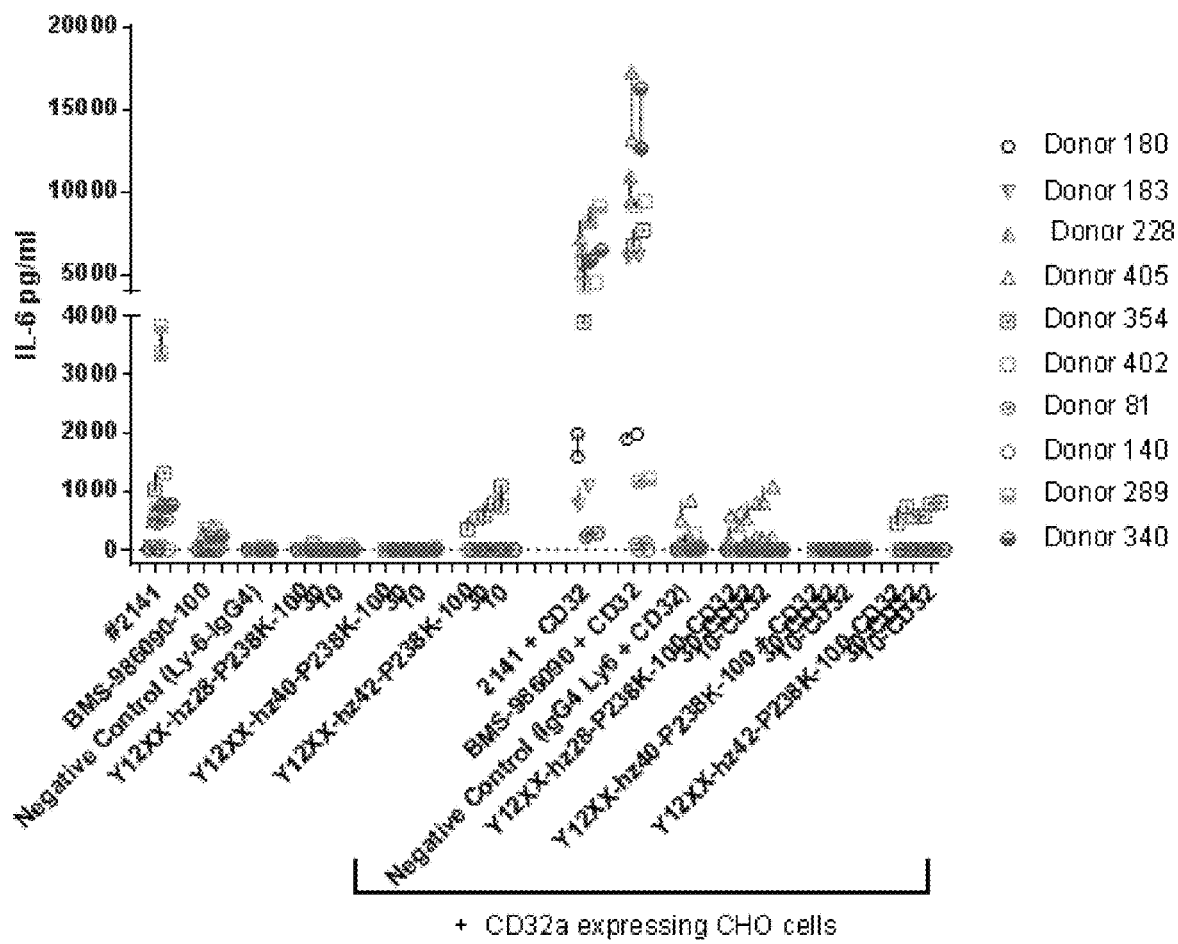
FIGS. 2A-2C depict iDC activation data for treatment of iDCs with humanized Y12XX antibodies or control antibodies with or without the addition of CD32a-expressing CHO cells. Increases in IL-6 (interleukin-6) from the cell culture media and cell surface marker expression, as indicated by flow cytometry mean fluorescence staining with anti-CD86 and anti-CD54 antibodies, were assessed.
Figure 2B:
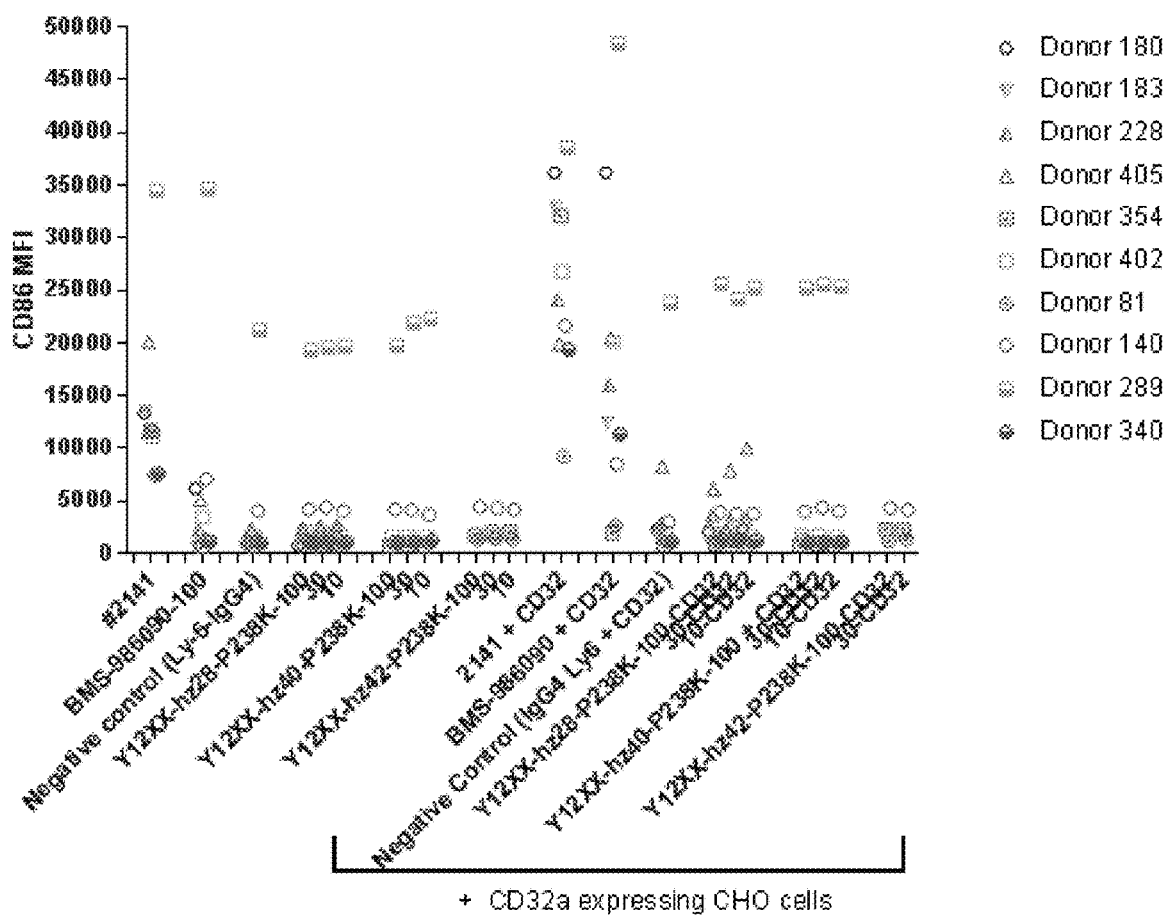
Figure 2C:
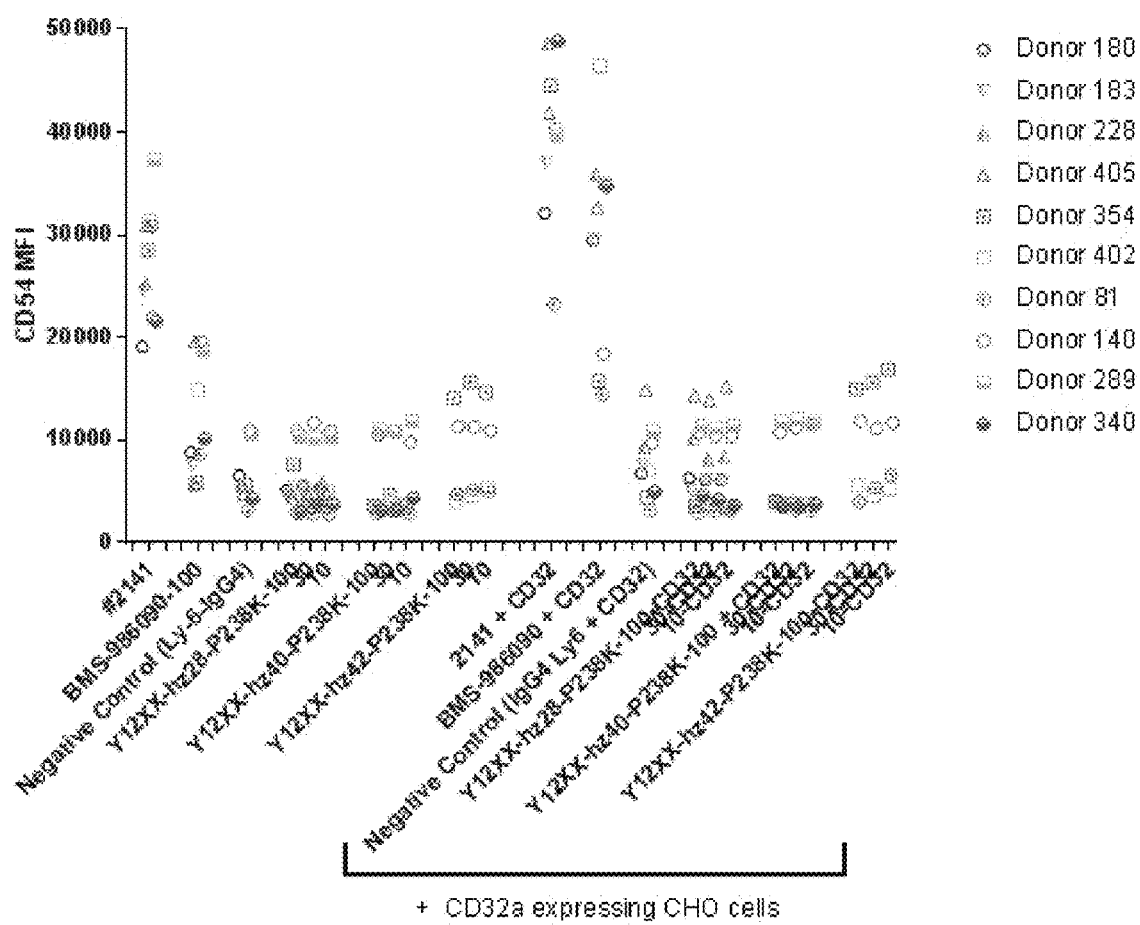

As illustrated by the data in FIGS. 2A-2C, the addition of either the partial agonist 2141 or BMS-986090 led to only weak activation of iDC in a subset of donors. However, addition of CD32a-expressing CHO cells to either 2141 or BMS-986090 led to robust increases in IL-6 production (FIG. 2B) and CD86 and CD54 upregulation (FIG. 2B and FIG. 2C, respectively) in nearly every donor tested, consistent with FcγR mediated clustering of these molecules through their Fc portions leading to CD40 activation. In contrast, Y12XX-hz28-P238K and Y12XX-hz40-P238K either alone or with CD32 dependent clustering did not show any signs of iDC activation above that observed with the negative control using iDC cells from 6-10 donors. Y12XX-hz42-P238K was tested in cells from 4 donors and exhibited signs of weak activation including IL-6 production and CD86 and CD54 upregulation in only one of the four donors, which, unlike the activity seen with 2141 or BMS-986090, was not dependent on the addition of CD32a-expressing CHO cells.

Materials and Methods for Examples 1 and 2

FcγR binding SPR: FcγR binding can be measured in vitro using purified FcγRs using methods, such as BIAcore™ surface plasmon resonance (SPR). One method tests the binding of purified His-tagged FcγR proteins (FcγR-his) to antibodies that are captured on a sensor surface containing protein A which has been immobilized using standard ethyl (dimethylaminopropyl) carbodiimide (EDC)/N-hydroxysuccinimide (NHS) chemistry with ethanolamine blocking. These experiments are performed on a BIAcore™ T200 instrument (GE Healthcare, Marlborough, Mass.) at 25° C. For example, samples of purified antibody at 3 μg/ml concentration are first captured on the immobilized protein A surface using a 15 second (s) contact time at 10 μl/min flow rate. This is followed by the binding of purified FcγR-His proteins at various concentrations, such as 10 μM-1.5 nM (2:1 dilution series) or 10 μM-13.7 nM (2:1 dilution series), using 120 s association and dissociation times at a flow rate of 30 ii/min. All steps are performed in a running buffer consisting of 10 mM NaPO$_4$, 130 mM NaCl, 0.05% p20 (PBS-T) pH 7.1. FcγR proteins tested in these studies include the "high affinity" FcγR CD64 (hFcγRI), as well as the "low affinity" FcγRs CD32a-H131 (FcγRIIa-H131), CD32a-R131 (FcγRIIa-R131), CD32b (FcγRIIb), CD16a-V158 (FcγRIIIa-V158), and CD16a-F158 (FcγRIIIa-F158), which were expressed and purified in house. SPR data are fit to either a 1:1 Langmuir model, or a 1:1 steady state model using BIAcore™ T200 evaluation software to obtain values for the association rate constant (ka), dissociation rate constant (kd) and dissociation constant ($K_D$).

To compare binding responses for different FcγRs, SPR data can be analyzed by calculating the maximum binding response as a percentage of the theoretical maximum binding response (% Rmax), using the equation:

% $R$max=(Binding Response Analyte)/[(($Mw$ Analyte)/($Mw$ Ligand))×(Response Ligand)×(analyte:ligand stoichiometry)]   EQUATION 1 where "Analyte" is the FcγR and "Ligand" is the captured antibody. This analysis does not take into account the mass of glycosylation of antibody or FcγR, and assumes 100% fractional activity for the captured ligand. Since the FcγRs are glycosylated, the % Rmax values are typically great than 100% under saturating conditions.

CD40 binding kinetics and affinity: The monovalent CD40 binding affinity of the antibody molecules is measured by surface plasmon resonance (SPR) on a BIAcore™ T200 instrument (GE Healthcare Life Sciences) at 25° C. or 37° C. by capturing antibody on an immobilized protein A sensor chip surface, and then binding human-CD40-monomer protein (generated in house) using, for example, an association time of 180 seconds, and dissociation time of 180 seconds or 360 seconds at 30 μl/min in PBS-T, pH 7.1. SPR data are fit to a 1:1 Langmuir model using BIAcore™ T200 evaluation software to obtain values for the association rate constant (ka), dissociation rate constant (kd) and dissociation constant (KD).

Titer analysis: Titer analysis was performed using Biolayer Interferometry (BLI) on an Octet® RED instrument (ForteBio, Freemont, Calif.) at 25° C. Antibodies are captured from supernatant using protein A sensor tips using association time of 120 seconds and the binding response is measured and compared to a standard curve obtained using a control antibody sample to determine the concentration of antibody in the supernatant.

Primary Cell Isolation and Culture: Peripheral blood mononuclear cells (PBMC) were isolated from heparinized human blood by Ficoll density gradient separation. Monocytes were isolated from PBMC following the Manual EasySep™ protocol (STEMCELL, Vancouver, Canada). One million of isolated monocytes were plated in in each well of a 6-well plate in 6 mLs of complete media (RPMI-1640, 10% heat-inactivated fetal bovine serum, 100 units/ml penicillin-streptomycin), containing IL-4 (100 ng/ml) and GM-CSF (100 ng/ml) and incubated for 6 days at 37° C./5% CO$_2$, changing media every other day and replacing it with fresh media containing the same concentration of cytokines. iDCs (immature dendritic cells) were harvested on day 6, washed thoroughly, and re-suspended in complete media.

Treatment of iDCs with anti-CD40 Antibodies in the Presence or Absence of FcγR Clustering/Crosslinking: Titrations of the various biological agents were made in complete media, and added to duplicate 96-well plates. In the case of cross-linking, antibodies were added to the cells for 30 min prior to the addition of CD32a-expressing CHO cells at a ratio of 1:6. Cells were incubated at 37° C./5% CO$_2$ for approximately 18-20 hours, 150 μL of supernatant was removed from each well, diluted 1:5 and evaluated for protein concentrations of IL-6, TNFα and IL-12 using a commercially available ELISA kits (R&D Systems, Minneapolis, Minn.), according to manufacturer's instructions. The cells remaining in the plates from the harvested supernatants were combined into 1 sample per duplicate treatment, and transferred to new 96-well round bottom (RB) plate, and placed at 4° C. Cells were washed with D-PBS, Ca++ and Mg++ free, and stained for 30 min on ice for cell viability using the LIVE/DEAD® Fixable Near-IR Dead Cell Stain Kit (Invitrogen, Carlsbad, Calif.). Cells were washed and re-suspended in D-PBS, Ca++ and Mg++ free, 2% FBS, 0.1% NaN$_3$ (staining buffer) and blocked with 5 μl/well of Human TruStain FcX™ (Fc Receptor Blocking Solution, Biolegend, San Diego, Calif.) in staining buffer.

DCs were immuno-stained with: PerCpCy5.5-conjugated αCD3, αCD19, αCD14 (Lin⁻), BUV395-conjugated αCD11c (BD Biosciences, San Diego, Calif.), APC-conjugated αCD86 (Biolegend, San Diego, Calif.), PE-conjugated αCD83 (eBioscience, San Diego, Calif.), FITC-conjugated αCD54 (Biolegend, San Diego, Calif.), and incubated at 4° C. for 45 minutes. Cells were washed twice in staining buffer and fixed (15 at RT, protected from light), by adding 100 μl of BD Cytofix Fixation Buffer (BD Bioscience, San Diego, Calif.). DCs were evaluated for CD86, ICAM-1 and CD83 expression using a LSRII-Fortessa Flow Cytometer (BD Biosciences, San Diego, Calif.), and FlowJo analysis software (Treestar, Ashland, Oreg.).

Inhibition of CD40L induced human B cell proliferation: Human tonsillar B cells were obtained from pediatric patients during routine tonsillectomy and isolated by mincing and gently mashing the tissue, passing the cells through a screen and isolating mononuclear cells with density gradient separation using human Lympholyte®-H separation media (Cedarlane Labs, Burlington, ON). Mononuclear cells were collected from the interface, washed, and rosetted with sheep red blood cells (SRBC, Colorado Serum Company; Denver, Colo.) for one hour at 4° C., followed by density gradient separation to remove T cells. Cells were again washed and re-suspended in RPMI containing 10% FBS (complete media). Titrations of antibodies were made in complete media, and added in triplicate to 96-well round bottom (RB) plates. $1 \times 10^5$ tonsillar human B cells were added and stimulated with either soluble IZ-hCD40L (2 μg/mL), or with Chinese hamster ovary cells stably transfected with human CD40L (CHO-hCD40L) irradiated with 10,000 rads, and plated at $2 \times 10^3$ cells/well, in a final volume of 200 μL in each well. Plates were incubated at 37° C./5% $CO_2$ for 72 hours, labeled for the last 6 hours with 0.5 μCi of $^3$[H]-thymidine per well, harvested, and counted by liquid scintillation. B cell proliferation was quantitated based on thymidine incorporation.

Example 3: In Vitro Fc Receptor Assays

Antibodies can exert effector functions, such as complement dependent cytotoxicity (CDC), and antibody dependent cellular cytotoxicity (ADCC), by binding of the Fc region to Fc gamma receptors (FcγRs) on the surface of immune cells or complement factors. Antibody dependent cellular phagocytosis is another potential Fc effector function. To further characterize the properties of the humanized Y12XX antibodies, the antibodies were assayed for complement dependent cytotoxicity (CDC), antibody dependent cellular phagocytosis (ADCP), and antibody dependent cellular cytotoxicity (ADCC). Table 15 lists the antibodies assayed in this example.

TABLE 15

| | Name | Reference |
|---|---|---|
| 1 | BMS-986291 (Y1238-hz1-P238K) | See WO 2018/217976 |
| 2 | 15B5-hz61-P238K | anti-CD40 antibody (produced in house) |
| 3 | 5F11-45-P238K | See WO 2018/217976 |
| 4 | Y12XX-hz28-P238K | |
| 5 | Y12XX-hz40-P238K | |
| 6 | Y12XX-hz42-P238K | |
| 7 | Antibody C | anti-CD40 antibody (See Ristov et al. (2018) Am J Transplant. 18(12): 2895-2904. Epub 2018 May 24.) |
| 8 | BI-LALA | See U.S. Pat. No. 9,090,696, heavy chain sequence SEQ ID NO: 32 and light chain sequence SEQ ID NO: 31; IgG1 isotype containing the mutations L234A-L235A |
| 9 | BMS-986090 | CD40 domain antibody (BMS3h-56-269-IgG$_4$ Fc fusion polypeptide); see, e.g., WO 2012/145673) |

TABLE 15-continued

| | Name | Reference |
|---|---|---|
| 10 | TT hIgG1 | Human anti-tetanus toxin antibody, IgG1 isotype (produced in house) (isotype control) |
| 11 | CD20 hI gG1 | Human anti-CD20, IgG2 isotype (produced in house) (positive control) |

The CDC assay was performed as follows. "CDC Assay Medium" refers to Roswell Park Memorial Institute medium (RPMI)-1640 (HyClone) with L-glutamine, phenol red-free (HyClone) supplemented with 0.1% BSA (Sigma), and 1% Penicillin-Streptomycin (Life Technologies). Fifty (50) microliters of target cells ($5 \times 10^5$ cells/mL in CDC assay medium) were added to wells of a 96-well assay plate. The target cells were Raji cells which endogenously express CD40 (obtained from ATCC). Serial dilutions (from 133 to 0.002 nM) were prepared for each antibody tested, and 25 microliters of each antibody concentration were added to each well. Twenty-five microliters of human complement (obtained from Quidel; diluted 1:3 with CDC assay medium) was added to each well. The assay plates were incubated at 37° C. for 4 hours in a humidified incubator. After the incubation, 100 microliters of CellTiter-Glo® (Promega, Madison, Wis.) was added to each well. Luminescence data was then acquired with a PerkinElmer EnVision® Plate Reader (PerkinElmer, Waltham, Mass.). Percent viability was calculated relative to isotype control (100% viable). The resulting values are plotted against antibody concentration. Percentage of cell viability is plotted for each antibody using Prism v5.01 software from GraphPad Inc.

Figure 3A:
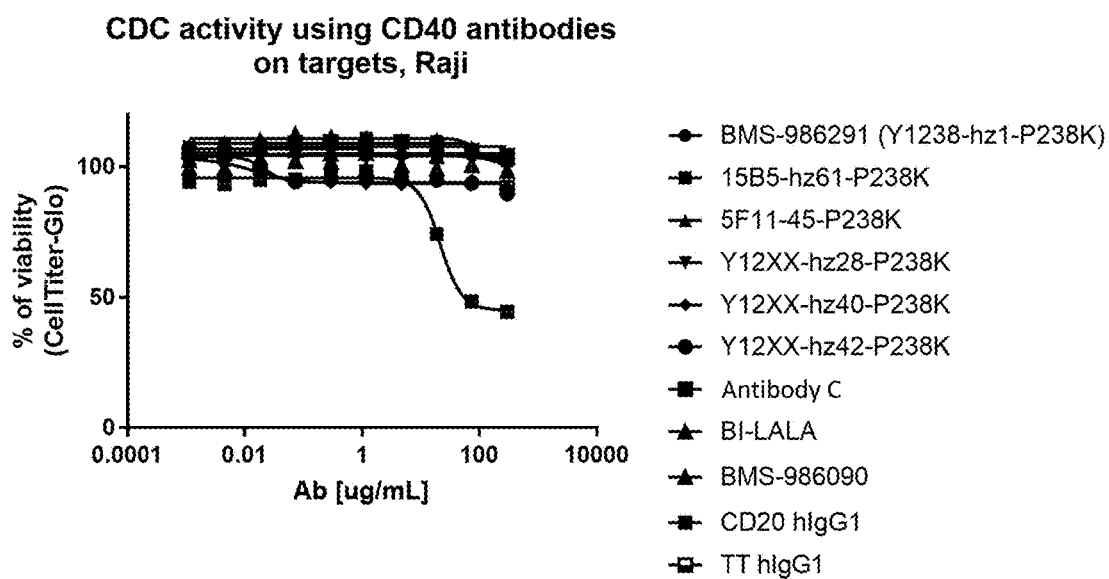
FIGS. 3A and 3B depict exemplary data from complement dependent cytotoxicity (CDC) analysis of humanized Y12XX antibodies, CD40 antibodies, and control antibodies. The CDC assay was performed twice. In the second assay, freshly thawed human complement serum was used.
Figure 3B:
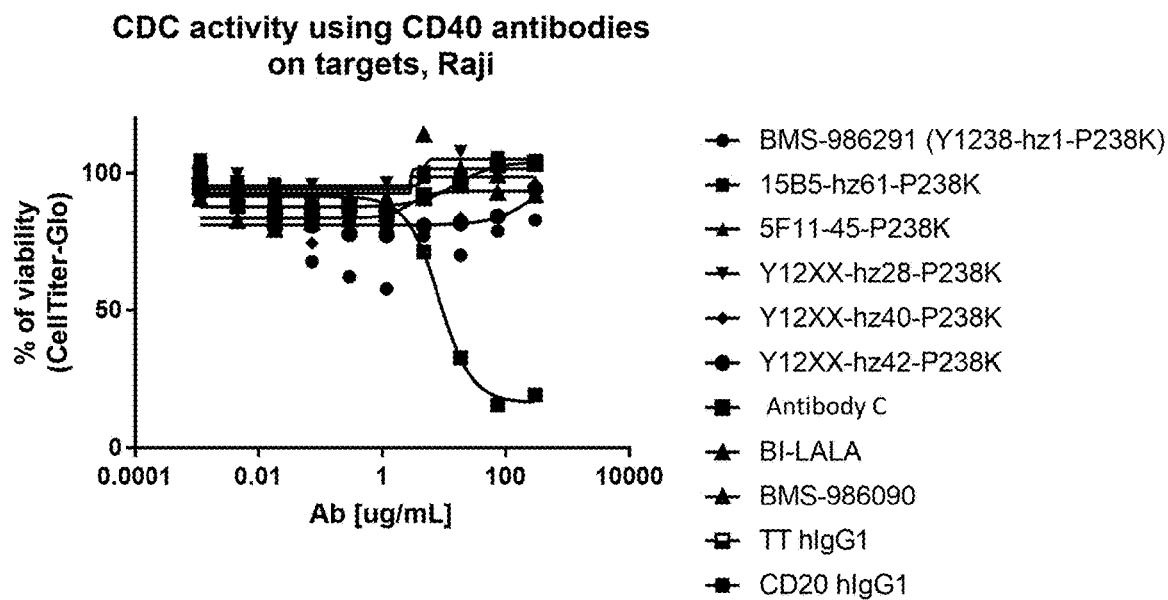

The CDC assay was performed twice. In the second assay, freshly thawed human complement serum was used. The results are depicted in FIGS. 3A and 3B. FIG. 3A depicts the first iteration of the assay, and FIG. 3B depicts the second iteration of the assay. CD20 hIgG1 is a positive control and showed cytotoxicity. No detectable CDC activity was present for the anti-CD40 antibodies assayed, and specifically, none of the humanized Y12XX antibodies assayed induced complement-dependent cytotoxicity.

The ADCP assay was performed as follows. "ADCP assay media" refers to RPMI-1640 media with L-glutamine, phenol red-free (HyClone) supplemented with 10% ultra-low IgG FBS (Gibco). The effector cells were primary human CD14+ monocytes purified from fresh PBMCs from 2 different healthy human donors. The target cells were again Raji cells. The Raji cells were labeled with 2.0 μM PKH26 (red fluorescent dye; Sigma), and the concentration was adjusted to $4 \times 10^6$ cells/mL in ADCP assay media. The labeled target cells were pre-coated with antibodies by adding labeled target cells (50 μL/well) to a V-bottom 96-well plate containing 50 μL/well of test or control antibody, and incubating for 30 minutes over ice. The cells were washed, then effector cells (CD14$^+$ monocytes) were added (100 μL/well) to result in a final effector cell-to-target cell ratio (E:T) of 1:4 and a final antibody concentration ranging from 30 nM to 0.1 nM. The plate was then placed in a humidified 37° C. incubator for 1 hour. Cells were stained with APC-anti-CD89 (BioLegend) for 30 min on ice and analyzed by flow cytometer (BD Canto™, BD Biosciences, San Jose, Calif.). Cells were gated for CD89+ cells and subsequently for stained phagocytosed effectors (CD89+, PKH26+). The percentage of phagocytosis was calculated as the population of CD89+, PKH26+ cells among the total CD89+ cells. Background value from the isotype control was subtracted to achieve the final percentage of phagocytosis. Data was analyzed using FlowJo software and Prism v5.01 software from GraphPad Inc.

Figure 4A:
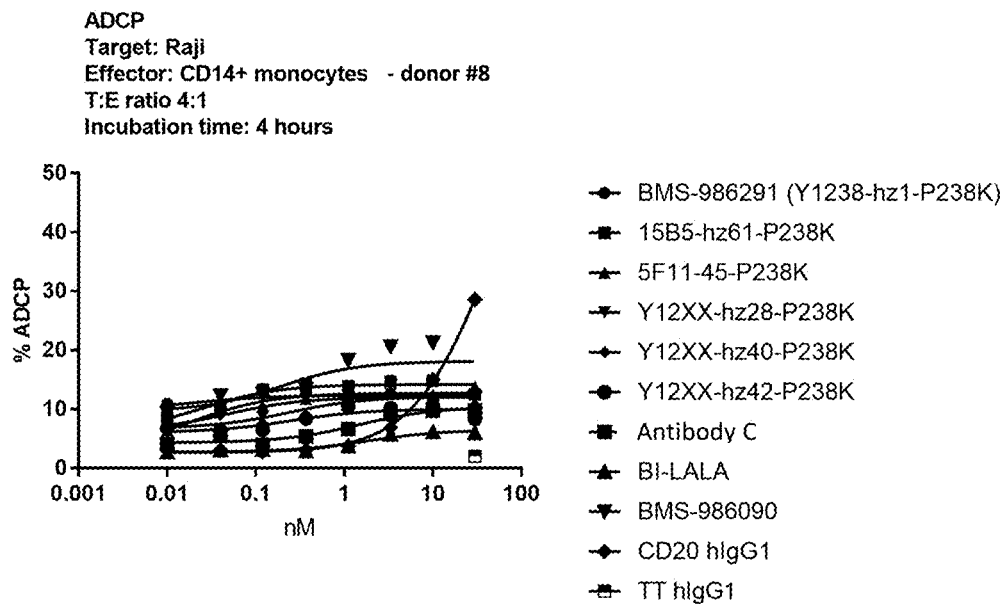
FIGS. 4A and 4B depict exemplary data from antibody dependent cellular phagocytosis (ADCP) analysis of humanized Y12XX antibodies or control antibodies, using CD14+ monocytes from two different donors as effector cells.
Figure 4B:
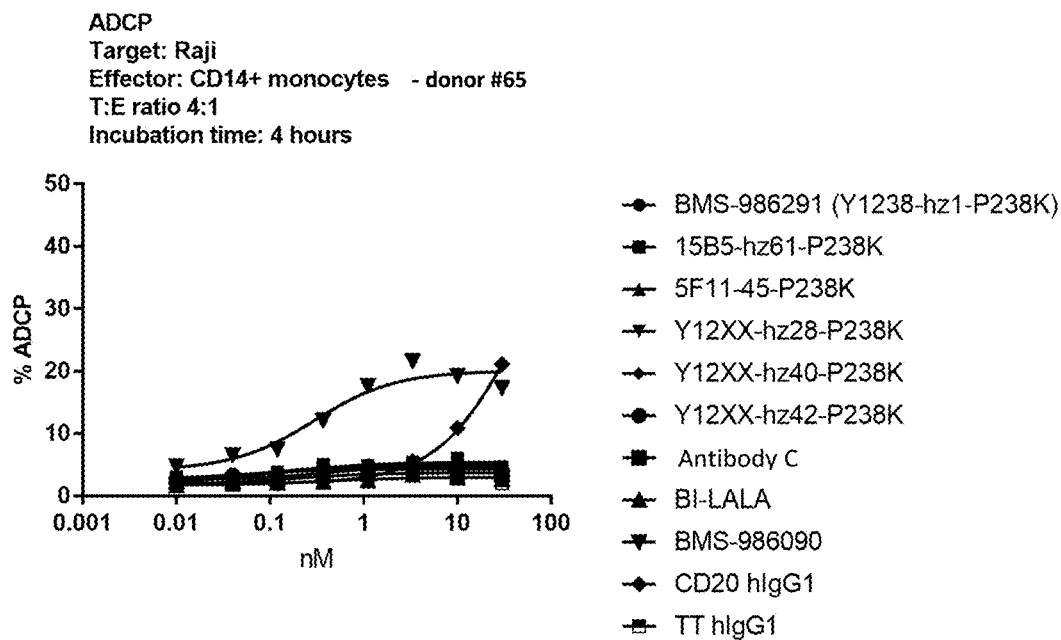

Exemplary data using CD14+ monocytes from two different donors are depicted in FIGS. 4A and 4B. CD20 hIgG1 is a positive control and induced phagocytosis of Raji cells, as expected. BMS-986090 also induced phagocytosis. In contrast, none of the other antibodies tested, including the humanized Y12XX anti-CD40 antibodies of this disclosure, induced detectable phagocytosis in this assay.

The ADCC assay was performed as follows. "ADCC assay media" refers to RPMI-1640 with L-glutamine, phenol red-free (HyClone) supplemented with 10% ultra-low IgG FBS (Gibco), and 1 mM sodium pyruvate (Life Technologies). Primary human NK (natural kill) cells were purified from fresh PBMCs from 2 different in-house donors, and used as effector cells. PBMC were purified from heparinized whole blood samples by density gradient centrifugation and washed with PBS supplemented with 2% FBS (HyClone). NK cells were isolated from PBMC by negative selection using a magnetic bead-based separation kit (Miltenyi Biotec). To activate the NK cells, purified NK cells were resuspended at $1 \times 10^6$ cells/mL in MyeloCult H5100 media (StemCell Technologies) supplemented with 1 µM hydrocortisone (StemCell Technologies) and 500 IU/mL recombinant human IL-2 (Peprotech) and incubated overnight at 37° C. The following day, activated NK effector cells were washed twice in ADCC assay media and the concentration was adjusted to $5 \times 10^5$ cells/mL in ADCC assay media. Raji cells (the target cells) were labeled with calcein, as follows. Calcein AM (Life Technologies) reagent was prepared by adding 20 µL of ultrapure DMSO to the reagent tube containing 50 µg of lyophilized reagent. A volume of 2 µL of reconstituted Calcein AM was added to the suspended Raji cells for every 1 mL of volume; the cells were vortexed and placed in a humidified 37° C. incubator for 30 minutes. After the incubation period, the labeled target cells were washed 3 times with ADCC assay media, and the concentration was adjusted to $10^5$ cells/mL in ADCC assay media. Labeled target cells (50 µL/well) were added to a V-bottom 96-well plate containing 50 µL/well of test or control antibody. Activated NK effector cells were then added (100 µL/well) to result in a final effector cell-to-target cell ratio (E:T) of 10:1, and a final antibody concentration ranging from 0.0002 to 1 µg/mL. The plate was then placed in a humidified 37° C. incubator for 2 hours. Supernatant (50 µL/well) was transferred into an optical 96-well black plate, and calcein release was measured by reading fluorescence intensity using an EnVision® Plate Reader (PerkinElmer, Waltham, Mass.) set to 485 excitation and 535 nm emission filters.

Target cells incubated with effector cells in the absence of antibody provided the control for background of antibody-independent lysis (spontaneous lysis), while target cells lysed with 20 µL/well 10% Tween-20 lysis buffer represented maximal release in the assay.

The percentage of antibody-dependent cell lysis was calculated based on mean fluorescence intensity (MFI) with the following formula:

$$\left( \frac{\text{test } MFI - \text{mean background}}{\text{mean maximum} - \text{mean background}} \right) \times 100 \quad \text{Equation 2}$$

Percentage of target cell lysis was plotted for each antibody using Prism v5.01 software from GraphPad Inc.

Figure 5A:
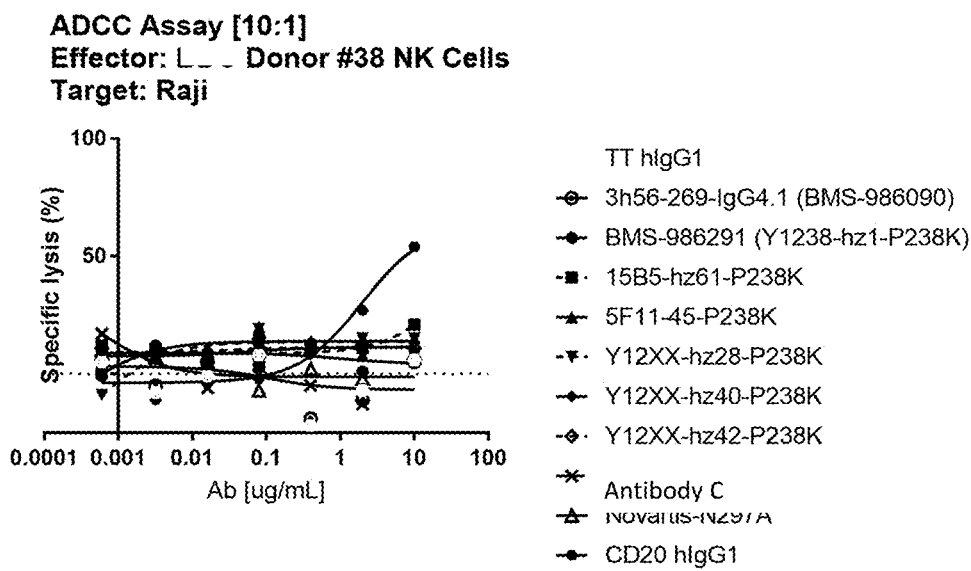
FIGS. 5A and 5B depict exemplary data from antibody dependent cellular cytotoxicity (ADCC) analysis of humanized Y12XX antibodies or control antibodies, using NK cells from two different donors as effector cells.
Figure 5B:
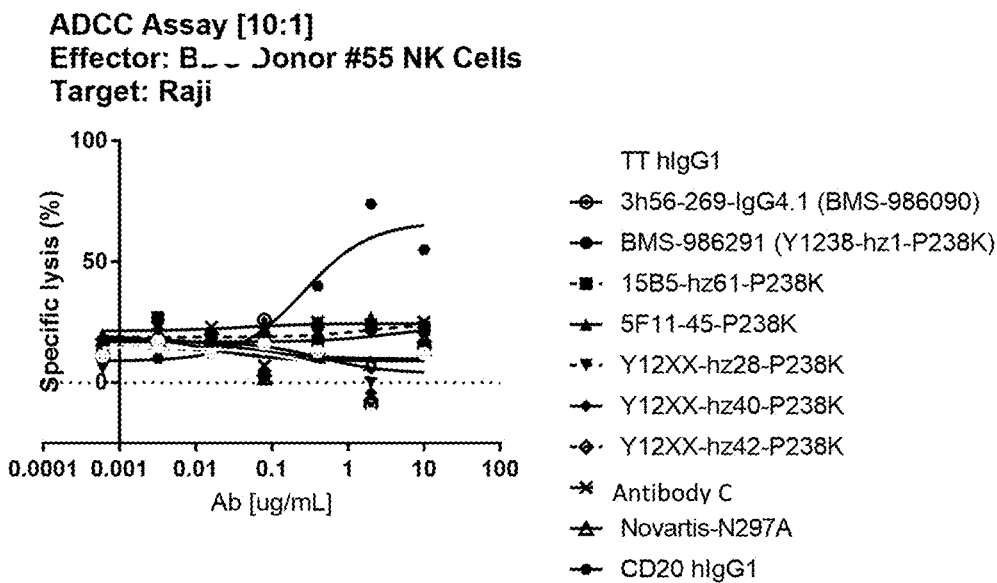

Exemplary data using NK cells from two different donors are depicted in FIGS. 5A and 5B. Target cells were killed by positive control anti-CD20 antibody. In contrast, ADCC is low-to-negative for all of the anti-CD40 antibodies, indicating that these antibodies do not induce antibody-dependent cytotoxicity of Raji cells and evidencing the CD40 antagonism of these antibodies.

In summary, in this example, the potential of the humanized Y12XX anti-CD40 antibodies of this disclosure, and specifically, Y12XX-hz28-P238K, Y12XX-hz40-P238K, and Y12XX-hz42-P238K, to mediate ADCC (antibody-dependent cellular cytotoxicity), ADCP (antibody-dependent cellular phagocytosis), or CDC (complement-dependent cytotoxicity) was tested using endogenous-CD40-expressing Raji cells as targets. Anti-CD20 antibody was used as a positive control. For ADCC, NK cells were used as effector cells, and two experiments were run with effector cells from different donors. In each case, none of Y12XX-hz28-P238K, Y12XX-hz40-P238K, and Y12XX-hz42-P238K induced lysis of Raji cells. None of Y12XX-hz28-P238K, Y12XX-hz40-P238K, and Y12XX-hz42-P238K induced CDC of Raji cells beyond the effect of human IgG1 isotype control. For ADCP, CD14+ monocytes were utilized as effector cells, and in this system none of Y12XX-hz28-P238K, Y12XX-hz40-P238K, and Y12XX-hz42-P238K promoted cellular phagocytosis. In contrast, BMS-986090 exhibited cellular phagocytosis.

Example 4: Assay of NF-kB/AP-1 Signaling

The objective of this example was to assess the NF-κB/AP-1 inducible SEAP (secreted embryonic alkaline phosphate) activity on Ramos-Blue™ Cells (InvivoGen) resulting from stimulation with anti-CD40 antibodies.

Ramos-Blue™ Cells are a human B lymphocyte reporter cell line that express an NF-κB/AP-1 inducible secreted embryonic alkaline phosphate (SEAP) reporter gene. The Ramos-Blue™ cell line has been used for NF-κB/AP1 signaling as well as in Toll-like Receptors' (TLR's) signaling pathways, Ramos-Blue™ Cells endogenously express CD40 and are responsive to CD40 and TLR. When Ramos-Blue™ Cells lines are stimulated, they produce SEAP in the cell culture supernatant. SEAP can be detected by using the QUANTI-Blue™ detection medium (InvivoGen, San Diego, Calif.). Levels of SEAP can be observed visually or by using a spectrophotometer at 620 nm. Ramos-Blue™ Cells do not express CD32 (FcγRII).

Table 6 lists the test materials (antibodies and other polypeptide) assayed in this example. All of the test materials were prepared in house by BMS.

TABLE 16

| Test Materials | Description |
| --- | --- |
| BMS-986325 | Y12XX-hz28-P238K (fully human anti-CD40 isotype hIgG (P238K) mAb |
| BMS-986090 | fully human anti-CD40 domain antibody IgG4 Fc fusion protein |
| mAb 134-2142 | (CD40-2142 (hIgG2-Fc)) fully human anti-CD40 monoclonal antibody (agonist) |
| Anti-DT1D12-B16F7-hIgG1.3f mAb | Negative Control |
| CD40L-IZ | a human CD4OL-Trimer (h-IZ-hCD40L-Trimer) |

Ramos-Blue™ Cells were purchased from InvivoGen. For this assay, a transduced cell line designated herein as Ramos Blue Cells #4, was prepared by transducing Ramos-Blue™ Cells with human CD32 (FcγRII). Both types of Ramos-Blue™ cells were cultures in Ramos Cell Culture Medium (Iscove's Modified Dulbecco's Medium (IMDM) supplemented with 10% Fetal Bovine Serum (FBS), 2 mM L-Glutamine, penicillin and streptomycin (100 U/mL-100 ug/mL), 100 ug/mL of Normomicin, and Zeocin as drug selection (100 ug/mL)). Cells were cultured at 37° C. in 5% $CO_2$. Both types of cells were passed every 3 days and maintained at a cell density of $0.5 \times 10^6$ cell/ml. Cells were used until cell passage #21 (P21). After P21, the cells were discarded.

The assay was performed as follows. "AIM V™ medium" refers to serum free medium supplemented with L-glutamine, 50 μg/mL streptomycin sulfate, 10 μg/mL gentamicin sulfate (Thermo Fisher Scientific). To assess CD40 agonist activity by CD40 antagonist antibodies on the NF-kB/AP-1 activity in Ramos Blue Cells #4, cells were washed twice (2×) with AIM V™ medium without antibiotics Normocin/Zeocin. The cells were then centrifuged at room temperature for 10 minutes at 2,000 rpm. Medium was aspirated carefully to not disrupt the cell pellet. One (1) mL of AIM V™ was added to the cell pellet to re-suspend the cell pellet, and an additional 9 ml of AIM V™ was added after resuspension. Cells were counted using the cell counter by adding 20 microliters (μl) ViaStain™ AOPI (acridine orange/propidium iodide) staining solution (Nexcelom Bioscience, LLC, Lawrence, Mass.) and 20 μl of Ramos-Blue™ Cells suspension.

Ramos-Blue™ Cells were adjusted to $4 \times 10^6$ cell/mL in AIM V™ serum free medium. One hundred (100) μl of 400K Ramos-Blue™ Cells were added per well in a flat bottom tissue culture plate. Then, 100 μl of BMS-986325, BMS-986090, mAb134-2141 (CD40-2142), or control was added to each corresponding well. CD40L-IZ was used as positive control. Ramos-Blue™ cells ($0.4 \times 10^6$ cells/well) in AIM V™ were included as negative control for the assay. The final volume was 200 μl/well.

Plates were incubated at 37° C. in a 5% $CO_2$ incubator for 20 hours. After 20 hours of cell culture, plates were centrifuged for 10 minutes at 2000 rpm.

Forty (40) μl of cell culture supernatant from stimulated Ramos cells were added to wells of a flat bottom plate. Then, 160 μl of QUANTI-Blue™ Solution was added per well. The final volume was 200 μl/well.

Plates were incubated at 37° C. in a 5% $CO_2$ incubator for 1 to 6 hours. SEAP levels were measured every 60 minutes at 620 nm using the EnVision® Reader Optical (OD: 620 nm).

Exemplary data are depicted in FIG. 6. In this example, anti-CD40 monoclonal antibodies were tested against Ramos-Blue™ Cells lacking CD32 or Ramos-Blue™ Cells transduced with CD32 (Ramos Blue #4) by assessing the NFκ-B/AP-1 inducible SEAP activity on Ramos-Blue™ Cells upon stimulation with anti-CD40 antibodies.

Figure 6A:
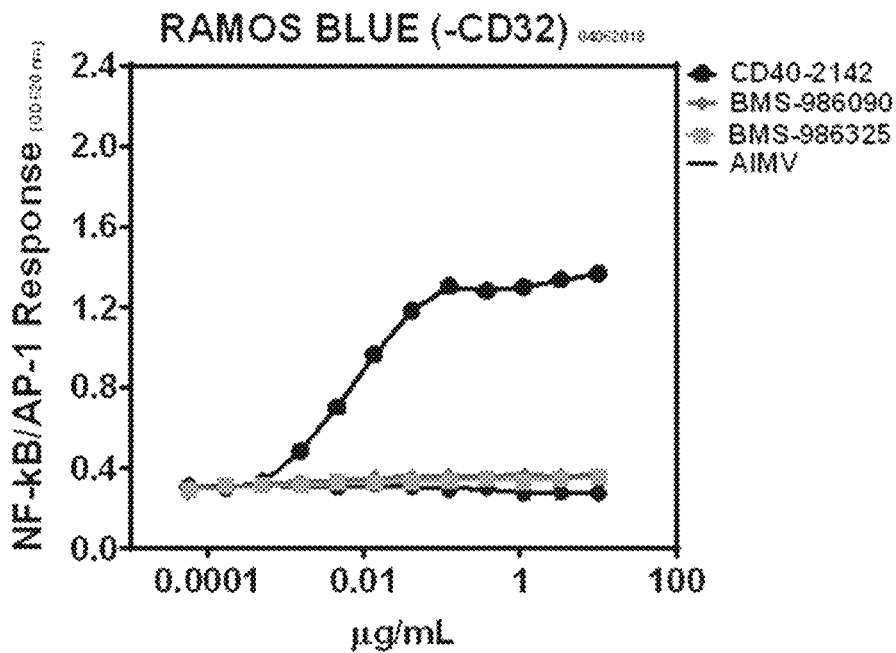
FIGS. 6A, 6B, 6C, and 6D depict data from an assay designed to assess the NF-kB/AP-1 inducible SEAP activity on Ramos Blues Cells upon stimulation with different anti-CD40 antibodies Representative results from three independent studies for the activity of CD40 mAbs are shown in FIGS. 6A and 6B.
Figure 6B:
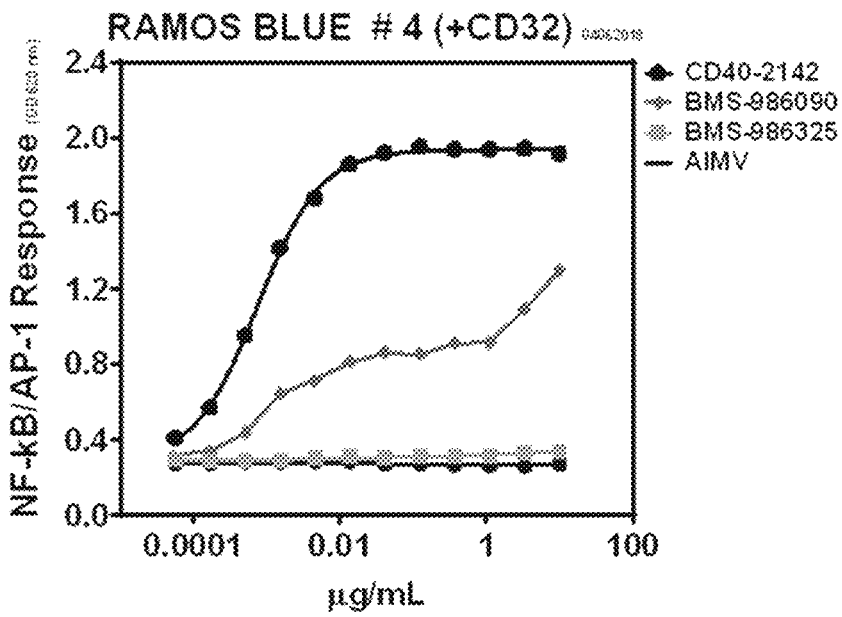
Figure 6C:
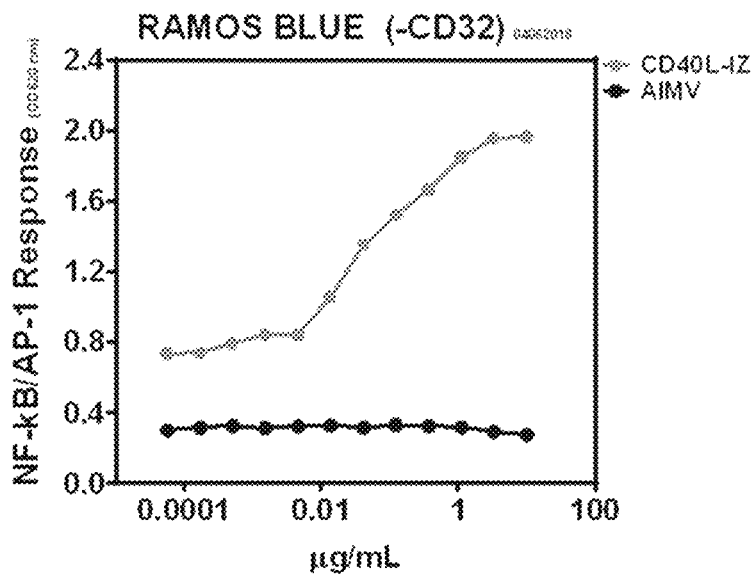
Figure 6D:
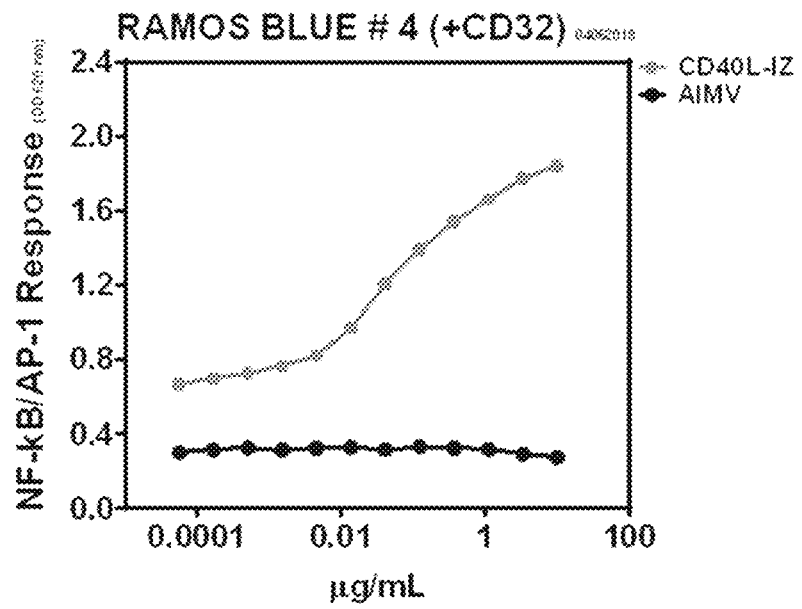

Addition of CD40-2142 induced a significant signaling response in this assay FIGS. 6A and 6b). These results indicate that CD40-2142 is a full agonist in this assay system. Addition of BMS-986090 showed no response by using the Ramos-Blue™ Cells (-CD32) (FIG. 6A), but displayed a partial agonism in the assay using the Ramos Blue Cells #4 (Ramos-Blue™ Cells transduced with CD32) (FIG. 6B). This result indicates FcγR dependency mediates the agonistic response induced by addition of BMS-986090. The control polypeptide, trimer CD40L-IZ, induced a response in both assays as reflected in FIGS. 6C and 6D.

In contrast, addition of BMS-986325 did not induce a significant NFκ-B/AP-1 response using either Ramos-Blue™ Cells (CD32⁻) (FIG. 6A) or Ramos #4 (CD32⁺) (FIG. 6B). These data indicate that BMS-986325 did not agonize CD40 and did not engage CD32 (FcγRII). These data support that reduced engagement of low affinity FcγRs, such as CD32 (FcγRII), reduces the likelihood of undesirable agonist signaling and undesirable potential for toxicity.

Example 7: Summary of Non-Clinical Pharmacokinetics Evaluation of BMS-986325

The pharmacokinetics (PK) of BMS-986325 (Y12XX-hz28-P238K) were evaluated in mice and cynomolgus monkeys. Since BMS-986325 does not cross react to murine CD40 receptors, the PK evaluated in mice is intrinsic or non-specific PK. BMS-986325 cross reacts with monkey CD40 receptors, therefore the total PK (specific and non-specific PK) was evaluated in monkeys. After intravenous (IV) administration of BMS-986325 (single 1- and 10-mg/kg doses) to mice, BMS-986325 exhibited low total serum clearance "CLT" of 0.5 to 1.02 mL/d/kg, limited volume of distribution at steady state "$V_{SS}$" of 0.12 to 0.19 L/kg, and long apparent elimination half-life "T-HALF" of 118 to 183 hours (~5 to 8 days).

In monkeys, a single subcutaneous (SC) dose of BMS-986325 was administered. The dose administered is a dose at which specific clearance (target-mediated drug disposition "TMDD") is not saturated. After the single SC dose, BMS-986325 was well absorbed, with an absolute bioavailability of 70.4% (relative to exposures at the same IV dose). After IV administration of BMS-986325 (10 mg/kg single dose) to monkeys, BMS-986325 exhibited a CLT of 0.41 mL/d/kg, a limited $V_{SS}$ of 0.05 L/kg, and a T-HALF of 100 hours (~4 days). The time to maximum plasma concentration "Tmax" following a single SC dose of BMS-986325 (doses of 1, 10, and 100 mg/kg administered) to monkeys was 24 to 54 hours. There were more-than-dose-proportional increases in exposure (maximum concentration "Cmax" and area under the concentration vs time curve extrapolated from time zero to infinity "AUC[INF]") and an increase in T-HALF with dose (~31, ~119, and ~197 hours at 1, 10, and 100 mg/kg, respectively). These data suggest nonlinear PK and a saturable clearance mechanism; this likely results from target (CD40)-mediated clearance, reflecting TMDD. In this single-dose PK study, anti-drug antibody (ADA) formation was detected in ~50% of monkeys, but had no apparent impact on the overall PK parameters.

Pharmacokinetic/pharmacodynamic modeling (TMDD model with quasi steady-state assumption [TMDD-$Q_{SS}$]) was used to describe the nonlinear PK observed in monkeys, establish a relationship between serum drug exposure and CD40 receptor occupancy (RO) and subsequent human dose projection.

Although the present embodiments have been described in detail with reference to examples above, it is understood that various modifications can be made without departing from the spirit of these embodiments, and would readily be known to the skilled artisan.

These and other aspects disclosed herein, including the exemplary specific treatment methods, medicaments, and uses listed herein, will be apparent from the teachings contained herein.

The invention claimed is:

1. A nucleic acid molecule encoding an isolated antibody or antigen binding portion thereof, that specifically binds to human CD40, wherein said antibody comprises a first polypeptide portion comprising a heavy chain variable region, and a second polypeptide portion comprising a light chain variable region, wherein:
said heavy chain variable region comprises a CDR1 comprising SEQ ID NO: 1, a CDR2 comprising SEQ ID NO: 2, a CDR3 comprising SEQ ID NO: 3; and
said light chain variable region comprises a CDR1 comprising SEQ ID NO: 7, a CDR2 comprising SEQ ID NO: 8, and a CDR3 comprising SEQ ID NO: 9.

2. An expression vector comprising the nucleic acid molecule of claim 1.

3. A cell transformed with the nucleic acid of claim 1.

4. A method of preparing an anti-human CD40 antibody, or antigen binding portion thereof, comprising:
a) expressing the antibody, or antigen binding portion thereof, in the cell of claim 3; and
b) isolating the antibody, or antigen binding portion thereof, from the cell.

5. The nucleic acid molecule of claim 1, wherein said antibody or antigen binding portion thereof antagonizes a CD40 activity.

6. The nucleic acid molecule of claim 1, wherein said heavy chain variable region comprises a CDR1 consisting of SEQ ID NO: 1, a CDR2 consisting of SEQ ID NO: 2, a CDR3 consisting of SEQ ID NO: 3; and
said light chain variable region comprises a CDR1 consisting of SEQ ID NO: 7, a CDR2 consisting of SEQ ID NO: 8, and a CDR3 consisting of SEQ ID NO: 9.

7. The nucleic acid molecule of claim 1, wherein said heavy chain variable region comprises the amino acid sequence of SEQ ID NO: 4, and said light chain variable region comprises the amino acid sequence of SEQ ID NO: 10.

8. The nucleic acid molecule of claim 1, wherein said heavy chain variable region comprises the amino acid sequence of SEQ ID NO: 4, and said light chain variable region comprises the amino acid sequence of SEQ ID NO: 16.

9. The nucleic acid molecule of claim 1, wherein said first polypeptide portion comprises a human heavy chain constant region; and said second polypeptide portion comprises a human light chain constant region.

10. The nucleic acid molecule of claim 9, wherein said human heavy chain constant region is a human IgG1 Fc domain comprising either
(1) a mutation at Kabat position 238 that reduces binding to Fc-gamma-receptors (FcγRs), wherein proline 238 (P238) is mutated to one of the residues selected from the group consisting of: lysine, serine, alanine, arginine, and tryptophan, and wherein the antibody or antigen binding portion thereof has reduced FγR binding; or
(2) an alanine substituted at Kabat position 297.

11. The nucleic acid molecule of claim 9, comprising a human IgG1 Fc domain comprising a mutation at Kabat position 238 that reduces binding to Fc-gamma-receptors (FcγRs), wherein proline 238 (P238) is mutated to one of the residues selected from the group consisting of: lysine, serine, alanine, arginine, and tryptophan, and wherein the antibody or antigen binding portion has reduced FcγR binding.

12. The nucleic acid molecule of claim 11, wherein P238 is mutated to lysine.

13. The nucleic acid molecule of claim 12, wherein the Fc domain comprises an amino acid sequence selected from: SEQ ID NO: 22, SEQ ID NO: 23, SEQ ID NO: 24, SEQ ID NO: 25, SEQ ID NO: 26, SEQ ID NO: 27, SEQ ID NO: 28, or SEQ ID NO: 29.

14. The nucleic acid molecule of claim 10, wherein said heavy chain variable region comprises a CDR1 consisting of SEQ ID NO: 1, a CDR2 consisting of SEQ ID NO: 2, a CDR3 consisting of SEQ ID NO: 3; and
said light chain variable region comprises a CDR1 consisting of SEQ ID NO: 7, a CDR2 consisting of SEQ ID NO: 8, and a CDR3 consisting of SEQ ID NO: 9.

15. The nucleic acid molecule of claim 14, wherein the human IgG1 Fc domain comprises the amino acid sequence of SEQ ID NO: 22 or SEQ ID NO: 23.

16. The nucleic acid molecule of claim 1, wherein the first polypeptide portion comprises or consists of an amino acid sequence selected from the group consisting of:
SEQ ID NO: 5, SEQ ID NO: 6, SEQ ID NO: 30, and SEQ ID NO: 31; and
the second polypeptide portion comprises or consists of the amino acid sequence of SEQ ID NO: 11.

17. The nucleic acid molecule of claim 1, wherein the first polypeptide portion comprises an amino acid sequence of SEQ ID NO: 5; and
the second polypeptide portion comprises the amino acid sequence of SEQ ID NO: 11.

18. The nucleic acid molecule of claim 1, wherein the first polypeptide portion consists of an amino acid sequence of SEQ ID NO: 5; and the second polypeptide portion consists of the amino acid sequence of SEQ ID NO: 11.

19. The nucleic acid molecule of claim 1, wherein the isolated antibody or antigen binding portion thereof is humanized.

20. The nucleic acid molecule of claim 1, wherein the antigen binding portion is an scFv-Fc.

21. The nucleic acid molecule of claim 1, wherein the antibody or antigen-binding portion thereof is linked to a therapeutic agent.

22. The nucleic acid molecule of claim 1, wherein the antibody or antigen-binding portion thereof is linked to a second functional moiety having a different binding specificity than said antibody or antigen binding portion thereof.

23. The nucleic acid molecule of claim 1, further comprising an additional moiety.

* * * * *

UNITED STATES PATENT AND TRADEMARK OFFICE
CERTIFICATE OF CORRECTION

PATENT NO. : 11,795,231 B2
APPLICATION NO. : 17/670223
DATED : October 24, 2023
INVENTOR(S) : Aaron Yamniuk et al.

Page 1 of 1

It is certified that error appears in the above-identified patent and that said Letters Patent is hereby corrected as shown below:

In the Claims

At Column 172, Claim number 10, Line number 9, replace "has reduced FγR binding" with -- has reduced FcγR binding --

Signed and Sealed this
Sixth Day of August, 2024

Katherine Kelly Vidal
Director of the United States Patent and Trademark Office